United States Patent
Ohkawa et al.

(10) Patent No.: US 6,248,766 B1
(45) Date of Patent: Jun. 19, 2001

(54) TRICYCLIC COMPOUNDS, THEIR PRODUCTION AND USE

(75) Inventors: Shigenori Ohkawa, Takatsuki; Masaki Setoh, Suita; Zen-ichi Terashita, Toyonaka, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/254,446

(22) PCT Filed: Sep. 24, 1997

(86) PCT No.: PCT/JP97/03384

§ 371 Date: Mar. 9, 1999

§ 102(e) Date: Mar. 9, 1999

(87) PCT Pub. No.: WO98/13356

PCT Pub. Date: Apr. 2, 1998

(30) Foreign Application Priority Data

Sep. 25, 1996 (JP) .................................................. 8-252912

(51) Int. Cl.⁷ ...................... A61K 31/428; A61K 31/429; C07D 513/04; C07D 277/84; C07D 277/76
(52) U.S. Cl. ........................... 514/366; 548/150; 548/151
(58) Field of Search .................................... 548/150, 151; 514/366

(56) References Cited

U.S. PATENT DOCUMENTS

| | | | |
|---|---|---|---|
| 3,792,057 | 2/1974 | Jensen et al. | 260/309 |
| 4,305,954 | 12/1981 | Finizio et al. | 424/273 R |
| 4,371,541 | 2/1983 | Finizio | 424/273 R |
| 4,548,943 | 10/1985 | Finizio et al. | 514/393 |

FOREIGN PATENT DOCUMENTS

| | | |
|---|---|---|
| 0 057 932 | 8/1982 | (EP) . |
| 0 230 334 | 7/1987 | (EP) . |
| 1484615 | 9/1977 | (GB) . |
| 01040468 | 2/1989 | (JP) . |
| 01193253 | 8/1989 | (JP) . |
| 01211580 | 8/1989 | (JP) . |
| WO 96 20925 | 7/1996 | (WO) . |
| WO 96 25411 | 8/1996 | (WO) . |

*Primary Examiner*—Laura L. Stockton
(74) *Attorney, Agent, or Firm*—Philippe Y. Riesen; Mark Chao

(57) ABSTRACT

A compound of the formula:

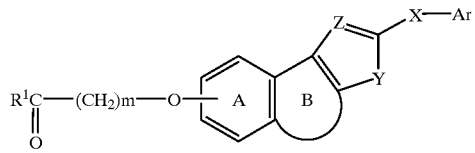

wherein $R^1$ is H or a substituent; m is 1–3; Ar is an aromatic group which may be substituted; X is a bond or a divalent straight-chain group having 1–6 atoms which may be substituted; Y is —S—, —O—, or —N($R^2$)— ($R^2$ is H or a substituent group), Z is —N= or —C($R^3$)= ($R^3$ is H or a hydrocarbon group), ring A is a benzene ring; ring B is a 5- to 7-membered ring which may be substituted, or a salt thereof is useful for eliciting a prostaglandin $I_2$ receptor agonistic effect.

27 Claims, No Drawings

TRICYCLIC COMPOUNDS, THEIR PRODUCTION AND USE

This application is the National Phase of International Patent Application PCT/JP97/03384, filed Sep 24, 1997.

TECHNICAL FIELD

The present invention relate to tricyclic compounds having very satisfactory prostaglandin $I_2$ receptor agonistic activity, their production, intermediates and use.

BACKGROUND ART

It is known that prostaglandin $I_2$ ($PGI_2$) is a substance which is biosynthesized from arachidonic acid through prostaglandin $H_2$ ($PGH_2$) and has potent platelet aggregation inhibitory activity, vasodilative activity, lipid deposition inhibitory activity, and leukocyte activation inhibitory activity. As such, $PGI_2$ is considered to be effective in the treatment of peripheral vascular diseases (e.g. peripheral embolism, vibration syndrome, Raynaud's disease, etc.), systemic lupus erythematosus, post-PTCA (percutaneous transluminal coronary angioplasty) arterial reobliteration/restenosis, atherosclerosis, thrombosis, diabetic neuropathy, hypertension, ischemic diseases (e.g. cerebral infarction, myocardial infarction, etc.), transient ischemic attack, and glomerulonephritis.

Meanwhile, WO 96/20925, for instance, reports a nonprostanoid $PGI_2$ receptor agonist compound of the formula:

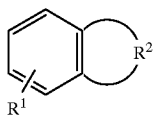

wherein $R^1$ represents —X—$(CH_2)_n$COOR$^3$ wherein X represents —O—, —S— or —CH$_2$—; $R^3$ typically represents hydrogen or $C_{1-5}$ lower alkyl; n represents 1–3; $R^2$ typically represents —CR$^4$=CR$^5$—O— or —CR$^5$=CR$^4$—O— wherein $R^4$ represents —$(CH_2)_m$—Y—$R^8$ wherein m represents 1–4; Y typically represents —O— or —CH$_2$—; $R^8$ typically represents phenyl; $R^5$ typically represents hydrogen or $C_{1-5}$ lower alkyl.

JP-A-62-252780 discloses an antiulcer tricyclic compound of the formula:

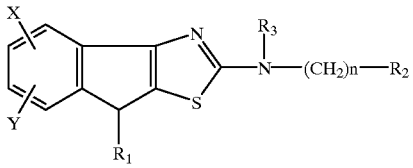

wherein X and Y independently represent hydrogen, halogen, lower alkyl or lower alkoxy; n represents 0–4; $R_1$ represents hydrogen, lower alkyl, unsubstituted or substituted phenyl; $R_2$ typically represents lower alkyl, unsubstituted or substituted phenyl, heterocyclic group or cyclic amino; $R_3$ represents hydrogen, lower alkyl, or acyl; $R_2$ and $R_3$ optionally taken together represent cyclic amino.

$PGI_2$ is by no means chemically and biologically stable enough for use as a medicine. Moreover, it is not clear-cut in the desired action or actions versus other actions, thus unavoidably inducing adverse drug reactions.

Meanwhile, no information is available on the relation of those known tricyclic compounds to the affinity for $PGI_2$ receptors. Under the circumstances, there is a keen demand for creation of a compound structurally removed from $PGI_2$ and yet having a high affinity for $PGI_2$ receptors and acting as a $PGI_2$ receptor agonist with improved chemical stability and stability against metabolism and greater clinical efficacy than $PGI_2$, thus being very satisfactory for use as a medicine.

The inventors of the present invention explored for compounds having $PGI_2$ receptor agonistic activity and succeeded in the creation of a compound of the formula:

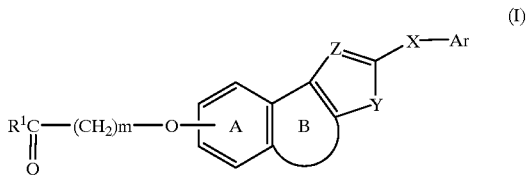

wherein $R^1$ represents hydrogen or a substituent group;

m represents an integer of 1 to 3;

Ar represents an aromatic group which may be substituted;

X represents a bond or a divalent straight-chain group which have 1 to 6 atoms and may be substituted;

Y represents —S—, —O— or —N(R$^2$)— wherein R represents hydrogen or a substituent group;

Z represents —N= or —C(R$^3$)= wherein $R^3$ represents hydrogen or a hydrocarbon group;

ring A represents a benzene ring which may be substituted by a substituent in addition to a group of the formula: —O(CH$_2$)$_m$COR$^1$ wherein the respective symbols have the same meanings as defined above; and ring B represents a 5- to 7-membered ring which may be substituted, or a salt thereof, which compound is structurally characterized in that the benzene ring (ring A) of the tricyclic skeletal system of the formula:

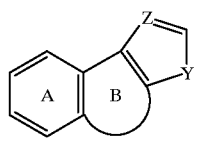

wherein the respective symbols have the meanings defined above, has a substituent group of the formula —O(CH$_2$)$_m$COR$^1$ wherein the respective symbols have the meanings defined above.

The inventors further discovered that because of the above unique chemical structure, the above compound or a salt thereof [hereinafter sometimes referred to briefly as compound (I)], is an excellent $PGI_2$ receptor agonist having a high affinity for $PGI_2$ receptors, high chemical stability, and high stability against metabolism and, thus, being fully satisfactory as a medicine. The present invention is predicated on the above findings.

DISCLOSURE OF INVENTION

The present invention to:

(1) compound (I);

(2) a compound of the above (1) wherein $R^1$ is (i) hydrogen, (ii) a hydroxy which may be substituted by a $C_{1-6}$ alkyl, $C_{1-6}$ alkenyl, $C_{2-6}$ alkynyl, $C_{3-6}$ cycloalkyl, $C_{6-14}$ aryl or $C_{7-16}$ aralkyl group, each of which may be substituted by 1 to 5 substituents selected from the group consisting of halogen, $C_{1-6}$ alkyl which may be halogenated, $C_{2-6}$ alkenyl which may be halogenated, $C_{2-6}$ alkynyl which may be halogenated, $C_{3-6}$ cycloalkyl which may be halogenated, $C_{6-10}$ aryl, $C_{7-11}$ aralkyl, $C_{1-6}$ alkoxy which may be halogenated, $C_{6-10}$ aryloxy, $C_{1-6}$ alkyl-carbonyl, $C_{6-10}$ aryl-carbonyl, $C_{7-11}$ aralkyl-carbonyl, $C_{1-6}$ alkyl-carbonyloxy, $C_{6-10}$ aryl-carbonyloxy, carboxy, $C_{1-6}$ alkoxy-carbonyl, carbamoyl, mono-$C_{1-6}$ alkyl-carbamoyl, di-$C_{1-6}$ alkyl-carbamoyl, amidino, imino, amino, mono-$C_{1-6}$ alkylamino, di-$C_{1-6}$ alkylamino, 3- to 6-membered cyclic amino, $C_{1-3}$ alkylenedioxy, hydroxy, nitro, cyano, mercapto, sulfo, sulfino, phosphono, sulfamoyl, mono-$C_{1-6}$ alkylsulfamoyl, di-$C_{1-6}$ alkylsulfamoyl, $C_{1-6}$ alkylthio which may be halogenated, $C_{6-10}$ arylthio, $C_{1-6}$ alkylsulfinyl, $C_{6-10}$ arylsulfinyl, $C_{1-6}$ alkylsulfonyl and $C_{6-10}$ arylsulfonyl, or (iii) an amino which may be substituted by 1 or 2 substituents selected from the group consisting of $C_{1-6}$ alkyl, $C_{1-6}$ alkenyl, $C_{1-6}$ alkynyl, $C_{3-6}$ cycloalkyl, $C_{6-14}$ aryl and $C_{7-16}$ aralkyl group, each of which may be substituted by 1 to 5 substituents selected from the group consisting of halogen, $C_{1-6}$ alkyl which may be halogenated, $C_{2-6}$ alkenyl which may be halogenated, $C_{2-6}$ alkynyl which may be halogenated, $C_{3-6}$ cycloalkyl which may be halogenated, $C_{6-10}$ aryl, $C_{7-11}$ aralkyl, $C_{1-6}$ alkoxy which may be halogenated, $C_{6-10}$ aryloxy, $C_{1-6}$ alkyl-carbonyl, $C_{6-10}$ aryl-carbonyl, $C_{7-11}$ aralkyl-carbonyl, $C_{1-6}$ alkyl-carbonyloxy, $C_{6-10}$ aryl-carbonyloxy, carboxy, $C_{1-6}$ alkoxy-carbonyl, carbamoyl, mono-$C_{1-6}$ alkyl-carbamoyl, di-$C_{1-6}$ alkyl-carbamoyl, amidino, imino, amino, mono-$C_{1-6}$ alkylamino, di-$C_{1-6}$ alkylamino, 3- to 6-membered cyclic amino, $C_{1-3}$ alkylenedioxy, hydroxy, nitro, cyano, mercapto, sulfo, sulfino, phosphono, sulfamoyl, mono-$C_{1-6}$ alkylsulfamoyl, di-$C_{1-6}$ alkylsulfamoyl, $C_{1-6}$ alkylthio which may be halogenated, $C_{6-10}$ arylthio, $C_{1-6}$ alkylsulfinyl, $C_{6-10}$ arylsulfinyl, $C_{1-6}$ alkylsulfonyl and $C_{6-10}$ arylsulfonyl;

m is an integer of 1 to 3;

Ar is a (i) $C_{6-14}$ aryl or (ii) 5- to 10-membered aromatic heterocyclic group containing 1 to 4 hetero atoms selected from among nitrogen, sulfur and oxygen as a ring member other than carbon, each of which may be substituted by 1 to 5 substituents selected from the group consisting of halogen, $C_{1-3}$ alkylenedioxy, nitro, cyano, $C_{1-6}$ alkyl which may be halogenated, $C_{3-6}$ cycloalkyl, $C_{1-6}$ alkoxy which may be halogenated, $C_{3-6}$ alkylthio which may be halogenated, hydroxy, amino, mono-$C_{1-6}$ alkylamino, di-$C_{1-6}$ alkylamino, $C_{1-6}$ alkyl-carbonyl, carboxy, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, sulfo, $C_{1-6}$ alkylsulfonyl, $C_{6-10}$ aryl and $C_{6-10}$ aryloxy;

X is (i) a bond or (ii) a divalent group of the formula: —Xa—Xb— wherein Xa is a bond, S, SO, $SO_2$, O or $NR^4$, wherein $R^4$ is hydrogen, $C_{1-6}$ alkyl, $C_{3-6}$ cycloalkyl, $C_{6-14}$ aryl, $C_{7-11}$ aralkyl, formyl, $C_{1-6}$ alkyl-carbonyl or $C_{6-10}$ aryl-carbonyl; and Xb is (a) a bond or (b) $C_{1-5}$ alkylene, $C_{2-5}$ alkenylene, $C_{2-5}$ alkynylene or a group of the formula: —$(CH_2)_p$—Xc—$(CH_2)_q$— wherein Xc is S, SO, $SO_2$, O or $NR^{4a}$, wherein $R^{4a}$ is hydrogen, $C_{1-6}$ alkyl, $C_{3-6}$ cycloalkyl, $C_{6-14}$ aryl, $C_{7-11}$ aralkyl, formyl, $C_{1-6}$ alkyl-carbonyl or $C_{6-10}$ aryl-carbonyl; p and q are independently an integer of 0 to 4 and p+q is an integer of 0 to 4, each of which group may be substituted by 1 to 5 substituents selected from the group consisting of (1) halogen, (2) nitro, (3) cyano, (4) $C_{1-6}$ alkyl which may be halogenated, (5) $C_{3-6}$ cycloalkyl, (6) $C_{7-11}$ aralkyl, (7) $C_{1-6}$ alkoxy which may be halogenated, (8) $C_{1-6}$ alkylthio which may be halogenated, (9) hydroxy, (10) amino, (11) mono-$C_{1-6}$ alkylamino, (12) di-$C_{1-6}$ alkylamino, (13) $C_{6-10}$ aryloxy, (14) $C_{1-6}$ alkyl-carbonyl, (15) $C_{6-10}$ aryl-carbonyl, (16) oxo and (17) a (17-i) $C_{6-14}$ aryl or (17-ii) 5- to 10-membered aromatic heterocyclic group containing 1 to 4 hetero atoms selected from among nitrogen, sulfur and oxygen as a ring member other than carbon, each of which may be substituted by 1 to 5 substituents selected from the group consisting of halogen, $C_{1-3}$ alkylenedioxy, nitro, cyano, $C_{1-6}$ alkyl which may be halogenated, $C_{3-6}$ cycloalkyl, $C_{1-6}$ alkoxy which may be halogenated, $C_{1-6}$ alkylthio which may be halogenated, hydroxy, amino, mono-$C_{1-6}$ alkylamino, di-$C_{1-6}$ alkylamino, $C_{1-6}$ alkyl-carbonyl, carboxy, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, sulfo, $C_{1-6}$ alkylsulfonyl, $C_{6-10}$ aryl and $C_{6-10}$ aryloxy;

$R^2$ is (i) hydrogen, (ii) $C_{1-6}$ alkyl, (iii) $C_{1-6}$ alkenyl, (iv) $C_{1-6}$ alkynyl, (v) $C_{3-6}$ cycloalkyl, (vi) $C_{6-14}$ aryl, (vii) $C_{7-16}$ aralkyl, (viii) formyl, (ix) $C_{1-6}$ alkyl-carbonyl, (x) $C_{6-10}$ aryl-carbonyl, (xi) $C_{7-11}$ aralkyl-carbonyl, (xii) $C_{1-6}$ alkylsulfonyl, (xiii) $C_{6-10}$ arylsulfonyl which may be substituted by 1 to 3 substituents selected from the group consisting of $C_{1-6}$ alkyl, $C_{1-6}$ alkoxy and nitro or (xiv) $C_{7-11}$ aralkylsulfonyl;

$R^3$ is hydrogen, $C_{1-6}$ alkyl, $C_{1-6}$ alkenyl, $C_{1-6}$ alkynyl, $C_{3-6}$ cycloalkyl, $C_{6-14}$ aryl or $C_{7-16}$ aralkyl;

ring A is a benzene ring which may be substituted by 1 to 3 substituents selected from the group consisting of halogen, $C_{1-3}$ alkylenedioxy, nitro, cyano, $C_{1-6}$ alkyl which may be halogenated, $C_{3-6}$ cycloalkyl, $C_{1-6}$ alkoxy which may be halogenated, $C_{1-6}$ alkylthio which may be halogenated, hydroxy, amino, mono-$C_{1-6}$ alkylamina, di-$C_{1-6}$ alkylamino, $C_{1-6}$ alkyl-carbonyl, carboxy, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, sulfo, $C_{1-6}$ alkylsulfonyl, $C_{6-10}$ aryl and $C_{6-10}$ aryloxy, in addition to a group of the formula: —$O(CH_2)_mCOR^1$; and ring B is a 5- to 7-membered ring of the formula:

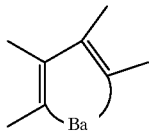

wherein Ba is —$CH_2$—, —$(CH_2)_2$—, —$(CH_2)_3$—, —CH=CH—, —O—, —O—$CH_2$—, —$CH_2$—O—, —O—$CH_2$—$CH_2$—, —$CH_2$—O—$CH_2$—, —$S(O)_r$—, $S(O)_r$—$CH_2$—, or —$S(O)_r$—$(CH_2)_2$— wherein r is an integer of 0 to 2, which ring may be substituted by 1 to 3 substituents selected from the group consisting of $C_{1-6}$ alkyl, $C_{2-6}$ alkenyl, $C_{2-6}$ alkynyl, $C_{3-6}$ cycloalkyl, $C_{6-14}$ aryl and $C_{7-16}$ aralkyl;

(3) a compound of the above (1) wherein the group of the formula: —$COR^1$ is carboxy which may be esterified or amidated;

(4) a compound of the above (1) wherein $R^1$ is hydroxy which may be substituted;

(5) a compound of the above (1) wherein $R^1$ is hydroxy;

(6) a compound of the above (1) wherein m is 1;

(7) a compound of the above (1) wherein Ar is a $C_{6-14}$ aryl which may be substituted by 1 to 3 substituents selected from the group consisting of halogen, $C_{1-3}$ alkylenedioxy, nitro, cyano, $C_{1-6}$ alkyl which may be halogenated, $C_{3-6}$ cycloalkyl, $C_{1-6}$ alkoxy which may be halogenated, $C_{1-6}$ alkylthio which may be halogenated, hydroxy, amino, mono-$C_{1-6}$ alkylamino, di-$C_{1-6}$ alkylamino, $C_{1-6}$ alkyl-carbonyl, carboxy, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, sulfo, $C_{1-6}$ alkylsulfonyl, $C_{6-10}$ aryl and $C_{6-10}$ aryloxy;

(8) a compound of the above (1) wherein Ar is phenyl which may be halogenated;

(9) a compound of the above (1) wherein X is a divalent group of the formula: —$Xa^1$—$Xb^1$— wherein $Xa^1$ is S, SO or $SO_2$; and $Xb^1$ is $C_{1-5}$ alkylene which may be substituted by a $C_{6-14}$ aryl which may be substituted by 1 to 3 substituents selected from the group consisting of halogen, $C_{1-3}$ alkylenedioxy, nitro, cyano, $C_{1-6}$ alkyl which may be halogenated, $C_{3-6}$ cycloalkyl, $C_{1-6}$ alkoxy which may be halogenated, $C_{1-6}$ alkylthio which may be halogenated, hydroxy, amino, mono-$C_{1-6}$ alkylamino, di-$C_{1-6}$ alkylamino, $C_{1-6}$ alkyl-carbonyl, carboxy, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, sulfol $C_{1-6}$ alkylsulfonyl, $C_{6-10}$ aryl and $C_{6-10}$ aryloxy;

(10) a compound of the above (9) wherein $Xa^1$ is S;

(11) a compound of the above (9) wherein $Xb^1$ is a $C_{1-3}$ alkylene which may be substituted by a phenyl which may be halogenated;

(12) a compound of the above (1) wherein Y is —S—;

(13) a compound of the above (1) wherein Z is —N=;

(14) a compound of the above (1) wherein ring B is a ring of the formula:

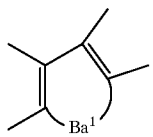

wherein $Ba^1$ is —$CH_2$—, —$(CH_2)_2$—, —O—$CH_2$— or —O—;

(15) a compound of the above (1) which is a compound of the formula:

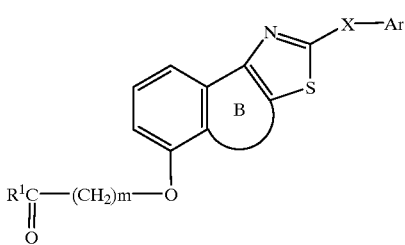

wherein the respective symbols have the same meanings as defined above;

(16) a compound of the above (15) wherein $R^1$ is hydroxy; m is 1;
Ar is phenyl which may be halogenated;
X is a divalent group of the formula: —$Xa^2$—$Xb^2$— wherein $Xa^2$ is S, SO or $SO_2$; and $Xb^2$ is a $C_{1-3}$ alkylene which may be substituted by a phenyl which may be halogenated; and
ring B is a ring of the formula:

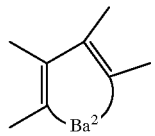

wherein $Ba^2$ is —$CH_2$—, —$(CH_2)_2$—, —O—$CH_2$— or —O—;

(17) a compound of the above (1) wherein $R^1$ is hydroxy which may be substituted by a $C_{1-6}$ alkyl;
m is an integer of 1 to 3;
Ar is $C_{6-14}$ aryl which may be substituted by 1 to 3 substituents selected from the group consisting of halogen, nitro, cyano, $C_{1-6}$ alkyl which may be halogenated, $C_{1-6}$ alkoxy and $C_{6-10}$ aryl;
X is (i) a bond or (ii) a divalent group of the formula: —$Xa^3$—$Xb^3$— wherein $Xa^3$ is a bond, S, SO, $SO_2$, O or NH; and
$Xb^3$ is a $C_{1-5}$ alkylene or $C_{2-5}$ alkenylene group which may be substituted by a phenyl which may be halogenated;
Y is —S—;
Z is —N=;
ring A is a benzene ring which may be substituted by 1 to 3 $C_{1-6}$ alkyl, in addition to a group of the formula: —$O(CH_2)_mCOR^1$; and
ring B is a ring of the formula:

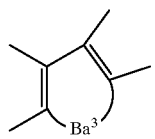

wherein $Ba^3$ is —$CH_2$—, —$(CH_2)_2$—, —O—$CH_2$— or —O—;

(18) a compound of the above (1) which is
[(2-diphenylmethylthio-4,5-dihydronaphtho[1,2-d]thiazol-6-yl)oxy]acetic acid,
[(2-(2,2-diphenylethyl)thio-4,5-dihydronaphtho[1,2-d]thiazol-6-yl)oxy]acetic acid,
[(2-diphenylmethyl)sulfonyl-4,5-dihydronaphtho[1,2-d]thiazol-6-yl)oxy]acetic acid,
[(2-bis(3-fluorophenyl)methylsulfonyl-4,5-dihydronaphto[1,2-d]thiazol-6-yl)oxy]acetic acid,
[(2-bis(2-fluorophenyl)methylsulfonyl-4,5-dihydronaphto[1,2-d]thiazol-6-yl)oxy]acetic acid, or a salt thereof;

(19) a compound of the above (1) which is
[(2-diphenylmethylthio-4,5-dihydronaphtho[1,2-d]thiazol-6-yl)oxy]acetic acid,
[(2-(2,2-diphenylethyl)thio-4,5-dihydronaphtho[1,2-d]thiazol-6-yl)oxy]acetic acid,
[(2-diphenylmethyl)sulfonyl-4,5-dihydronaphtho[1,2-d]thiazol-6-yl)oxy]acetic acid,
[(2-bis(3-fluorophenyl)methylsulfonyl-4,5-dihydronaphto[1,2-d]thiazol-6-yl)oxy]acetic acid,

[(2-bis(2-fluorophenyl)methylsulfonyl-4,5-dihydronaphto [1,2-d]thiazol-6-yl)oxy]acetic acid, or a pharmaceutically acceptable metal salt;

(20) a process for producing a compound of the above (1) which comprises
i) reacting a compound of the formula:

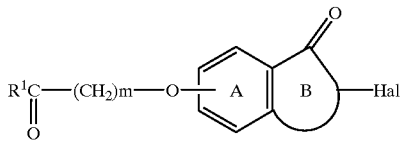

wherein Hal represents halogen; the other symbols have the same meanings as defined above, or a salt thereof with a compound of the formula:

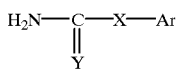

wherein the respective symbols have the same meanings as defined above, or a salt thereof, optionally followed by hydrolysis or oxidation of the resultant compound; or ii) subjecting a compound of the formula:

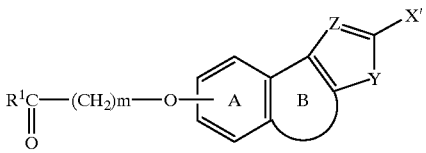

wherein X' represents SH, OH or $NH_2$; the other symbols have the same meanings as defined above, or a tautomer thereof, or a salt thereof, to alkylation, optionally followed by hydrolysis or oxidation of the resultant compound;

(21) a compound of the formula:

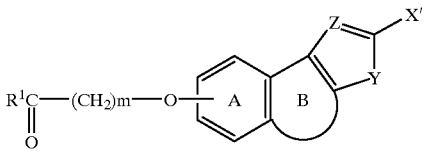

wherein X' represents SH, OH, or $NH_2$; the other symbols have the same meanings as defined above or a tautomer thereof, or a salt thereof;

(22) a pharmaceutical composition which comprises a compound of the above (1), if necessary together with a pharmaceutically acceptable carrier;

(23) a composition of the above (22) which is for eliciting a prostaglandin $I_2$ receptor agonistic effect;

(24) a composition of the above (22) which is for inhibiting a platelet aggregation;

(25) a composition of the above (22) which is for the prophylaxis or treatment of transient ischemic attack, diabetic neuropathy, peripheral vascular diseases or ulcer;

(26) a method for eliciting a prostaglandin $I_2$ receptor agonistic effect in a mammal in need thereof which comprises administering to such mammal an effective amount of a compound of the above (1) with a pharmaceutically acceptable excipient, carrier or diluent; and

(27) use of a compound of the above (1) for manufacturing a pharmaceutical composition for eliciting a prostaglandin $I_2$ receptor agonistic effect.

Referring to the above formula, the "substituent group" represented by $R^1$ includes, for example, a hydroxy which may be substituted and an amino which may be substituted.

The "substituent" for the "hydroxy which may be substituted" and for the "amino which may be substituted" includes, for example, hydrocarbon groups which may be substituted. The "amino which may be substituted" may have 1 or 2 substituent groups.

The "hydrocarbon group" of the "hydrocarbon group which may be substituted" means a monovalent group available upon elimination of one hydrogen atom from a hydrocarbon compound and includes both acyclic and cyclic hydrocarbon groups (e.g. alkyl, alkenyl, alkynyl, cycloalkyl, aryl, aralkyl, etc.). Preferred are acyclic and cyclic hydrocarbon groups containing 1 to 16 carbon atoms, such as the following.

a) $C_{1-6}$ alkyl (e.g. methyl, ethyl, propyl, isopropyl, butyl, isobutyl, sec-butyl, tert-butyl, pentyl, hexyl, etc.), b) $C_{2-6}$ alkenyl (e.g. vinyl, allyl, isopropenyl, butenyl, etc.), c) $C_{2-6}$ alkynyl (e.g. ethynyl, propargyl, butynyl, 1-hexynyl, etc.), d) $C_{3-6}$ cycloalkyl (e.g. cyclopropyl, cyclobutyl, cyclopentyl, cyclohexyl, etc.), e) $C_{6-14}$ aryl (e.g. phenyl, 1-naphthyl, 2-naphthyl, 2-anthryl, etc.), f) $C_{7-16}$ aralkyl (e.g. benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, etc.), preferably benzyl.

Among the above hydrocarbon groups, $C_{1-6}$ alkyl, $C_{6-14}$ aryl, and $C_{7-16}$ aralkyl are preferred.

The "substituent" for the "hydrocarbon group which may be substituted" includes, for example, halogen (e.g. fluorine, chlorine, bromine, iodine, etc.), $C_{1-6}$ alkyl which may be halogenated, $C_{2-6}$ alkenyl which may be halogenated, $C_{2-6}$ alkynyl which may be halogenated, $C_{3-6}$ cycloalkyl which may be halogenated, $C_{6-10}$ aryl (e.g. phenyl, naphthyl, etc.), $C_{7-11}$ aralkyl (e.g. benzyl, α-methylbenzyl, phenethyl, etc.), $C_{1-6}$ alkoxy which may be halogenated, $C_{6-10}$ aryloxy (e.g. phenoxy etc.), $C_{1-6}$ alkyl-carbonyl (e.g. acetyl, propionyl, butyryl, isobutyryl, etc.), $C_{6-10}$ aryl-carbonyl (e.g. benzoyl, naphthoyl, etc.), $C_{7-11}$ aralkyl-carbonyl (e.g. benzylcarbonyl, phenethylcarbonyl, etc.), $C_{1-6}$ alkyl-carbonyloxy (e.g. acetyloxy, propionyloxy, butyryloxy, isobutyryloxy, etc.), $C_{6-10}$ aryl-carbonyloxy (e.g. benzoyloxy, naphthoyloxy, etc.), carboxy, $C_{1-6}$ alkoxy-carbonyl (e.g. methoxycarbonyl, ethoxycarbonyl, propoxycarbonyl, isopropoxycarbonyl, butoxycarbonyl, isobutoxycarbonyl, tert-butoxycarbonyl, etc.), carbamoyl, mono-$C_{1-6}$ alkyl-carbamoyl (e.g. methylcarbamoyl, ethylcarbamoyl, etc.), di-$C_{1-6}$ alkyl-carbamoyl (e.g. dimethylcarbamoyl, diethylcarbamoyl, etc.), amidino, imino, amino, mono-$C_{1-6}$ alkylamino (e.g. methylamino, ethylamino, propylamino, isopropylamino, butylamino, etc.), di-$C_{1-6}$ alkylamino (e.g. dimethylamino, diethylamino, ethylmethylamino, dipropylamino, diisopropylamino, dibutylamino, etc.), 3- to 6-membered cyclic amino which may contain 1 to 3 hetero atoms selected from among oxygen, sulfur and nitrogen as ring members in addition to carbon and one nitrogen atom (e.g. aziridinyl, azetidinyl, pyrrolidinyl, pyrrolinyl, pyrrolyl, imidazolyl, pyrazolyl, imidazolidinyl, piperidino, morpholino, thiomorpholino, dihydropyridyl, pyridyl, N-methylpiperazinyl, N-ethylpiperazinyl, etc.), $C_{1-3}$ alkylenedioxy (e.g. methylenedioxy, ethylenedioxy, etc.), hydroxy, nitro, cyano, mercapto, sulfo, sulfino, phosphono, sulfamoyl, mono-$C_{1-6}$ alkylsulfamoyl (e.g. methylsulfamoyl, ethylsulfamoyl, propylsulfamoyl, isopropylsulfamoyl, butylsulfamoyl, etc.), di-$C_{1-6}$ alkylsulfamoyl (e.g. dimethylsulfamoyl, diethylsulfamoyl, dipropylsulfamoyl, dibutylsulfamoyl, etc.), $C_{1-6}$ alkylthio which may be halogenated, $C_{6-10}$ arylthio (e.g. phenylthio, naphthylthio, etc.), $C_{1-6}$ alkylsulfinyl (e.g. methylsulfinyl, ethylsulfinyl, propylsulfinyl, butylsulfinyl, etc.), $C_{6-10}$ arylsulfinyl (e.gi phenylsulfinyl, naphthylsulfinyl, etc.), $C_{1-6}$ alkylsulfonyl (e.g. methylsulfonyl, ethylsulfonyl, propylsulfonyl, butylsulfonyl, etc.), and $C_{6-10}$ arylsulfonyl (e.g. phenylsulfonyl, naphthylsulfonyl, etc.).

The above-mentioned "$C_{1-6}$ alkyl which may be halogenated" includes, for example, $C_{1-6}$ alkyl (e.g. methyl, ethyl, propyl, isopropyl, butyl, isobutyl, sec-butyl, tert-butyl, pentyl, hexyl, etc.) optionally having 1 to 5, preferably 1 to 3, halogen atoms (e.g. fluorine, chlorine, bromine, iodine, etc.). Specifically, mention may be made of methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc.

The "$C_{2-6}$ alkenyl which may be halogenated" includes, for example, $C_{2-6}$ alkenyl (e.g. vinyl, propenyl, isopropenyl, 2-buten-1-yl, 4-penten-1-yl, 5-hexen-1-yl, etc.) optionally having 1 to 5, preferably 1 to 3, halogen atoms (e.g. fluorine, chlorine, bromine, iodine, etc.).

The "$C_{2-6}$ alkynyl which may be halogenated" includes, for example, $C_{2-6}$ alkynyl (e.g. 2-butyn-1-yl, 4-pentyn-1-yl, 5-hexyn-1-yl, etc.) optionally having 1 to 5, preferably 1 to 3, halogen atoms (e.g. fluorine, chlorine, bromine, iodine, etc.).

The "$C_{3-6}$ cycloalkyl which may be halogenated" includes, for example, $C_{3-6}$ cycloalkyl (e.g. cyclopropyl, cyclobutyl, cyclopentyl, cyclohexyl, etc.) optionally having 1 to 5, preferably 1 to 3, halogen atoms (e.g. fluorine, chlorine, bromine, iodine, etc.). Specifically, mention may be made of cyclopropyl, cyclobutyl, cyclopentyl, cyclohexyl, 4,4-dichlorocyclohexyl, 2,2,3,3-tetrafluorocyclopentyl, 4-chlorocyclohexyl, etc.

The "$C_{1-6}$ alkoxy which may be halogenated" includes, for example, $C_{1-6}$ alkoxy optionally having 1 to 5, preferably 1 to 3, halogen atoms (e.g. fluorine, chlorine, bromine, iodine, etc.). Specifically, mention may be made of methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, etc.

The "$C_{1-6}$ alkylthio which may be halogenated" includes, for example, $C_{1-6}$ alkylthio (e.g. methylthio, ethylthio, propylthio, isopropylthio, butylthio, sec-butylthio, tert-butylthio, etc.) optionally having 1 to 5, preferably 1 to 3, halogen atoms (e.g. fluorine, chlorine, bromine, iodine, etc.). Specifically, mention may be made of methylthio, difluoromethylthio, trifluoromethylthio, ethylthio, propylthio, isopropylthio, butylthio, 4,4,4-trifluorobutylthio, pentylthio, hexylthio, etc.

The above-mentioned "hydrocarbon group" may have 1 to 5, preferably 1 to 3, substituents selected from the group consisting of the above-mentioned substituents in its substitutable position or positions and when 2 or more substitutions are involved, the substituents may be the same group or different groups.

The formula: —$COR^1$ preferably represents carboxy which may be esterified or amidated.

$R^1$ preferably represents hydroxy which may be substituted. More preferred is hydroxy.

Preferably, m is 1.

The "aromatic group" of the "aromatic group which may be substituted" as mentioned for Ar includes, for example, aromatic hydrocarbon groups and aromatic heterocyclic (heteroaromatic) groups.

The "aromatic hydrocarbon group" mentioned above includes, for example, monocyclic or fused polycyclic aromatic hydrocarbon groups having 6 to 14 carbon atoms. Specifically, $C_{6-14}$ aryl such as phenyl, 1-naphthyl, 2-naphthyl, anthryl, etc. can be mentioned. Preferred is phenyl, 1-naphthyl or 2-naphthyl. Particularly preferred is phenyl.

The "aromatic heterocyclic group" mentioned above includes, for example, 5- to 10-membered monocyclic or its fused heteroaromatic groups containing one or more, for example 1 to 4, hetero atoms selected from among nitrogen, sulfur and oxygen as a ring member other than carbon. Specifically, it includes monovalent groups available upon elimination of any one hydrogen atom each from 5- or 6-membered monocyclic heteroaromatic rings or fused ring systems consisting of any such heteroaromatic ring and 1 or 2 (preferably 1) aromatic rings (e.g. benzene ring, pyridine ring, etc.), such as thiophene, furan, pyrrole, imidazole, pyrazole, pyridine, pyrazine, pyrimidine, pyridazine, isothiazole, isoxazole, triazine, 1,2,3-oxadiazole, 1,2,3-triazole, 1,2,4-triazole, 1,3,4-thiadiazole, etc. Preferred examples of the "aromatic heterocyclic group" include 5- to 10-membered heteroaromatic groups such as 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzothienyl, benzofuranyl, 2-thienyl, 3-thienyl, 2-benzoxazolyl, 2-benzimidazolyl, 2-pyridothiazolyl, etc. More preferred are 2-pyridyl, 3-pyridyl, 4-pyridyl, 2-quinolyl, 3-quinolyl, 4-quinolyl, etc. Those heteroaromatic groups may be in the N-oxide form, where applicable.

The "substituent" for the "aromatic group which may be substituted" as mentioned for Ar includes, for example, halogen (e.g. fluorine, chlorine, bromine, iodine, etc.), $C_{1-3}$ alkylenedioxy (e.g. methylenedioxy, ethylenedioxy, etc.), nitro, cyano, $C_{1-6}$ alkyl which may be halogenated, $C_{3-6}$ cycloalkyl (e.g. cyclopropyl, cyclobutyl, cyclopentyl, cyclohexyl, etc.), $C_{1-6}$ alkoxy which may be halogenated, $C_{1-6}$ alkylthio which may be halogenated, hydroxy, amino, mono-$C_{1-6}$ alkylamino (e.g. methylamino, ethylamino, propylamino, isopropylamino, butylamino, etc.), di-$C_{1-6}$ alkylamino (e.g. dimethylamino, diethylamino, ethylmethylamino, dipropylamino, dibutylamino, etc.), $C_{1-6}$ alkyl-carbonyl (e.g. acetyl, propionyl, etc.), carboxy, $C_{1-6}$ alkoxy-carbonyl (e.g. methoxycarbonyl, ethoxycarbonyl, propoxycarbonyl, butoxycarbonyl, etc.), carbamoyl, mono-$C_{1-6}$ alkyl-carbamoyl (e.g. methylcarbamoyl, ethylcarbamoyl, etc.), di-$C_{1-6}$ alkyl-carbamoyl (e.g. dimethylcarbamoyl, diethylcarbamoyl, etc.), $C_{6-10}$ aryl-carbamoyl (e.g. phenylcarbamoyl, naphthylcarbamoyl, etc.), sulfol $C_{1-6}$ alkylsulfonyl (e.g. methylsulfonyl, ethylsulfonyl, etc.), $C_{6-10}$ aryl (e.g. phenyl, naphthyl, etc.), and $C_{6-10}$ aryloxy (e.g. phenyloxy, naphthyloxy, etc.). When the substituent is $C_{1-3}$ alkylenedioxy, it preferably forms a ring in combination with the two adjacent carbon atoms.

The above-mentioned "$C_{1-6}$ alkyl which may be halogenated", "$C_{1-6}$ alkoxy which may be halogenated", and "$C_{1-6}$ alkylthio which may be halogenated" may be the same groups as those respectively mentioned above in the definition of "the substituent" for the "hydrocarbon group which may be substituted".

The "aromatic group" of the "aromatic group which may be substituted" may have 1 to 5, preferably 1 to 3, substituents as selected from among the above-mentioned substituents in its substitutable position or positions of the aromatic ring and where two or more substitutions are involved, the substituents group may be the same group or different groups.

Preferably, Ar is $C_{6-14}$ aryl which may be substituted, etc. More preferably, Ar is phenyl which may be halogenated.

The "divalent straight-chain group which have 1 to 6 atoms and may be substituted" as mentioned for X includes, for example, divalent groups of the formula: —Xa—Xb— wherein Xa represents a bond, S, SO, SO$_2$, O, or NR$^4$; Xb represents a bond or a divalent aliphatic hydrocarbon group having 1 to 5 atoms (preferably 1 to 4 atoms) which may be substituted and may contain oxygen, nitrogen, or sulfur. In the above formula, R$^4$ represents hydrogen, $C_{1-6}$ alkyl (e.g. methyl, ethyl, propyl, isopropyl, butyl, isobutyl, pentyl, hexyl, etc.), $C_{3-6}$ cycloalkyl (e.g. cyclopropyl, cyclobutyl, cyclopentyl, etc.), $C_{6-14}$ aryl (e.g. phenyl, 1-naphthyl, 2-naphthyl, etc.), $C_{7-11}$ aralkyl (e.g. benzyl, phenethyl, etc.), formyl, $C_{1-6}$ alkyl-carbonyl (e.g. acetyl, propionyl, butyryl, isobutyryl, etc.), or $C_{6-10}$ aryl-carbonyl (e.g. benzoyl, naphthoyl, etc.), for instance.

Xa is preferably a bond, S, SO, SO$_2$, O, or NH. More preferred is S, SO, SO$_2$, O, or NH. Particularly preferred is S, SO or SO$_2$. Most preferably, Xa is S.

The "divalent aliphatic hydrocarbon group having 1 to 5 atoms which may contain sulfur, oxygen, or nitrogen" of the "divalent aliphatic hydrocarbon group having 1 to 5 atoms which may be substituted and may contain sulfur, oxygen, or nitrogen" as mentioned for Xb means a divalent aliphatic hydrocarbon group having 1 to 5 atoms which is available upon elimination of two hydrogen atoms from a saturated or an unsaturated aliphatic hydrocarbon and optionally containing 1 or 2 (preferably 1) sulfur, oxygen, or nitrogen atom between carbon atoms or in its terminal position.

Specifically, the examples include
(i) $C_{1-5}$ alkylene (e.g. —CH$_2$—, —(CH$_2$)$_2$—, —(CH$_2$)$_3$—, —(CH$_2$)$_4$—, —(CH$_2$)$_5$—, etc.)
(ii) $C_{2-5}$ alkenylene (e.g. —CH=CH—, —CH$_2$—CH=CH—, —CH$_2$—CH=CH—CH$_2$—, —CH$_2$—CH$_2$—CH=CH—, —CH=CH—CH$_2$—CH$_2$—, etc.)
(iii) $C_{2-5}$ alkynylene (e.g. —C≡C—, —CH$_2$—C≡C—, —CH$_2$—C≡C—CH$_2$—, etc.)
(iv) groups of the formula: —(CH$_2$)$_p$—Xc—(CH$_2$)$_q$— wherein Xc represents S, SO, SO$_2$, O, or NR$^{4a}$; p and q independently represent an integer of 0 to 4 and p+q is an integer of 0 to 4. R$^{4a}$ in this formula includes the same groups as those mentioned for R$^4$.

The above-mentioned "divalent aliphatic hydrocarbon group having 1 to 5 atoms which may contain sulfur, oxygen, or nitrogen" is preferably $C_{1-5}$ alkylene or $C_{2-5}$ alkenylene. Particularly preferred is methylene.

The "substituent" for the "divalent straight-chain group which have 1 to 6 atoms and may be substituted" or for the "divalent aliphatic hydrocarbon group having 1 to 5 atoms which may be substituted and may contain sulfur, oxygen, or nitrogen" includes, for example, halogen (e.g. fluorine, chlorine, bromine, iodine, etc.), nitro, cyano, $C_{1-6}$ alkyl which may be halogenated, $C_{3-6}$ cycloalkyl (e.g. cyclopropyl, cyclobutyl, cyclopentyl, cyclohexyl, etc.), $C_{7-11}$ aralkyl (e.g. benzyl, phenethyl, etc.), $C_{1-6}$ alkoxy which may be halogenated, $C_{1-6}$ alkylthio which may be halogenated, hydroxy, amino, mono-$C_{1-6}$ alkylamino (e.g. methylamino, ethylamino, propylamino, isopropylamino, butylamino, etc.), di-$C_{1-6}$ alkylamino (e.g. dimethylamino, diethylamino, ethylmethylamino, dipropylamino, dibutylamino, etc.), $C_{6-10}$ aryloxy (e.g. phenyloxy, naphthyloxy, etc.), $C_{1-6}$ alkyl-carbonyl (e.g. acetyl, propionyl, butyryl, isobutyryl, etc.), $C_{6-10}$ aryl-carbonyl (e.g. benzoyl, naphthoyl, etc.), oxo, and aromatic groups which may be substituted.

The above-mentioned "$C_{1-6}$ alkyl which may be halogenated", "$C_{1-6}$ alkoxy which may be halogenated", and "$C_{1-6}$ alkylthio which may be halogenated" include those specific groups as respectively mentioned as the substituent for the "hydrocarbon group which may be substituted".

The above-mentioned "aromatic group which may be substituted" includes the same groups as those mentioned for the "aromatic group which may be substituted" for Ar.

Among those substituents, halogen, hydroxy, and an aromatic group which may be substituted are preferred. Particularly preferred is $C_{6-14}$ aryl.

Those substituents may occur in 1 to 5, preferably 1 to 3, substitutable positions and where two or more substitutions are involved, the substituents may be the same group or different groups.

Xb is preferably (i) a bond, (ii) $C_{1-5}$ alkylene which may be substituted by 1 to 3 substituents selected from the group consisting of halogen, hydroxy and an aromatic group which may be substituted, or (iii) $C_{2-5}$ alkenylene which may be substituted by 1 to 3 substituents selected from the group consisting of halogen, hydroxy and an aromatic group which may be substituted. Preferred examples of the above "aromatic group which may be substituted" are $C_{6-14}$ aryl or 5- to 10-membered aromatic heterocyclic group each containing 1 to 4 hetero atoms selected from among nitrogen, sulfur, and oxygen as ring members in addition to carbon, each of which may be substituted by 1 to 3 substituents selected from the group consisting of halogen, $C_{1-6}$ alkyl, $C_{1-6}$ alkoxy and hydroxy.

It is also preferable that this "aromatic group which may be substituted" be present on the carbon atom in the terminal position where Ar is attached.

More preferably, Xb is (i) a bond or (ii) a $C_{1-5}$ alkylene which may be substituted by an aromatic group (preferably $C_{6-14}$ aryl) which may be substituted. Particularly preferred is a $C_{1-5}$ alkylene which may be substituted by a $C_{6-14}$ aryl which may be substituted. Most preferred is a $C_{1-3}$ alkylene which may be substituted by a phenyl which may be halogenated.

X is preferably a divalent group of the formula: —Xa$^1$—Xb$^1$— wherein Xa$^1$ is S, SO or SO$_2$; and Xb$^1$ is $C_{1-5}$ alkylene which may be substituted by a $C_{6-14}$ aryl which may be substituted by 1 to 3 substituents selected from the group consisting of halogen, $C_{1-3}$ alkylenedioxy, nitro, cyano, $C_{1-6}$ alkyl which may be halogenated, $C_{3-6}$ cycloalkyl, $C_{1-6}$ alkoxy which may be halogenated, $C_{1-6}$ alkylthio which may be halogenated, hydroxy, amino, mono-$C_{1-6}$ alkylamino, di-$C_{1-6}$ alkylamino, $C_{1-6}$ alkyl-carbonyl, carboxy, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, sulfo, $C_{1-6}$ alkylsulfonyl, $C_{6-10}$ aryl and $C_{6-10}$ aryloxy. $Xa^1$ is preferably S. $Xb^1$ is preferably $C_{1-3}$ alkylene which may be substituted by a phenyl which may be halogenated.

$R^2$ in —N($R^2$)— for Y represents hydrogen or a substituent group and this "substituent group" may for example be a hydrocarbon group or an acyl.

The above-mentioned "hydrocarbon group" includes the same hydrocarbon group as the "hydrocarbon group" of the "hydrocarbon group which may be substituted".

The above-mentioned "acyl" may for example be an acyl derived from a carboxylic acid or a sulfonic acid. Preferred examples are formyl, $C_{1-6}$ alkyl-carbonyl (e.g. acetyl, propionyl, butyryl, isobutyryl, etc.), $C_{6-10}$ aryl-carbonyl (e.g. benzoyl, naphthoyl, etc.), $C_{7-11}$ aralkyl-carbonyl (e.g. benzylcarbonyl, phenethylcarbonyl, naphthylmethylcarbonyl, etc.), $C_{1-6}$ alkylsulfonyl (e.g. mesyl, ethylsulfonyl, propylsulfonyl, etc.), $C_{6-10}$ arylsulfonyl which may be substituted, and $C_{7-11}$, aralkylsulfonyl (e.g. benzylsulfonyl, phenethylsulfonyl, naphthylmethylsulfonyl, etc.).

The "$C_{6-10}$ arylsulfonyl" of the above-mentioned "$C_{6-10}$ arylsulfonyl which may be substituted" includes, for example, phenylsulfonyl and naphthylsulfonyl. The "substituent" for this "$C_{6-10}$ arylsulfonyl which may be substituted" includes, for example, $C_{1-6}$ alkyl (e.g. methyl, ethyl, propyl, isopropyl, butyl, isobutyl, pentyl, hexyl, etc.), $C_{1-6}$ alkoxy (e.g. methoxy, ethoxy, propoxy, butoxy, etc.), and nitro. The "$C_{6-10}$ arylsulfonylfl of the "$C_{6-10}$ arylsulfonyl which may be substituted" may have 1 to 3 substituents selected from among the substituents mentioned above and where two or more substituents are present, they may be the same group or different groups. Specific examples are tosyl and m-nitrobenzenesulfonyl.

$R^2$ is preferably hydrogen.

Y is preferably —S—, —O—, or —NH—. More preferred is —S—.

$R^3$ in —C($R^3$)= for Z represents hydrogen or a hydrocarbon group. The "hydrocarbon group" includes the same hydrocarbon group as the "hydrocarbon group" of the "hydrocarbon group which may be substituted".

$R^3$ is preferably hydrogen.

Z is preferably —N=.

The "substituent" for the "benzene ring which may be substituted by a substituent, in addition to a group of the formula: —O(CH$_2$)$_m$COR$^1$ (wherein the respective symbols have the same meanings as defined above)" as mentioned for ring A may number 1 to 3 and includes the same groups as the substituents mentioned for the "aromatic group which may be substituted" for Ar. Where two or more substitutions are involved, the substituents may be the same group or different groups.

The "5- to 7-membered ring" of the "5- to 7-membered ring which may be substituted" as mentioned for ring B is a 5- to 7-membered carbocyclic ring or a 5- to 7-membered heterocyclic ring which may contain 1 to 3 hetero atoms selected from among oxygen, sulfur, and nitrogen (preferably one hetero atom selected from the group consisting of oxygen and sulfur) as ring members in addition to carbon. Among preferred examples of the "5- to 7-membered ring" are 5- to 7-membered rings of the formula:

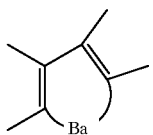

wherein Ba represents —CH$_2$—, —(CH$_2$)$_2$—, —(CH$_2$)$_3$—, —CH=CH—, —O—, —O—CH$_2$—, —CH$_2$—O—, —CH$_2$—CH$_2$—, —CH$_2$—O—CH$_2$—, —S(O)$_r$—, —S(O)$_r$—CH$_2$—, or —S(O)$_r$—(CH$_2$)$_2$— wherein r represents an integer of 0 to 2.

Preferably, Ba is —CH$_2$—, —(CH$_2$)$_2$—, —O—CH$_2$— or —O—.

The "substituent" for the above-mentioned "5 to 7-membered ring" may for example be a hydrocarbon group. This "hydrocarbon group" includes the same hydrocarbon group as mentioned for the "hydrocarbon group" of the "hydrocarbon group which may be substituted".

This "5- to 7-membered ring" may have 1 to 3 substituents selected from among the above-mentioned substituents in substitutable positions and where two or more substitutions are involved, the substituents may be the same group or different groups.

Among the compounds of formula (I), preferred is the compound of the following formula or a salt thereof.

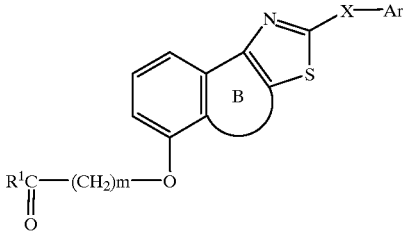

wherein the respective symbols have the same meanings as defined above. More preferred is the compound, inclusive of its salt, wherein $R^1$ is hydroxy; m is 1;

Ar is phenyl which may be halogenated;

X is a divalent group of the formula: —Xa$^2$—Xb$^2$— wherein Xa$^2$ is S, SO or SO$_2$; and Xb$^2$ is $C_{1-3}$ alkylene which may be substituted by a phenyl which may be halogenated; and ring B is a ring of the formula:

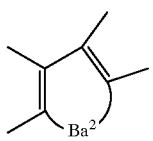

wherein Ba$^2$ is —CH$_2$—, —(CH$_2$)$_2$—, —O—CH$_2$— or —O—.

In compound (I), preferred is a compound wherein $R^1$ is hydroxy which may be substituted by a $C_{1-6}$ alkyl;

m is an integer of 1 to 3;

Ar is $C_{6-14}$ aryl which may be substituted by 1 to 3 substituents selected from the group consisting of halogen, nitro, cyano, $C_{1-6}$ alkyl which may be halogenated, $C_{1-6}$ alkoxy and $C_{6-10}$ aryl;

X is (i) a bond or (ii) a divalent group of the formula: —Xa$^3$—Xb$^3$— wherein Xa$^3$ is a bond, S, SO, SO$_2$, O or NH; and $Xb^3$ is a $C_{1-5}$ alkylene or $C_{2-5}$ alkenylene group which may be substituted by a phenyl which may be halogenated;

Y is —S—;

Z is —N=;

ring A is a benzene ring which may be substituted by 1 to 3 $C_{1-6}$ alkyl, in addition to a group of the formula: —O(CH$_2$)$_m$COR$^1$; and ring B is a ring of the formula:

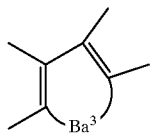

wherein $Ba^3$ is —CH$_2$—, —(CH$_2$)$_2$—, —O—CH$_2$— or —O—.

The preferred species of compound (I) of the invention include:

[(2-diphenylmethylthio-4,5-dihydronaphtho[1,2-d]thiazol-6-yl)oxy]acetic acid,

[(2-(2,2-diphenylethyl)thio-4,5-dihydronaphtho[1,2-d]thiazol-6-yl)oxy]acetic acid,

[(2-diphenylmethyl)sulfonyl-4,5-dihydronaphtho[1,2-d]thiazol-6-yl)oxy]acetic acid,

[(2-bis(3-fluorophenyl)methylsulfonyl-4,5-dihydronaphto[1,2-d]thiazol-6-yl)oxy]acetic acid,

[(2-bis(2-fluorophenyl)methylsulfonyl-4,5-dihydronaphto[1,2-d]thiazol-6-yl)oxy]acetic acid, and a salt thereof. As the salt, a pharmaceutically acceptable metal salt is preferred.

Depending on the kinds if substituents it possesses, compound (I) gives rise to stereoisomers. Such stereoisomers and mixtures thereof also fall within the scope of the invention.

The salt of compound (I) according to the present invention typically includes various pharmacologically acceptable salts. Examples of the salt include salts with inorganic bases, ammonium salts, salts with organic bases, salts with inorganic acids, salts with organic acids, and salts with basic or acidic amino acids. The preferred salt with an inorganic base includes, for example, alkali metal salts such as sodium salt, potassium salt, etc., alkaline earth metal salts such as calcium salt, magnesium salt, etc., and aluminum salt. The preferred salt with an organic base includes, for example, salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, etc. The preferred salt with an inorganic acid includes, for example, salts with hydrochloric acid, hydrobromic acid, nitric acid, sulfuric acid, phosphoric acid, etc. The preferred salt with an organic acid includes, for example, salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, etc. The preferred salt with a basic amino acid includes, for example, salts with arginine, lysine, ornithine, etc. The preferred salt with an acidic amino acid includes, for example, salts with aspartic acid, glutamic acid, etc.

Particularly preferred are pharmaceutically acceptable salts. For example, when the compound (I) contains a basic functional group, the preferred salt includes, for example, salts with such inorganic acids as hydrochloric acid, hydrobromic acid, nitric acid, sulfuric acid, phosphoric acid, etc. and salts with such organic acids as acetic acid, phthalic acid, fumaric acid, oxalic acid, tartaric acid, maleic acid, citric acid, succinic acid, methanesulfonic acid, p-toluenesulfonic acid, etc. When an acidic functional group is present, for example, alkali metal salts such as sodium salt and potassium salt, etc., alkaline earth metal salts such as calcium salt and magnesium salt, and ammonium salts are preferred.

The process for producing the compound (I) of the invention is now described.

Compound (I) of the invention can be produced by the per se known processes or by any processes analogous thereto, for example in accordance with the following reaction schemes (Reaction scheme 1 and Reaction scheme 2). The symbols used for the respective compounds in those schemes have the same meanings as defined above. Compounds (II) to (XIV) in the reaction schemes include their salts. The salts may for example be of the same kind as the salt of compound (I).

Reaction scheme 1

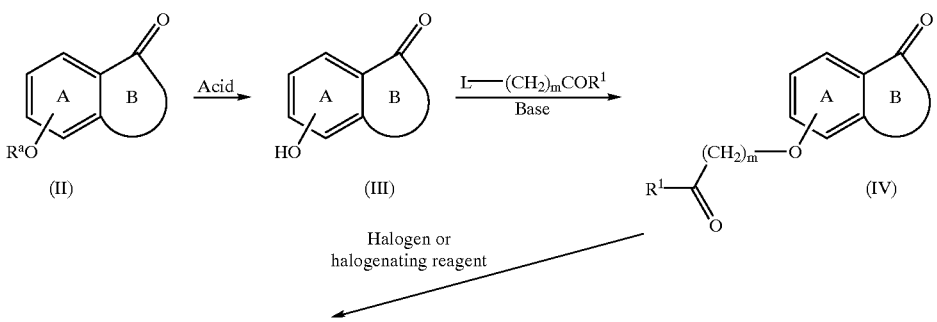

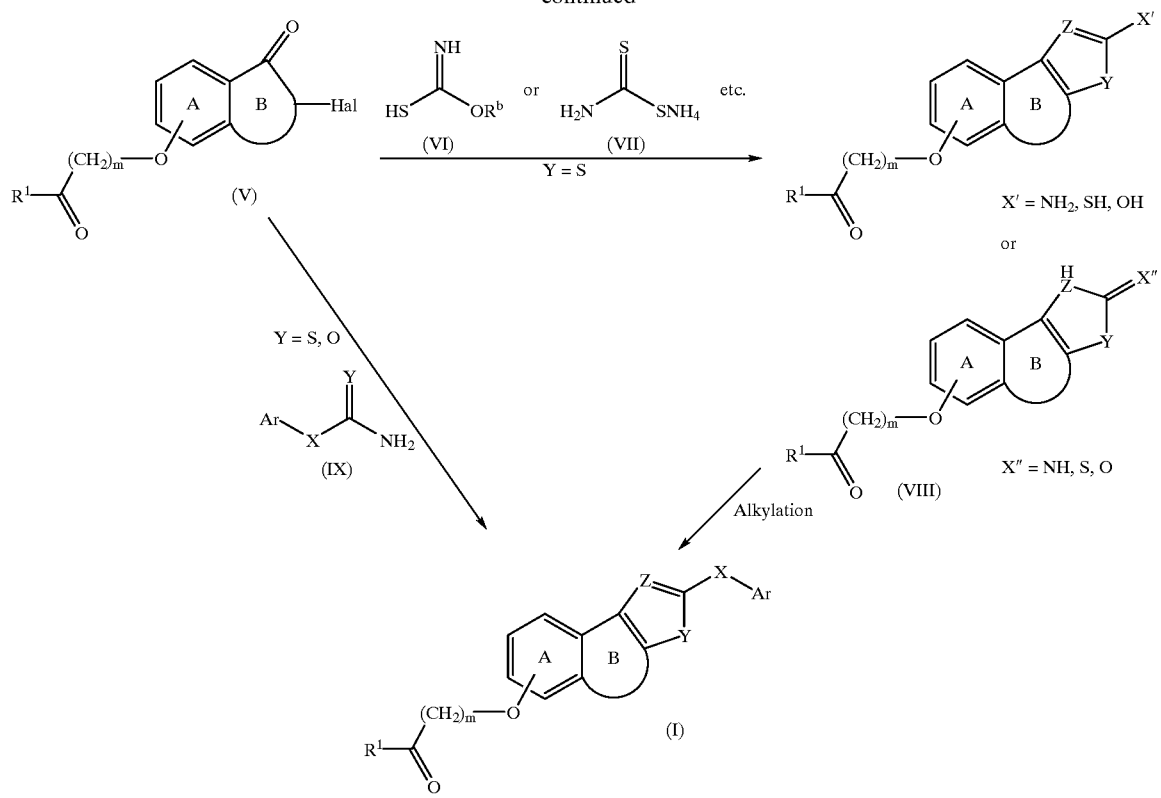

Compound (II) wherein $R^a$ represents a hydrocarbon group; the other symbols have the same meanings as defined above, can be produced by the per se known method, for example the process described in Berichte deutschen chemischen Gesellschaft 58B, 1947 (1925), or by any process analogous thereto.

The "hydrocarbon group" mentioned for $R^a$ includes the same hydrocarbon group as those mentioned for the "hydrocarbon group".

Compound (VI) wherein $R^b$ represents a hydrocarbon group, can be produced by the per se known method, for example the process described in Journal of the Chemical Society, 1434 (1951), or by any process analogous thereto.

The "hydrocarbon group" mentioned for $R^b$ includes the same hydrocarbon group as those mentioned above for the "hydrocarbon group".

Compound (VII) can be produced by the per se known method, for example the process described in Organic Syntheses, 27, 73 (1947), or by any process analogous thereto.

Compound (IX) may be purchased from a commercial source if it is available on the market or can be produced by the per se known method, for example the process described in Shin Jikken Kagaku Koza (New Series in Experimental Chemistry) 14, III, 1628–1644 (1978).

Compound (III) can be produced by hydrolyzing compound (II) using an acid catalyst. The acid catalyst includes, for example, mineral acids such as hydrochloric acid, hydrobromic acid, sulfuric acid, etc., silicon compounds such as trimethylsilyl iodide (Me$_3$SiI), trimethylsilyl chloride (Me$_3$SiCl), etc., and Lewis acids such as aluminum chloride, boron tribromide, etc. If necessary, an additive as ethanedithiol or sodium iodide may be used in combination with a Lewis acid. The amount of the acid catalyst, taking a mineral acid as an example, is generally about 1 to 100 moles, preferably about 10 to 50 moles, per mole of compound (II), and when a silicon compound or a Lewis acid is used, is generally about 1 to 20 moles, preferably about 1 to 5 moles, per mole of compound (II). The amount of the additive used in combination with a Lewis acid is generally about 0.1 to 20 moles, preferably about 1 to 10 moles, per mole of compound (II).

This reaction can be advantageously carried out in the absence of a solvent or in the presence of a solvent indifferent to the reaction (hereinafter referred to as an inert solvent). There is no particular limitation on the inert solvent that can be used unless the progress of the reaction is interfered with. When a mineral acid is used, for instance, the solvent is preferably water or mixtures of water with organic solvents, for example, alcohols such as methanol, ethanol, propanol, etc., saturated hydrocarbons such as cyclohexane, hexane, etc., aromatic hydrocarbons such as benzene, toluene, xylene, etc., ethers such as tetrahydrofuran, dioxane, 1,2-dimethoxyethane, diethyl ether, diisopropyl ether, etc., amides such as N,N-dimethylformamide, N,N-dimethylacetamide, hexamethylphosphoric triamide, etc., sulfoxides such as dimethyl sulfoxide etc., and halogenated hydrocarbons such as dichloromethane, chloroform, carbon tetrachloride, 1,2-dichloroethane, etc.

When a silicon compound or a Lewis acid is used, the solvent is preferably saturated hydrocarbons such as cyclohexane, hexane, etc., aromatic hydrocarbons such as benzene, toluene, xylene, etc., ethers such as tetrahydrofuran, dioxane, 1,2-dimethoxyethane, diethyl ether, diisopropyl ether, etc., amides such as N,N-dimethylformamide, N,N-dimethylacetamide, hexamethylphosphoric triamide, etc., sulfoxides such as dimethyl sulfoxide etc., halogenated hydrocarbons such as dichloromethane, chloroform, carbon tetrachloride, 1,2-dichloroethane, etc., and mixtures of these solvents.

The reaction time is generally 30 minutes to 24 hours, preferably 30 minutes to 6 hours. The reaction temperature is generally −78° C. to 200° C., preferably −20° C. to 150° C.

The reaction product can be used, either as the reaction mixture as such or in a partially purified form, in the next reaction. However, the product compound can be isolated from the reaction mixture in the routine manner and expediently purified by the conventional purification procedure (e.g. recrystallization, distillation, chromatography; etc.).

Compound (IV) can be produced by reacting compound (III) with a compound of the formula: L—$(CH_2)_m$COR$^1$ wherein L represents a leaving group; R$^1$ is as defined above, and a salt thereof.

The "leaving group" for L includes, for example, halogen (e.g. fluorine, chlorine, bromine, iodine, etc.), $C_{1-6}$ alkylsulfonyloxy (e.g. methanesulfonyloxy, ethanesulfonyloxy, etc.), and $C_{6-10}$ arylsulfonyloxy which may be substituted. The "$C_{6-10}$ arylsulfonyloxy which may be substituted" includes, for example, $C_{6-10}$ arylsulfonyloxy (e.g. phenylsulfonyloxy, naphthylsulfonyloxy, etc.) which may be substituted by 1 to 3 substituents selected from the group consisting of $C_{1-6}$ alkyl, $C_{1-6}$ alkoxy and nitro. Specifically, it includes m-nitrobenzenesulfonyloxy and p-toluenesulfonyloxy, among others.

The base includes, for example, inorganic bases, e.g. alkali metal hydroxides such as sodium hydroxide, potassium hydroxide, etc., alkali metal alkoxides such as sodium methoxide, sodium ethoxide, potassium tert-butoxide, etc., alkali metal hydrides such as sodium hydride, potassium hydride, etc., metal amides such as sodium amide, lithium diisopropylamide, lithium hexamethyldisilazide, etc., and basic salts such as potassium hydrogen carbonate, sodium carbonate, potassium carbonate, sodium acetate, etc. The amount of the base is generally about 0.5 to 5 moles, preferably about 1 to 3 moles, per mole of compound (III).

The proportion of the compound of the formula: L—$(CH_2)_m$COR' wherein the respective symbols have same meanings as defined above, is about 0.8 to 2 moles, preferably about 1 to 1.5 moles, per mole of compound (III).

This reaction can be carried out with advantage in an inert solvent. Among such solvents are alcohols such as methanol, ethanol, propanol, etc., saturated hydrocarbons such as cyclohexane, hexane, etc., aromatic hydrocarbons such as benzene, toluene, xylene, etc., ethers such as tetrahydrofuran, dioxane, 1,2-dimethoxyethane, diethyl ether, diisopropyl ether, etc., amides such as N,N-dimethylformamide, N,N-dimethylacetamide, hexamethylphosphoric triamide, etc., sulfoxides such as dimethyl sulfoxide etc., halogenated hydrocarbons such as dichloromethane, chloroform, carbon tetrachloride, 1,2-dichloroethane, etc., ketones such as acetone, methyl ethyl ketone, etc., water, and mixtures of these solvents.

The reaction time is generally 10 minutes to 8 hours, preferably 30 minutes to 3 hours. The reaction temperature is generally 0° C. to 120° C., preferably 25° C. to 100° C.

The reaction product can be directly used, either as the reaction mixture as such or in a partially purified form, in the next reaction. If desired, however, the product compound can be isolated from the reaction mixture in the routine manner and expediently purified by the conventional purification procedure (e.g. recrystallization, distillation, chromatography, etc.).

Where R$^1$ in compound (IV) is hydroxy, the compound can be obtained by esterification or ester-exchange reaction in the per se known method using an acid as a catalyst, if desired.

For example, the compound (IV) wherein R$^1$ is hydroxy may be reacted with the corresponding alcohol or ester using an acid as a catalyst. The corresponding alcohol mentioned above includes a compound of the formula: R$^{1a}$—OH wherein R$^{1a}$ represents the "substituent" of the "hydroxy group which may be substituted" for above R$^1$. The corresponding ester includes a compound of the formula: R—COOR$^{1b}$ wherein R represents a hydrocarbon group; and R$^{1b}$ has same meanings as mentioned for R$^{1a}$.

The "hydrocarbon group" mentioned for R includes the same hydrocarbon group as those mentioned for the "hydrocarbon group".

The amount of the corresponding alcohol or ester to be used is about 10 to 1,000 moles per mole of compound (IV).

While the above alcohol or ester is generally expected to serve as the solvent as well, other solvents, for example saturated hydrocarbons such as cyclohexane, hexane, etc., aromatic hydrocarbons such as benzene, toluene, xylene, etc., ethers such as tetrahydrofuran, dioxane, 1,2-dimethoxyethane, diethyl ether, diisopropyl ether, etc., amides such as N,N-dimethylformamide, N,N-dimethylacetamide, hexamethylphosphoric triamide, etc., sulfoxides such as dimethyl sulfoxide etc., halogenated hydrocarbons such as dichloromethane, chloroform, carbon tetrachloride, 1,2-dichloroethane, etc., and mixtures of these solvents can be optionally employed.

The acid catalyst mentioned above includes, for example, mineral acids such as hydrochloric acid, hydrobromic acid, sulfuric acid, etc., sulfonic acids such as p-toluenesulfonic acid, methanesulfonic acid, etc., and Lewis acids such as boron trifluoride ether complexes. The amount of the acid catalyst to be used is about 0.01 to 2 moles, preferably about 0.1 to 1 mole, per mole of compound (IV).

The reaction time is generally 15 minutes to 24 hours, preferably 30 minutes to 6 hours. The reaction temperature is generally −10° C. to 150° C., preferably 50° C. to 120° C.

The compound (IV) wherein R$^1$ is hydroxy may be reacted with a halogenating 4gent (e.g. thionyl chloride, phosphorus oxychloride, etc.) to give the acid halide (chloride) which can then be reacted with the corresponding alcohol. The corresponding alcohol includes a compound of the formula: R$^{1a}$—OH wherein R$^{1a}$ has same meanings as mentioned above. The proportion of the halogenating agent is generally about 1 to 50 moles, preferably about 1 to 10 moles, per mole of. compound (IV). The proportion of the corresponding alcohol is generally about 1 to 5 moles, preferably about 1 to 2 moles, per mole of compound (IV).

This reaction can be carried out with advantage in the absence of a solvent or in the presence of an inert solvent. There is no particular limitation on the kind of inert solvent unless the progress of the reaction is interferred with. The inert solvent includes, for example, esters such as methyl acetate, ethyl acetate, amyl acetate, etc., saturated hydrocarbons such as cyclohexane, hexane, etc., aromatic hydrocarbons such as benzene, toluene, xylene, etc., ethers such as tetrahydrofuran, dioxane, 1,2-dimethoxyethane, diethyl ether, diisopropyl ether, etc., amides such as N,N-dimethylformamide, N,N-dimethylacetamide, hexamethylphosphoric triamide, etc., sulfoxides such as dimethyl sulfoxide etc., halogenated hydrocarbons such as dichloromethane, chloroform, carbon tetrachloride, 1,2-dichloroethane, etc., and mixtures of these solvents.

The reaction time is generally 30 minutes to 6 hours, preferably 30 minutes to 2 hours. The reaction temperature is generally −10° C. to 150° C., preferably 0° C. to 100° C.

The reaction product can be directly used, either as the reaction mixture as such or in a partially purified form, in the next reaction. If desired, however, the product compound can be isolated from the reaction mixture in the routine manner and expediently purified by the conventional purification procedure (e.g. recrystallization, distillation, chromatography, etc.).

Compound (V) can be produced by reacting compound (IV) with a copper (II) halide (e.g. copper (II) bromide). The proportion of the copper halide is generally about 1 to 3 moles, preferably about 1.5 to 2 moles, per mole of compound (V).

This reaction can be carried out with advantage in an inert solvent. There is no particular limitation on the kind of inert solvent unless the progress of the reaction is interferred with. The inert solvent includes, for example, esters such as methyl acetate, ethyl acetate, amyl acetate, etc., saturated hydrocarbons such as cyclohexane, hexane, etc., aromatic hydrocarbons such as benzene, toluene, xylene, etc., ethers such as tetrahydrofuran, dioxane, 1,2-dimethoxyethane, diethyl ether, diisopropyl ether, etc., amides such as N,N-dimethylformamide, N,N-dimethylacetamide, hexamethylphosphoric triamide, etc., sulfoxides such as dimethyl sulfoxide etc., halogenated hydrocarbons such as dichloromethane, chloroform, carbon tetrachloride, 1,2-dichloroethane, etc., and mixtures of these solvents.

The reaction time varies with the species of reagent and solvent used but is generally 1 to 24 hours, preferably 1 to 14 hours. The reaction temperature is generally 0° C. to 150° C., preferably 20° C. to 100° C.

If desired, compound (V) can also be produced by reacting compound (IV) with a halogen (e.g. bromine, etc.) or a halogenating reagent (e.g. pyridinum hydrobromide perbromide, etc.) optionally in the presence of a base. The proportion of the halogen or the halogenating reagent per mole of compound (IV) is about 1 to 2 moles and preferably about 1 to 1.1 moles. The base that can be used for this purpose includes, for example, inorganic bases, e.g. alkali metal hydroxides such as sodium hydroxide, potassium hydroxide, etc. and ammonia, organic bases such as triethylamine, pyridine, etc., and basic salts such as potassium hydrogen carbonate, sodium carbonate, potassium carbonate, sodium acetate, etc. The proportion of the base per mole of compound (V) is generally about 0.1 to 5 moles and preferably about 1 to 2 moles.

This reaction can be advantageously carried out in an inert solvent. The solvent is not so critical in kind unless the progress of the reaction is interfered with. The inert solvent includes, for example, alcohols such as methanol, ethanol, propanol, etc., saturated hydrocarbons such as cyclohexane, hexane, etc., organic acids such as formic acid, acetic acid, etc., ethers such as tetrahydrofuran, dioxane, 1,2-dimethoxyethane, diethyl ether, diisopropyl ether, etc., halogenated hydrocarbons such as dichloromethane, chloroform, carbon tetrachloride, 1,2-dichloroethane, etc., and mixtures of these solvents.

The reaction time is generally 5 minutes to 5 hours, preferably 10 minutes to 1 hour. The reaction temperature is generally −10° C. to 100° C., preferably 0° C. to 60° C.

The reaction product can be directly used, either as the reaction mixture as such or in a partially purified form, in the next reaction. If desired, however, the product compound can be isolated from the reaction mixture in the routine manner and expediently purified by the conventional purification procedure (e.g. recrystallization, distillation, chromatography, etc.).

Compound (VIII) can be produced by reacting compound (V) with compound (VI) or compound (VII) optionally in the presence of a base or an acid: The amount of compound (VI) or compound (VII) per mole of compound (V) is generally about 1 to 1.5 moles and preferably about 1 to 1.2 moles. The base that can be used includes inorganic bases such as alkali metal hydroxides, e.g. sodium hydroxide, potassium hydroxide, etc., ammonia, etc., organic bases such as triethylamine, pyridine, etc., and basic salts such as potassium hydrogen carbonate, sodium carbonate, potassium carbonate, sodium acetate, etc. The acid that can be used includes carboxylic acids such as acetic acid, trifluoroacetic acid, propionic acid, etc. The amount of the base or the acid is generally about 0.1 to 5 moles, preferably about 1 to 2 moles, per mole of compound (V).

This reaction can be conducted with advantage in an inert solvent. The solvent is not so critical in kind unless the progress of the reaction is interfered with. The preferred inert solvent includes, for example, alcohols such as methanol, ethanol, propanol, etc., ketones such as acetone, methyl ethyl ketone, etc., nitrites such as acetonitrile etc., amides such as N,N-dimethylformamide, N,N-dimethylacetamide, hexamethylphosphoric triamide, etc., carboxylic acid such as acetic acid, etc., water, and mixtures of these solvents.

The reaction time varies with the species of reactants and solvent used but is generally 30 minutes to 24 hours, preferably 30 minutes to 14 hours. The reaction temperature is generally 0° C. to 150° C. and preferably 30° C. to 100° C.

The reaction product can be directly used, either as the reaction mixture as such or in a partially purified form, in the next reaction. If desired, however, the product compound can be isolated from the reaction mixture in the routine manner and expediently purified by the conventional purification procedure (e.g. recrystallization, distillation, chromatography, etc.).

Compound (I) can be produced by reacting compound (V) with compound (IX) optionally in the presence of an acid or a base. The proportion of compound (IX) per mole of compound (V) is generally about 0.8 to 3 moles and preferably 1 to 1.3 moles. The acid that can be used includes, for example, mineral acids such as hydrochloric acid, hydrobromic acid, sulfuric acid, etc. The base that can be used includes, for example, inorganic bases such as alkali metal hydroxides, e.g. sodium hydroxide, potassium hydroxide, etc., ammonia, etc., organic bases such as triethylamine, pyridine, etc., and basic salts such as potassium hydrogen carbonate, sodium carbonate, potassium carbonate, sodium acetate, etc. The amount of the acid or base is about 1 to 1.5 moles, preferably about 1 to 1.3 moles, per mole of compound (V).

This reaction is conducted with advantage in an inert solvent. The inert solvent that can be used includes, for example, amides such as N,N-dimethylformamide, N,N-dimethylacetamide, hexamethylphosphoric triamide, etc., nitrites such as acetonitrile etc., ketones such as acetone, methyl ethyl ketone, etc., alcohols such as methanol, ethanol, propanol, etc., ethers such as tetrahydrofuran, dioxane, 1,2-dimethoxyethane, diethyl ether, diisopropyl ether, etc., halogenated hydrocarbons such as dichloromethane, chloroform, carbon tetrachloride, 1,2-dichloroethane, etc., trifluoroacetic anhydride, water, and mixtures of these solvents.

The reaction time is generally 30 minutes to 48 hours, preferably 1 to 24 hours. The reaction temperature is generally 0° C. to 150° C., preferably 25° C. to 100° C.

Alternatively, compound (I) can be produced by subjecting the X' moiety of compound (VIII) to alkylation optionally in the presence of a base. Compound (VIII) may be its tautomer. The tautomer may be a compound of the formula:

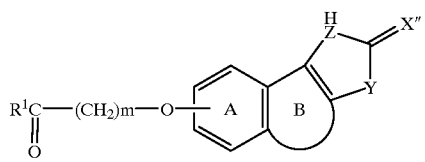

wherein X" represents S, O, or NH; the other symbols have the same meanings as defined above.

The alkylation can be carried out in the per se known method. The alkylating agent may for example be a compound of the formula: Ar—Xb—L wherein the respective symbols have the same meanings as defined above. The proportion of the alkylating agent is generally about 0.8 to 5 moles, preferably 1 to 2 moles, per mole of compound (VIII).

The base that can be used includes, for example, inorganic bases such as alkali metal hydroxides, e.g. sodium hydroxide, potassium hydroxide, etc., organic bases such as triethylamine, pyridine, etc., alkali metal alkoxides such as sodium methoxide, sodium ethoxide, potassium tert-butoxide, etc., alkali metal hydrides such as sodium hydride, potassium hydride, etc., metal amides such as sodium amide, lithium diisopropylamide, lithium hexamethyldisilazide, etc., and basic salts such as potassium hydrogen carbonate, sodium carbonate, potassium carbonate, sodium acetate, etc. The proportion of the base is about 1 to 5 moles, preferably about 1 to 1.3 moles, per mole of compound (VIII).

This reaction can be carried out with advantage in an inert solvent. The solvent is not so critical in kind unless the progress of the reaction is interfered with. The preferred inert solvent includes, for example, amides such as N,N-dimethylformamide, N,N-dimethylacetamide, hexamethylphosphoric triamide, etc., nitrites such as acetonitrile etc., ketones such as acetone, methyl ethyl ketone, etc., ethers such as tetrahydrofuran, dioxane, 1,2-dimethoxyethane, diethyl ether, diisopropyl ether, etc., and mixtures of these solvents.

The reaction time is generally 30 minutes to 12 hours, preferably 1 to 12 hours. The reaction temperature is generally 0° C. to 150° C., preferably 0° C. to 80° C.

The product compound (I) may be subjected to hydrolysis of its ester bond. This hydrolysis can be carried out in the per se known method and the catalyst that can be used includes, for example, mineral acids such as hydrochloric acid, hydrobromic acid, sulfuric acid, etc., inorganic bases such as sodium hydroxide, potassium hydroxide, etc., and basic salts such as sodium carbonate, potassium carbonate, etc.

This reaction can be carried out with advantage in an inert solvent. The solvent is not particularly critical in kind unless the progress of the reaction is interfered with. The preferred inert solvent includes, for example, alcohols such as methanol, ethanol, propanol, etc., ethers such as tetrahydrofuran, dioxane, 1,2-dimethoxyethane, diethyl ether, diisopropyl ether, etc., acetic acid, water, and mixtures of these solvents.

The reaction time is generally 10 minutes to 6 hours, preferably 30 minutes to 2 hours. The reaction temperature is generally 0° C. to 100° C., preferably 10° C. to 100° C.

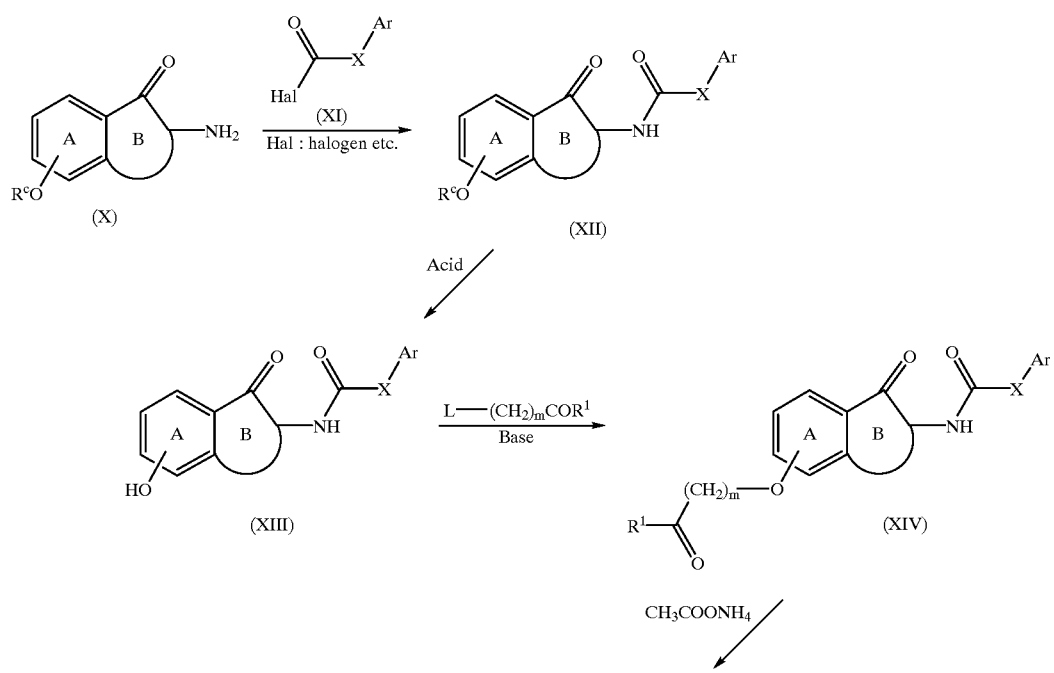

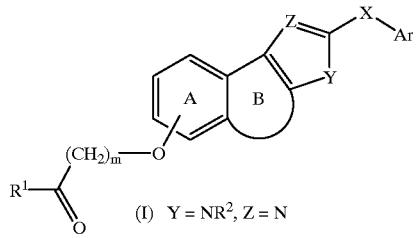

(I) Y = NR², Z = N

Compound (X) wherein $R^c$ represents a hydrocarbon group; the other symbols have the same meanings as defined above, can be produced by the per se known production processes, for example the processes described in Journal of Medicinal Chemistry, 22, 204 (1979), European Journal of Medicinal Chemistry, 23, 31 (1988), and Journal of Heterocyclic Chemistry, 29, 1245 (1992), or by any process analogous thereto.

The "hydrocarbon group" for $R^c$ includes the same group as the "hydrocarbon group" defined above.

Compound (XI) may be purchased from a commercial source if it is available on the market or can be produced by the per se known, method, for example the process described in Shin Jikken Kagaku Koza (New Series in Experimental Chemistry) 14, II, 1104–1120 (1977).

Compound (XII) can be produced by reacting compound (X) with compound (XI) optionally in the presence of a base. Compound (XI) is used in a proportion of generally about 1 to 5 moles, preferably about 1 to 1.2 moles, per mole of compound (X). The base that can be used includes, for example, inorganic bases such as alkali metal hydroxides, e.g. sodium hydroxide, potassium hydroxide, etc., ammonia, etc., organic bases such as triethylamine, pyridine, etc., and basic salts such as potassium hydrogen carbonate, sodium carbonate, potassium carbonate, sodium acetate, etc. The proportion of the base is generally about 0.1 to 5 moles, preferably about 1 to 2 moles, per mole of compound (X).

This reaction can be carried out with advantage in the absence of a solvent or in the presence of an inert solvent. There is no particular limitation on the kind of inert solvent that can be used unless the progress of the reaction is interfered with. The inert solvent includes, for example, a variety of organic solvents, viz. alcohols such as methanol, ethanol, propanol, etc., saturated hydrocarbons such as cyclohexane, hexane, etc., aromatic hydrocarbons such as benzene, toluene, xylene, etc., ethers such as tetrahydrofuran, dioxane, 1,2-dimethoxyethane, diethyl ether, diisopropyl ether, etc., amides such as N,N-dimethylformamide, N,N-dimethylacetamide, hexamethylphosphoric triamide, etc., sulfoxides such as dimethyl sulfoxide etc., halogenated hydrocarbons such as dichloromethane, chloroform, carbon tetrachloride, 1,2-dichloroethane, etc., water, and mixtures of these solvents.

The reaction time varies with the species of reagents and solvent used but is generally 30 minutes to 24 hours, preferably 2 to 14 hours. The reaction temperature is generally 0° C. to 150° C., preferably 30° C. to 100° C.

The product can be directly used, either as the reaction mixture as such or in a partially purified form, in the next reaction. If desired, however, the product compound can be isolated from the reaction mixture in the routine manner and expediently purified by the conventional purification procedure (e.g. recrystallization, distillation, chromatography, etc.).

Compound (XIII) can be produced from compound (XII) by the same procedure as described for the production of compound (III) from compound (II).

Compound (XIV) can be produced from compound (XIII) by the same procedure as described for the production of compound (IV) from compound (III).

Compound (I) can be produced by reacting compound (XIV) with ammonium acetate. The proportion of ammonium acetate is generally about 5 to 100 moles, preferably about 10 to 30 moles, per mole of compound (XIV).

This reaction can be conducted with advantage in the absence of a solvent or in the presence of an inert solvent. The solvent is not critical in kind unless the progress of the reaction is interfered with. The preferred inert solvent includes water or mixtures of water with organic solvents, e.g. organic acids such as acetic acid, propionic acid, etc., alcohols such as methanol, ethanol, propanol, etc., saturated hydrocarbons such as cyclohexane, hexane, etc., aromatic hydrocarbons such as benzene, toluene, xylene, etc., ethers such as tetrahydrofuran, dioxane, 1,2-dimethoxyethane, diethyl ether, diisopropyl ether, etc., amides such as N,N-dimethylformamide, N,N-dimethylacetamide, hexamethylphosphoric triamide, etc., sulfoxides such as dimethyl sulfoxide etc., and halogenated hydrocarbons such as dichloromethane, chloroform, carbon tetrachloride, 1,2-dichloroethane, etc.

The reaction time varies with the species of reactant and solvent used but is generally 30 minutes to 24 hours, preferably 2 to 14 hours. The reaction temperature is generally 25° C. to 180° C., preferably 80C to 150° C.

When the starting compounds for the above reactions have amino, carboxyl, and/or hydroxy groups, such functional groups may have been protected in advance with those protective groups which are generally used in peptide chemistry and the objective compounds can be obtained by removing such protective groups after the respective reactions.

The amino-protective group includes, for example, formyl as well as $C_{1-6}$ alkyl-carbonyl (e.g. acetyl, propionyl, etc.), phenylcarbonyl, $C_{1-6}$ alkoxy-carbonyl (e.g. methoxycarbonyl, ethoxycarbonyl, etc.), phenyloxycarbonyl, $C_{7-11}$ aralkyloxy-carbonyl (e.g. benzyloxycarbonyl etc.), trityl, and phthaloyl, each of which may be substituted. The substituent includes halogen (e;g. fluorine, chlorine, bromine, iodine, etc.), $C_{1-6}$ alkyl-carbonyl (e.g. acetyl, propionyl, valeryl, etc.), nitro, etc. and the number of substituents may range from 1 to 3.

The carboxyl-protective group includes, for example, $C_{1-6}$ alkyl (e.g. methyl, ethyl, propyl, isopropyl, butyl, tert-butyl, etc.), phenyl, trityl, and silyl, each of which may be substituted. The substituent includes halogen (e.g. fluorine, chlorine, bromine, iodine, etc.), formyl, $C_{1-6}$ alkyl-carbonyl (e.g. acetyl, propionyl, butylcarbonyl, etc.), nitro, $C_{1-6}$ alkyl (e.g. methyl, ethyl, tert-butyl, etc.), and $C_{6-10}$ aryl (e.g. phenyl, naphthyl, etc.) and the number of substituents may range from 1 to 3.

The hydroxy-protecting group includes, for example, $C_{1-6}$ alkyl (e.g. methyl, ethyl, propyl, isopropyl, butyl, tert-butyl, etc.), phenyl, $C_{7-11}$ aralkyl (e.g. benzyl etc.), formyl, $C_{1-6}$ alkyl-carbonyl (e.g. acetyl, propionyl, etc.), phenyloxycarbonyl, $C_{7-11}$, aralkyloxy-carbonyl (e.g. benzyloxycarbonyl etc.), tetrahydropyranyl, tetrahydrofuranyl, and silyl, each of which may be substituted. The substituent includes halogen (e.g. fluorine, chlorine, bromine, iodine, etc.), $C_{1-6}$ alkyl (e.g. methyl, ethyl, tert-butyl, etc.), $C_{7-11}$ aralkyl (e.g. benzyl etc.), $C_{6-10}$ aryl (e.g. phenyl, naphthyl, etc.), nitro, etc. and the number of substituents may range from 1 to 4.

Such protective groups can be removed by the per se known deprotection methods or any methods analogous thereto. For example, the treatment with an acid, a base, ultraviolet radiation, hydrazine, phenylhydrazine, sodium N-methyldithiocarbamate, tetrabutylammonium fluoride, or palladium acetate and reduction can be mentioned by way of example.

In any of the foregoing processes, the desired compound (I) can be synthesized by carrying out any of the known deprotection, acylation, amidation, alkylation, hydrogenation, oxidation, reduction, carbon chain elongation reaction, and substituent exchange reaction or two or more of such reactions in combination as necessary. Those reactions can be typically carried out by the procedures described inter alia in Shin Jikken Kagaku Koza (New Experimental Chemistry Series 14, Vol. 15, 1977 (Maruzen Publishing Co.).

When the objective compound obtainable by the above reaction or reactions is a free compound, it can be converted to a salt in the routine manner. When the product compound is a salt, it can be converted to the free compound or a different salt by the known procedure. The compound (I) thus produced can be isolated and purified from the reaction mixture by the known procedures such as redistribution, concentration, solvent extraction, fractional distillation, crystallization, recrystallization, and chromatography.

When compound (I) exists as configuration isomers, diastereomers, or conformers, the respective isomers can be optionally isolated by the above-mentioned fractionation and purification procedures. When compound (I) is a racemic compound, it can be resolved into the (S)- and (R)- forms by the conventional optical resolution techniques.

Compound (I) may be a hydrate or an anhydrate.

The compound of the formula:

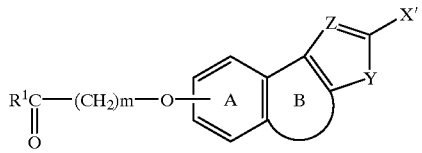

wherein X' represents SH, OH or $NH_2$; the other symbols have the same meanings as defined above, or a tautomer thereof, or a salt thereof as obtained in the above reaction processes is novel compound and can be used as a starting material for the production of the compound of the present invention.

Among others, the preferred compound include:
Ethyl[(2-mercapto-4,5-dihydronaphtho[1,2-d]thiazol-6-yl)oxy]acetate,
Ethyl[(2-mercapto-8H-indeno[1,2-d]thiazol-7-yl)oxy]acetate,
Ethyl[(2-mercapto-4H-[1]benzopyrano[4,3-d]thiazol-6-yl)-oxy]acetate, tautomers thereof and salts thereof.

Compound (I) of the invention has a high affinity for the $PGI_2$ receptors with a low toxic potential and a minimal risk of adverse drug reaction and, as such, is of value as a medicine.

Compound (I) of the invention acts as a $PGI_2$ agonist in mammals (e.g. mouse, rat, hamster, rabbit, cat, dog, bovine, sheep, monkey, and human) and has platelet aggregation inhibitory, vasodilative, bronchodilative, lipid deposition inhibitory, leukocyte activation inhibitory, and other activities. Thus, compound (I) is useful for the pharmaceutical composition for the prophylaxis and/or treatment of transient ischemic attack (TIA), diabetic neuropathy, peripheral vascular diseases (e.g. peripheral embolism, vibration syndrome, Raynaud's disease, etc.), systemic lupus erythematosus, post-PTCA reobliteration/restenosis, atherosclerosis, thrombosis (e.g. acute phase of cerebral thrombosis, etc.), diabetic gangrene, hypertension, pulmonary hypertension, ischemic diseases (e.g. cerebral infarction, myocardial infarction, etc.), angina pectoris (e.g. stable angina, unstable angia, etc.), glomerulonephritis, diabetic nephropathy, allergy, bronchial asthma, ulcer, decubitus, coronary restenosis after coronary intervention such as atherectomy and stent implantation, thrombocytopenia during dialysis, etc.

Compound (I) of the invention is a compound of low toxicity and can be safely administered either as it is or in the form of a pharmaceutical composition comprising compound (I) and a pharmacologically acceptable carrier or vehicle, for example in such dosage forms as tablets (including dragees and film-coated tablets), powders, granules, capsules (including soft capsules), solutions, injections, suppositories, sustained release tablets or capsules, transdermal drug delivery systems, etc., whether orally or non-orally (e.g. topically, rectally, or intravenously). The content of compound (I) in the pharmaceutical composition of the invention is about 0.01 to 100 weight % based on the total weight of the composition. The dosage is dependent on the background factors, administration route, diagnosis, etc. but when the composition is to be administered orally to an adult human as a pharmaceutical composition for the prophylaxis and/or treatment of transient ischemic attack, about 0.1 to 50 mg/kg body weight, preferably about 0.2 to 30 mg/kg b. wt., more preferably about 0.5 to 10 mg/kg b. wt. as compound (I) can be administered once in a few divided doses daily.

Compound (I) can be used with other active ingredients such as hypolipidemic (e.g. Pravastatin, etc.), angiotensin II antagonist. (e.g. Candesartan Cilexetil, Losartan, etc.), calcium blocker (e.g. Amlodipine, Manidipine, etc.), insulin sensibility activator (e.g. Triglitazone, Pioglitazone, etc.), etc. Compound (I) and said other active ingredient can be formulated into one pharmaceutical composition such as tablets (including dragees and film-coated tablets), powders, granules, capsules (including soft capsules), solutions, injections, suppositories, sustained release tablets or capsules, according to per se known methods. They may be separately formulated into different preparations, which may be administered to one and the same subject either simultaneously or at different times.

The pharmacologically acceptable carrier or vehicle which can be used in the manufacture of various dosage forms according to the invention includes those organic and inorganic substances which are conventionally used in pharmaceutical manufacture, such as the excipient, lubricant, binder, and disintegrator for solid dosage forms and the solvent, solubilizer, suspending agent, isotonizing agent, buffer, and local anesthetic for liquid dosage forms. Where necessary, the routine additives such as the antiseptic, antioxidant, coloring agent, sweetener, adsorbent, wetting agent, etc. can be included in the formulation.

The excipient mentioned above includes, for example, lactose, sucrose, D-mannitol, starch, corn starch, crystalline cellulose, and light silicic anhydride.

The lubricant includes, for example, magnesium stearate, calcium stearate, talc, and colloidal silica.

The binder includes, for example, crystalline cellulose, sucrose, D-mannitol, dextrin, hydroxypropylcellulose, hydroxypropylmethylcellulose, polyvinylpyrrolidone, starch, gelatin, methylcellulose, and carboxymethylcellulose sodium.

The disintegrator includes, for example, starch, carboxymethylcellulose, carboxymethylcellulose calcium, croscarmellose sodium, carboxymethylstarch sodium, and L-hydroxypropylcellulose.

The solvent includes, for example, water for injection, alcohol, propylene glycol, macrogols, sesame oil, corn oil, and olive oil.

The solubilizer includes, for example, polyethylene glycol, propylene glycol, D-mannitol, benzyl benzoate, ethanol, trisaminomethane, cholesterol, triethanolamine, sodium carbonate, and sodium citrate.

The suspending agent includes, for example, surfactants such as stearyltriethanolamine, sodium lauryl sulfate, laurylaminopropionic acid, lecithin, benzalkonium chloride, benzethonium chloride, glyceryl monostearate, etc. and hydrophilic macromolecular substances such as polyvinyl alcohol, polyvinylpyrrolidone, carboxymethylcellulose sodium, methylcellulose, hydroxymethylcellulose, hydroxyethylcellulose, and hydroxypropylcellulose.

The isotonizing agent includes, for example, glucose, D-sorbitol, sodium chloride, glycerol, and D-mannitol.

The buffer includes, for example, buffer solutions such as, phosphate, acetate, carbonate and citrate.

The local anesthetic includes, for example, benzyl alcohol.

The antiseptic includes, for example, p-hydroxybenzoic esters, chlorobutanol, benzyl alcohol, phenethyl alcohol, dehydroacetic acid, and sorbic acid.

The antioxidant includes, for example, salts of sulfurous acid, ascorbic acid, and α-tocopherol.

BEST MODE FOR CARRYING OUT OF THE INVENTION

The following reference examples, examples, formulation example, and experimental examples are intended to describe the present invention in further detail, it being be understood, however, that these examples are merely illustrative and not defining the scope of the invention and that many changes and modifications may be made by one skilled in the art without departing from the spirit of the invention.

The term "room temperature" as used in the following reference examples and examples generally means a temperature within the range of about 10° C. to about 35° C. The symbol % stands for weight percent unless otherwise indicated.

The various abbreviations used in the text have the following meanings.
s: singlet
d: doublet
t: triplet
q: quartet
dd: double doublet
dt: double triplet
m: multiplet
br: broad
J: coupling constant
Hz: Hertz
Ph: phenyl
Me: methyl
Et: ethyl
$CDCl_3$: deuterated chloroform
DMSO-$d_6$: deuterated dimethyl sulfoxide
$^1$H-NMR: proton nuclear magnetic resonance spectrum

EXAMPLES

Reference Example 1

Ethyl[(5,6,7,8-tetrahydro-5-oxo-1-naphthalenyl)oxy]acetate

To a solution of 3,4-dihydro-5-hydroxy-1(2H)-naphthalenone (8.20 g, 50.6 mmol) in N,N-dimethylformamide (80 mL) was added sodium hydride (60% dispersion in liquid paraffin, 2.22 g, 55.6 mmol) at 0° C. and the mixture was stirred at that temperature for 10 minutes. Then, ethyl bromoacetate (9.29 g, 55.6 mmol) was added and the mixture was further stirred at room temperature for 30 minutes. This reaction mixture was poured in water (80 mL) and extracted with 2 portions of ethyl acetate. The organic layers were pooled, washed with water, dried over anhydrous magnesium sulfate ($MgSO_4$), and filtered, and the filtrate was concentrated under reduced pressure. The residue was crystallized from hexane-diisopropyl ether to provide 8.40 g of the title compound. Yield 67%.

m.p. 58–60° C.

$^1$H-NMR ($CDCl_3$) δ: 1.30 (3H, t, J=7.2 Hz), 2.04–2.23 (2H, m), 2.60–2.71 (2H, m), 3.00 (2H, t, J=6.2 Hz), 4.28 (2H, q, J=7.2 Hz), 4.67 (2H, s), 6.91 (1H, dd, J=8.4, 1.2 Hz), 7.20–7.32 (1H, m), 7.70 (1H, dd, J=8.2, 1.2 Hz).

Reference Example 2

Ethyl[(2,3-dihydro-1-oxo-1H-inden-4-yl)oxy]acetate

Using 2,3-dihydro-4-hydroxy-1H-inden-1-one, the procedure of Reference Example 1 was otherwise repeated to synthesize the title compound. Yield 70%.

m.p. 91–93° C. (hexane-diisopropyl ether)

$^1$H-NMR ($CDCl_3$) δ: 1.31 (3H, t, J=7.2 Hz), 2.66–2.74 (2H, m), 3.10–3.18 (2H, m), 4.28 (2H, q, J=7.2 Hz), 4.73 (2H, s), 6.92 (1H, dd, J=7.6, 1.0 Hz), 7.26–7.44 (2H, m).

Reference Example 3

Ethyl[(5,6,7,8-tetrahydro-5-oxo-2-naphthalenyl)oxy]acetate

Using 3,4-dihydro-6-hydroxy-1(2H)-naphthalene, the procedure of Reference Example 1 was otherwise repeated to synthesize the title compound. Yield 89%.

m.p. 39–41° C. (hexane-diisopropyl ether)

$^1$H-NMR ($CDCl_3$) δ: 1.31 (3H, t, J=7.4 Hz), 2.03–2.21 (2H, m), 2.57–2.66 (2H, m), 2.87–2.96 (2H, m), 4.29 (2H, q, J=7.4 Hz), 4.68 (2H, s), 6.73 (1H, d, J=2.4 Hz), 6.82 (1H, dd, J=8.8, 2.6 Hz), 8.02 (1H, dd, J=8.8, 2.6 Hz).

Reference Example 4

Ethyl[(2,3-dihydro-1-oxo-1H-inden-5-yl)oxy]acetate

Using-2,3-dihydro-5-hydroxy-1H-inden-1-one, the procedure of Reference Example 1 was otherwise repeated to synthesize the title compound. Yield 65%.

m.p. 59–61° C. (hexane-ethyl acetate)

$^1$H-NMR ($CDCl_3$) δ: 1.31 (3H, t, J=7.0 Hz), 2.62–2.73 (2H, m), 3.05–3.15 (2H, m), 4.29 (2H, q, J=7.0 Hz), 4.71 (2H, s), 6.86–6.97 (2H, m), 7.71 (1H, d, J=8.4 Hz).

Reference Example 5

Ethyl 4-[(2,3-dihydro-1-oxo-1H-inden-4-yl)oxy]butyrate

Using 2,3-dihydro-4-hydroxy-1H-inden-1-one and ethyl 4-bromo butyrate, the procedure of Reference Example 1 was otherwise repeated to synthesize the title compound. Yield 66%. Oil.

$^1$H-NMR ($CDCl_3$) δ: 1.27 (3H, t, J=7.0 Hz), 2.07–2.16 (2H, m), 2.55 (2H, t, J=7.2 Hz), 2.64–2.75 (2H, m), 2.99–3.10 (2H, m), 4.05–4.22 (4H, m), 7.06 (1H, dd, J=6.4, 2.4 Hz), 7.27–7.41 (2H, m).

Reference Example 6
Ethyl[(2,3-dihydro-5,7-dimethyl-1-oxo-1H-inden-4-yl)oxy]acetate Using 2,3-dihydro-4-hydroxy-5,7-dimethyl-1H-inden-1-one, the procedure of Reference Example 1 was otherwise repeated to synthesize the title compound. Yield 77%.

m.p. 75–77° C. (hexane-diisopropyl ether)

$^1$H-NMR (CDCl$_3$) δ: 1.33 (3H, t, J=7.2 Hz), 2.36 (3H, s), 2.55 (3H, s), 2.60–2.71 (2H, m), 3.04–3.13 (2H, m), 4.30 (2H, q, J=7.2 Hz), 4.54 (2H, s), 6.94 (1H, s).

Reference Example 7
Ethyl[(2,3-dihydro-6,7-dimethyl-1-oxo-1H-inden-4-yl)oxy]acetate Using 2,3-dihydro-4-hydroxy-6,7-dimethyl-1H-inden-1-one, the procedure of Reference Example 1 was otherwise repeated to synthesize the title compound. Yield 77%.

m.p. 100–101° C. (hexane-diisopropyl ether)

$^1$H-NMR (CDCl$_3$) δ: 1.31 (3H, t, J=7.0 Hz), 2.28 (3H, s), 2.51 (3H, s), 2.61–2.69 (2H, m), 2.98–3.05 (2H, m), 4.28 (2H, q, J=7.0 Hz), 4.68 (2H, s), 6.73 (1H, s).

Reference Example 8
Ethyl[(2,3-dihydro-4-oxo-4H-1-benzopyran-8-yl)oxy]acetate Using 2,3-dihydro-8-hydroxy-4H-1-benzopyran-4-one, the procedure of Reference Example 1 was otherwise repeated to synthesize the title compound. Yield 84%.

m.p. 56–66° C. (ethyl acetate-hexane)

$^1$H-NMR (CDCl$_3$) δ: 1.30 (3H, t, J=7.2 Hz), 2.84 (2H, t, J=6.4 Hz), 4.28 (2H, q, J=7.2 Hz), 4.65 (2H, t, J=6.4 Hz), 4.71 (2H, s), 6.93 (1H, t, J=7.6 Hz), 7.01 (1H, dd, J=7.6, 1.8 Hz), 7.57 (1H, dd, J=7.6, 1.8 Hz).

Reference Example 9
Ethyl 3-[(2,3-dihydro-1-oxo-1H-inden-4-yl)oxy]propionate To a solution of 2,3-dihydro-4-hydroxy-1H-inden-1-one (18.0 g, 121 mmol) in 30% aqueous potassium hydroxide solution (60 mL) was added 3-chloropropionic acid (18 g, 166 mmol) at room temperature and the mixture was refluxed for 1 hour. After cooling, 1N-hydrochloric acid was added and the precipitate (10.0 g) comprised of unreacted 2,3-dihydro-4-hydroxy-1H-inden-1-one was separated by filtration. The filtrate was extracted with 2 portions of ethyl acetate and the pooled extract was washed with water, dried over MgSO$_4$, and filtered. The filtrate was concentrated under reduced pressure to provide crude crystals (6.20 g) of 3-[(2,3-dihydro-1-oxo-1H-inden-4-yl)oxy]propionic acid. This crystal crop was dissolved in ethanol (40 mL) followed by addition of concentrated sulfuric acid (1.0 mL) at room temperature and the mixture was refluxed for 1 hour. After cooling, the reaction mixture was extracted with 2 portions of ethyl acetate and the pooled organic solution was washed with saturated aqueous sodium hydrogen carbonate solution, dried over MgSO$_4$, and filtered. The filtrate was concentrated under reduced pressure and the residue was crystallized from hexane-diisopropyl ether to provide 6.50 g of the title compound. Yield 22%.

m.p. 90–92° C.

$^1$H-NMR (CDCl$_3$) δ: 1.29 (3H, t, J=7.0 Hz), 2.63–2.76 (2H, m), 2.85 (2H, t, J=6.2 Hz), 2.96–3.08 (2H, m), 4.20 (2H, q, J=7.0 Hz), 4.35 (2H, t, J=6.2 Hz), 7.06 (1H, dd, J=6.6, 2.6 Hz), 7.22–7.40 (2H, m).

Reference Example 10
Ethyl 3-[(5,6,7,8-tetrahydro-5-oxo-1-naphthalenyl)oxy]propionate Using 3,4-dihydro-5-hydroxy-1(2H)-naphthalene, the procedure of Reference Example 9 was otherwise repeated to synthesize the title compound. Yield 11%.

m.p. 57–59° C. (hexane)

$^1$H-NMR (CDCl$_3$) δ: 1.29 (3H, t, J=7.0 Hz), 2.02–2.19 (2H, m), 2.57–2.66 (2H, m), 2.77–2.90 (4H, m), 4.18–4.33 (4H, m), 7.04 (1H, d, J=8.0 Hz), 7.26 (1H, t, J=8.0 Hz), 7.66 (1H, d, J=8.0 Hz).

Reference Example 11
Ethyl[(6-bromo-5,6,7,8-tetrahydro-5-oxo-1-naphthalenyl)oxy]acetate To a boiled suspension of copper (II) bromide (10 g, 45.1 mmol) in ethyl acetate (50 mL) was added a solution of ethyl[(5,6,7,8-tetrahydro-5-oxo-1-naphthalenyl)oxy]acetate (7.0 g, 28.2 mmol) in ethyl acetate (30 mL) and the mixture was refluxed for 6 hours. The copper (I) bromide was filtered off and the filtrate was washed with saturated aqueous sodium hydrogen carbonate solution, dried over MgSO$_4$, and filtered. The filtrate was concentrated under reduced pressure and the residue was crystallized from hexane-ethyl acetate to provide 7.5 g of the title compound. Yield 81%.

m.p. 74–75° C.

$^1$H-NMR (CDCl$_3$) δ: 1.31 (3H, t, J=7.0 Hz), 2.44–2.54 (2H, m), 3.08–3.17 (2H, m), 4.23 (2H, q, J=7.0 Hz), 4.62–4.75 (3H, m), 6.94 (1H, d, J=8.0 Hz), 7.29 (1H, t, J=8.0 Hz), 7.75 (1H, d, J=8.0 Hz).

Reference Example 12
Ethyl[(2-bromo-2,3-dihydro-1-oxo-1H-inden-4-yl)oxy]acetate Using ethyl[(2,3-dihydro-1-oxo-1H-inden-4-yl)oxy]acetate, the procedure of Reference Example 11 was otherwise repeated to synthesize the title compound. Yield 77%.

m.p. 60–63° C. (hexane-diisopropyl ether)

$^1$H-NMR (CDCl$_3$) δ: 1.31 (3H, t, J=7.2 Hz), 3.41 (1H, dd, J=18.6, 3.0 Hz), 3.84 (1H, dd, J=18.6, 7.4 Hz), 4.28 (2H, q, J=7.2 Hz), 4.65 (1H, dd, J=7.4, 3.0 Hz), 4.73 (2H, s), 6.99 (1H, d, J=7.6 Hz), 7.33–7.51 (2H, m).

Reference Example 13
Ethyl[(6-bromo-5,6,7,8-tetrahydro-5-oxo-2-naphthalenyl)oxy]acetate Using ethyl[(5,6,7,8-tetrahydro-5-oxo-2-naphthalenyl)oxy]acetate, the procedure of Reference Example 11 was otherwise repeated to synthesize the title compound. Yield 73%. Oil.

$^1$H-NMR (CDCl$_3$) δ: 1.31 (3H, t, J=7.2 Hz), 2.35–2.62 (2H, m), 2.72–2.95 (1H, m), 3.20–3.41 (1H, m), 4.29 (2H, q, J=7.2 Hz), 4.62–4.75 (3H, m), 6.74 (1H, d, J=2.4 Hz), 6.87 (1H, dd, J=8.8, 2.6 Hz), 7.75 (1H, d, J=8.8 Hz).

Reference Example 14
Ethyl[(2-bromo-2,3-dihydro-1-oxo-1H-inden-5-yl)oxy]acetate Using ethyl[(2,3-dihydro-1-oxo-1H-inden-5-yl)oxy]acetate, the procedure of Reference Example 11 was otherwise repeated to synthesize the title compound. Yield 93%. Oil.

$^1$H-NMR (CDCl$_3$) δ: 1.32 (3H, t, J=7.0 Hz), 3.38 (1H, dd, J=18.4, 3.2 Hz), 3.79 (1H, dd, J=18.4, 7.6 Hz), 4.30 (2H, q, J=7.0 Hz), 4.65 (1H, dd, J=7.6, 3.2 Hz), 4.73 (2H, s), 6.85 (1H, d, J=2.0 Hz), 6.98 (1H, dd, J=8.6, 2.0 Hz), 7.80 (1H, d, J=8.6 Hz).

Reference Example 15
Ethyl 4-[(2-bromo-2,3-dihydro-1-oxo-1H-inden-4-yl)oxy]butyrate Using ethyl4-[(2,3-dihydro-1-oxo-1H-inden-4-yl)oxy]butyrate, the procedure of Reference Example 11 was otherwise repeated to synthesize the title compound. Yield 90%. Oil.

$^1$H-NMR (CDCl$_3$) δ: 1.27 (3H, t, J=7.0 Hz), 2.11–2.24 (2H, m), 2.49–2.61 (2H, m), 3.31 (1H, dd, J=18.4, 3.0 Hz), 3.75 (1H, dd, J=18.4, 7.2 Hz), 4.05–4.23 (4H, m), 4.64 (1H, dd, J=7.2, 3.0 Hz), 7.09 (1H, dd, J=7.2, 2.0 Hz), 7.31–7.45 (2H, m).

Reference Example 16

Ethyl 3-[(2-bromo-2,3-dihydro-1-oxo-1H-inden-4-yl)oxy]propionate

Using ethyl3-[(2,3-dihydro-1-oxo-1H-inden-4-yl)oxy]propionate, the procedure of Reference Example 11 was otherwise repeated to synthesize the title compound. Yield 78%. Oil.

$^1$H-NMR (CDCl$_3$) δ: 1.30 (3H, t, J=7.0 Hz), 2.85 (2H, t, J=6.2 Hz), 3.35 (1H, dd, J=18.6, 3.0 Hz), 3.78 (1H, dd, J=18.6, 7.4 Hz), 4.20 (2H, q, J=7.0 Hz), 4.35 (2H, t, J=6.2 Hz), 4.66 (1H, dd, J=7.4, 3.0 Hz), 7.11 (1H, dd, J=6.6, 2.6 Hz), 7.25–7.43 (2H, m).

Reference Example 17

Ethyl 3-[(6-bromo-5,6,7,8-tetrahydro-5-oxo-1-naphthalenyl)oxy]propionate

Using ethyl3-[(5,6,7,8-tetrahydro-5-oxo-1-naphthalenyl)oxy]propionate, the procedure of Reference Example 11 was otherwise repeated to synthesize the title compound. Yield 80%. Oil.

$^1$H-NMR (CDCl$_3$) δ: 1.29 (3H, t, J=7.0 Hz), 2.41–2:51 (2H, m), 2.84 (2H, t, J=6.2 Hz), 2.99 (2H, t, J=6.2 Hz), 4.21 (2H, q, J=7.0 Hz), 4.31 (2H, t, J=6.2 Hz), 4.70 (1H, t, J=4.4 Hz), 7.09 (1H, d, J=8.0 Hz), 7.31 (1H, t, J=8.0 Hz), 7.72 (1H, d, J=8.0 Hz).

Reference Example 18

Ethyl[(2-bromo-2,3-dihydro-5,7-dimethyl-1-oxo-1H-inden-4-yl)oxy]acetate

Using ethyl[(2,3-dihydro-5,7-dimethyl-1-oxo-1H-inden-4-yl)oxy]acetate, the procedure of Reference Example 11 was otherwise repeated to synthesize the title compound. Yield 87%.

m.p. 71–73° C. (hexane-ethyl acetate)

$^1$H-NMR (CDCl$_3$) δ: 1.33 (3H, t, J=7.0 Hz), 2.38 (3H, s), 2.56 (3H, s), 3.38 (1H, dd, J=18.6, 3.2 Hz), 3.83 (1H, dd, J=18.6, 7.4 Hz), 4.29 (2H, q, J=7.2 Hz), 4.51 (2H, s), 4.61 (1H, dd, J=7.4, 3.2 Hz), 7.02 (1H, s).

Reference Example 19

Ethyl[(2-bromo-2,3-dihydro-6,7-dimethyl-1-oxo-1H-inden-4-yl)oxy]acetate

Using ethyl[(2,3-dihydro-6,7-dimethyl-1-oxo-1H-inden-4-yl)oxy]acetate, the procedure of Reference Example 11 was otherwise repeated to synthesize the title compound. Yield 90%.

m.p. 71–73° C. (hexane-ethyl acetate)

$^1$H-NMR (CDCl$_3$) δ: 1.31 (3H, t, J=7.0 Hz), 2.30 (3H, s), 2.52 (3H, s), 3.30 (1H, dd, J=18.6, 3.0 Hz), 3.73 (1H, dd, J=18.6, 7.6 Hz), 4.28 (2H, q, J=7.2 Hz), 4.61 (1H, dd, J=7.6, 3.0 Hz), 4.68 (2H, s), 6.79 (1H, s).

Reference Example 20

Ethyl[(3-bromo-2,3-dihydro-4-oxo-4H-1-benzopyran-8-yl)oxy]acetate

Using ethyl[(2,3-dihydro-4-oxo-4H-1-benzopyran-8-yl)oxy]acetate, the procedure of Reference Example 11 was otherwise repeated to synthesize the title compound. Yield 77%.

m.p. 92.0–93.0° C. (ethyl acetate-hexane)

$^1$H-NMR (CDCl$_3$) δ: 1.31 (3H, t, J=7.2 Hz), 4.29 (2H, q, J=7.2 Hz), 4.64–4.82 (5H, m), 6.97–7.09 (2H, m), 7.62 (1H, dd, J=7.4, 2.0 Hz).

Reference Example 21

Ethyl[(2-mercapto-4,5-dihydronaphtho[1,2-d]thiazol-6-yl)oxy]acetate

A mixture of ethyl[(2-bromo-5,6,7,8-tetrahydro-5-oxo-1-naphthalenyl)oxy]acetate (2.63 g, 8.04 mmol), ammonium dithiocarbamate (1.06 g, 9.60 mmol), and ethanol (30 mL) was refluxed for 14 hours. After cooling, the solid precipitate was recovered by filtration to provide 1.96 g of the title compound. Amorphous solid. Yield 76%.

$^1$H-NMR (DMSO-d$_6$) δ: 1.24 (3H, t, J=7.2 Hz), 2.63–2.79 (2H, m), 2.95–3.09 (2H, m), 4.18 (2H, q, J=7.2 Hz), 4.79 (2H, s), 6.88 (1H, d, J=8.0 Hz), 7.20 (1H, t, J=8.0 Hz), 7.40 (1H, d, J=8.0 Hz), 13.6 (1H, br s).

Reference Example 22

Ethyl[(2-mercapto-8H-indeno[1,2-d]thiazol-7-yl)oxy]acetate

Using ethyl[(2-bromo-2,3-dihydro-1-oxo-1H-inden-4-yl)oxy]acetate, the procedure of Reference Example 21 was otherwise repeated to synthesize the title compound. Yield 70%. Amorphous solid.

$^1$H-NMR (DMSO-d$_6$) δ: 1.22 (3H, t, J=7.2 Hz), 3.68 (2H, s), 4.28 (2H, q, J=7.2 Hz), 4.88 (2H, s), 6.84 (1H, dd, J=8.0, 1.0 Hz), 7.20–7.40 (2H, m), 14.1 (1H, br s).

Reference Example 23

Ethyl[(2-mercapto-4,5-dihydronaphtho[1,2-d]thiazol-7-yl)oxy]acetate

Using ethyl[(6-bromo-5,6,7,8-tetrahydro-5-oxo-2-naphthalenyl)oxy]acetate, the procedure of Reference Example 21 was otherwise repeated to synthesize the title compound. Yield 52%. Amorphous solid.

$^1$H-NMR (DMSO-d$_6$) δ: 1.24 (3H, t J=7.0 Hz), 2.63–2.78 (2H, m), 2.87–3.05 (2H, m), 4.19 (2H, q, J=7.0 Hz), 4.79 (2H, s), 6.84–6.92 (2H, m), 7.66 (1H, d, J=8.4 Hz), 13.6 (1H, br s).

Reference Example 24

Ethyl 3-[(2-mercapto-8H-indeno[1,2-d]thiazol-7-yl)oxy]propionate

Using ethyl3-[(2-bromo-2,3-dihydro-1-oxo-1H-inden-4-yl)oxy]propionate, the procedure of Reference Example 21 was otherwise repeated to synthesize the title compound. Yield 45%. Amorphous solid.

$^1$H-NMR (DMSO-d$_6$) δ: 1.21 (3H, t, J=7.0 Hz), 2.72–2.85 (2H, m), 3.57 (2H, s), 4.12 (2H, q, J=7.0 Hz), 4.28–4.36 (2H, m), 6.80–7.40 (3H, m), 1H not confirmed.

Reference Example 25

Ethyl[(2-mercapto-8H-indeno[1,2-d]thiazol-6-yl)oxy]acetate

Using ethyl[(2-bromo-2,3-dihydro-1-oxo-1H-inden-5-yl)oxy]acetate, the procedure of Reference Example 21 was otherwise repeated to synthesize the title compound. Yield 80%. Amorphous solid.

$^1$H-NMR (DMSO-d$_6$) δ: 1.24 (3H, t, J=7.0 Hz), 3.71 (2H, s), 4.19 (2H, q, J=7.0 Hz), 4.79 (2H, s), 6.88–6.96 (1H, m), 7.18 (1H, br s), 7.42–7.51 (1H, m), 14.3 (1H, br s).

Reference Example 26

Ethyl[(2-mercapto-4,6-dimethyl-8H-indeno[1,2-d]thiazol-7-yl)oxy]acetate

Using ethyl[(2-bromo-2,3-dihydro-5,7-dimethyl-1-oxo-1H-inden-4-yl)oxy]acetate, the procedure of Reference Example 21 was otherwise repeated to synthesize the title compound. Yield 34%. Amorphous solid.

¹H-NMR (DMSO-$d_6$) δ: 1.24 (3H, t, J=7.0 Hz), 2.26 (3H, s), 2.48 (3H, s), 3.76 (2H, s), 4.18 (2H, q, J=7.0 Hz), 4.66 (2H, s), 6.95 (1H, s), 13.6 (1H, br s).

Reference Example 27
Ethyl[(2-mercapto-4,5-dimethyl-8H-indeno[1,2-d]thiazol-7-yl)oxy]acetate Using ethyl[(2-bromo-2,3-dihydro-6,7-dimethyl-1-oxo-1H-inden-4-yl)oxy]acetate, the procedure of Reference Example 21 was otherwise repeated to synthesize the title compound. Yield 64%. Amorphous solid.

¹H-NMR (DMSO-$d_6$) δ: 1.22 (3H, t, J=7.0 Hz), 2.25 (3H, s), 2.37 (3H, s), 3.55 (2H, s), 4.17 (2H, q, J=7.0 Hz), 4.82 (2H, s), 6.69 (1H, s), 13.5 (1H, br s).

Reference Example 28
Ethyl[(2-mercapto-4H-[1]benzopyrano[4,3-d]thiazol-6-yl)oxy]acetate Using-ethyl[(3-bromo-2,3-dihydro-4-oxo-4H-1-benzopyran-8-yl)oxy]acetate, the procedure of Reference Example 21 was otherwise repeated to synthesize the title compound. Yield 49%. Amorphous solid.

¹H-NMR (CDCl$_3$) δ: 1.29 (3H, t, J=7.2 Hz), 4.27 (2H, q, J=7.2 Hz), 4.69 (2H, s), 5.22 (2H, s), 6.81 (1H, dd, J=8.2, 1.6 Hz), 7.20 (1H, t, J=8.2 Hz), 7.32 (1H, dd, J=8.2, 1.6 Hz), 13.4 (1H, br s).

Reference Example 29
Ethyl 4-[(2-mercapto-8H-indeno[1,2-d]thiazol-7-yl)oxy]butyrate Using ethyl4-[(2-bromo-2,3-dihydro-1-oxo-1H-inden-4-yl)oxy]butyrate, the procedure of Reference Example 21 was otherwise repeated to synthesize the title compound. Yield 68%. Amorphous solid.

¹H-NMR (CDCl$_3$) δ: 1.27 (3H, t, J=7.2 Hz), 2.09–2.25 (2H, m), 2.56 (2H, t, J=7.2 Hz), 3.61 (2H, s), 4.13 (2H, t, J=6.0 Hz), 4.17 (2H, q, J=7.2 Hz), 6.80 (1H, d, J=8.2 Hz), 7.14 (1H, d, J=7.2 Hz), 7.25–7.35 (1H, m), 13.6 (1H, br s).

Reference Example 30
Ethyl 3-[(2-mercapto-4,5-dihydronaphtho[1,2-d]thiazol-6-yl)oxy]propionate Using ethyl 3-[(6-bromo-5,6,7,8-tetrahydro-5-oxo-1-naphthalenyl)oxy]propionate, the procedure of Reference Example 21 was otherwise repeated to synthesize the title compound. Yield 59%. Amorphous solid.

¹H-NMR (DMSO-$d_6$) δ: 1.20 (3H, t, J=7.0 Hz), 2.61–2.93 (6H, m), 4.11 (2H, q, J=7.0 Hz), 4.23 (2H, t, J=6.0 Hz), 6.98 (1H, d, J=8.0 Hz), 7.23 (1H, t, J=8.0 Hz), 7.39 (1H, d, J=8.0 Hz), 13.6 (1H, br s).

Reference Example 31
Ethyl[(4,5-dihydro-2-hydroxynaphtho[1,2-d]thiazol-6-yl)oxy]acetate A mixture of ethyl[(6-bromo-5,6,7,8-tetrahydro-5-oxo-1-naphthalenyl)oxy]acetate (3.00 g, 9.17 mmol), ethyl xanthamide (0.96 g, 9.17 mmol), and ethanol (30 mL) was refluxed for 6 hours. The solvent was then distilled off under reduced pressure and the residue was diluted with ethyl acetate and water. After phase separation, the aqueous layer was extracted with ethyl acetate. The organic layers were combined, washed with water, dried over MgSO$_4$, and filtered. The filtrate was concentrated under reduced pressure and the residue was subjected to silica gel column chromatography (hexane-ethyl acetate=1:3) to provide 1.40 g of the title compound. Yield 50%.

m.p. 74–75° C. (ethyl acetate-hexane)

¹H-NMR (DMSO-$d_6$) δ: 1.23 (3H, t, J=7.0 Hz), 2.55–2.70 (2H, m), 2.92–3.04 (2H, m), 4.18 (2H, q, J=7.0 Hz), 4.79 (2H, s), 6.82 (1H, dd, J=8.0, 1.4 Hz), 7.08–7.22 (2H, m), 11.7 (1H, s).

Reference Example 32
2-Methoxy-3,5-dimethylbenzaldehyde

To a solution of 1-methoxy-2,4-dimethylbenzene (8.00 g, 58.7 mmol) and 1,1-dichloromethyl methyl ether (7.40 g, 64.7 mmol) in methylene chloride (30 mL) was added titanium tetrachloride (20.0 g, 105 mmol) at 0° C. and the mixture was stirred at that temperature for 20 minutes. This reaction mixture was poured into iced water and the organic layer was taken, washed with saturated aqueous sodium hydrogen carbonate solution, dried over MgSO$_4$, and filtered. The filtrate was concentrated under reduced pressure to provide 9.40 g of the title compound. Yield 98%. Oil.

¹H-NMR (CDCl$_3$) δ: 2.306 (3H, s), 2.312 (3H, s), 3.85 (3H, s), 7.25–7.27 (1H, m), 7.48 (1H, d, J=1.8 Hz), 10.3 (1H, s).

Reference Example 33
(E)-3-(2-methoxy-3,5-dimethylphenyl)propenoic Acid

A solution of 2-methoxy-3,5-dimethylbenzaldehyde (9.40 g, 57.2 mmol), malonic acid (8.90 g, 85.8 mmol), and pyrrolidine (730 mg, 8.58 mmol) in pyridine (80 mL) was refluxed for 14 hours. This reaction mixture was poured in iced water and extracted with ethyl acetate. The extract was washed with 2N-hydrochloric acid, dried over MgSO$_4$, and filtered. The filtrate was concentrated under reduced pressure to provide 9.60 g of the title compound. Yield 81%.

m.p. 178–180° C.

¹H-NMR (CDCl$_3$) δ: 2.28 (3H, s), 2.30 (3H, s), 3.74 (3H, s), 6.49 (1H, d, J=16.0 Hz), 7.07 (1H, s), 7.25 (1H, s), 8.07 (1H, d, J=16.0 Hz), 9.2–12 (1H, br).

Reference Example 34
3-(2-Methoxy-3,5-dimethylphenyl)propionic Acid

In acetic acid (80 mL) were suspended (E)-3-(2-methoxy-3,5-dimethylphenyl)propenoic acid (9.60 g, 46.5 mmol) and 10% palladium-on-carbon (hydrous) (0.60 g) and the suspension was stirred in a hydrogen atmosphere at 60° C. for 14 hours. The catalyst was then filtered off and the filtrate was concentrated under reduced pressure. The residue was crystallized from ethanol to provide 8.90 g of the title compound. Yield 91%.

m.p. 74–75° C.

¹H-NMR (CDCl$_3$) δ: 2.26 (6H, s), 2.61–2.75 (2H, m), 2.87–2.98 (2H, m), 3.72 (3H, s), 6.84 (1H, s), 6.87 (1H, s), 1H not confirmed.

Reference Example 35
2,3-Dihydro-4-methoxy-5,7-dimethyl-1H-inden-1-one

A solution of 3-(2-methoxy-3,5-dimethylphenyl)propionic acid (8.80 g, 42.2 mmol) in thionyl chloride (80 mL) was refluxed for 1.5 hours. After cooling, the reaction mixture was concentrated under reduced pressure and the residue was dissolved in 1,2-dichloroethane (100 mL). To this solution was added anhydrous aluminum chloride (5.80 g, 43.5 mmol) gradually at 0° C. and the mixture was stirred at room temperature for 1.0 hour. After completion of the reaction, the reaction mixture was poured in iced water and extracted with 1,2-dichloroethane. The organic layer was washed serially with 1N-hydrochloric acid, saturated aqueous sodium hydrogen carbonate solution, and water, dried over MgSO$_4$, and filtered. The filtrate was concentrated under reduced pressure to provide 6.90 g of the title compound. Yield 86%. Oil.

¹H-NMR (CDCl₃) δ: 2.32 (3H, s), 2.35 (3H, s), 2.60–2.80 (2H, m), 3.00–3.15 (2H, m), 3.82 (3H, s), 6.92 (1H, s).

Reference Example 36
2,3-Dihydro-4-methoxy-6,7-dimethyl-1H-inden-1-one

Using 1-methoxy-3,4-dimethylbenzene, the procedure of Reference Examples 32–35 was otherwise repeated to synthesize the title compound. Yield 33%.
m.p. 127–128° C. (ethyl acetate-hexane)
¹H-NMR (CDCl₃) δ: 2.31 (3H, s), 2.51 (3H, s), 2.58–2.67 (2H, m), 2.85–2.95 (2H, m), 3.87 (3H, s), 6.84 (1H, s).

Reference Example 37
2,3-Dihydro-8-hydroxy-4H-1-benzopyran-4-one 2,3-Dihydro-8-methoxy-4H-1-benzopyran-4-one (7.59 g, 42.4 mmol) was dissolved in xylene (80 mL) followed by addition of anhydrous aluminum chloride (11.4 g, 85.5 mmol), and the mixture was stirred at 100° C. for 2 hours. After cooling, the reaction mixture was poured into iced water and extracted with ethyl acetate. The organic layer was washed with 1N-hydrochloric acid and saturated aqueous sodium chloride solution, dried over MgSO₄, and filtered. The filtrate was concentrated under reduced pressure and the residue was crystallized from methanol-ethyl acetate-diethyl ether to provide 3.94 g of the title compound. Yield 56%.
m.p. 93–96° C.
¹H-NMR (CDCl₃) δ: 2.86 (2H, t, J=6.4 Hz), 4.63 (2H, t, J=6.4 Hz), 5.72 (1H, s), 6.93 (1H, t, J=8.0 Hz), 7.14 (1H, dd, J=7.8, 1.6 Hz), 7.44 (1H, dd, J=7.8, 1.6 Hz).

Reference Example 38
2,3-Dihydro-4-hydroxy-5,7-dimethyl-1H-inden-1-one

Using 2,3-dihydro-4-methoxy-5,7-dimethyl-1H-inden-1-one, the procedure of Reference Example 37 was otherwise repeated to synthesize the title compound. Yield 78%.
m.p. 152–154° C. (ethyl acetate)
¹H-NMR (DMSO-d₆) δ: 2.21 (3H, s), 2.40 (3H, s), 2.46–2.61 (2H, m), 2.83–2.96 (2H, m), 6.87 (1H, s), 8.81 (1H, s).

Reference Example 39
2,3-Dihydro-4-hydroxy-6,7-dimethyl-1H-inden-1-one

Using 2,3-dihydro-4-methoxy-6,7-dimethyl-1H-inden-1-one, the procedure of Reference Example 37 was otherwise repeated to synthesize the title compound. Yield 92%.
m.p. 171–173° C. (ethyl acetate)
¹H-NMR (DMSO-d₆) δ: 2.18 (3H, s), 2.39 (3H, s), 2.50–2.61 (2H, m), 2.76–2.85 (2H, m), 6.83 (1H, s), 9.41 (1H, s).

Reference Example 40
3,3-Diphenylpropyl Methanesulfonate

To a mixed solution of 3,3-diphenyl-1-propanol (24.0 g, 113 mmol) and methanesulfonyl chloride (13.7 g, 120 mmol) in tetrahydrofuran (200 mL) was added triethylamine (17.0 mL, 120 mmol) gradually at 0° C. and the mixture was stirred at room temperature for 10 minutes. This reaction mixture was diluted with water (200 mL) and extracted with 2 portions of ethyl acetate. The combined organic solution was washed with saturated aqueous sodium chloride solution, dried over MgSO₄, and filtered. The filtrate was concentrated under reduced pressure and the residue was crystallized from diisopropyl ether to provide 25.8 g of the title compound. Yield 79%.
m.p. 83–85° C.
¹H-NMR (CDCl₃) δ: 2.50 (2H, dt, J=8.0, 6.4 Hz), 2.90 (3H, s), 4.08–4.21 (3H, m), 7.13–7.41 (10H, m).

Reference Example 41
2,2-Diphenylethyl Methanesulfonate

Using 2,2-diphenyl-1-ethanol, the procedure of Reference Example 40 was otherwise repeated to synthesize the title compound. Yield 69%.
m.p. 101–102° C. (ethyl acetate-hexane)
¹H-NMR (CDCl₃) δ: 2.73 (3H, s), 4.43 (1H, t, J=7.4 Hz), 4.72 (2H, d, J=7.4 Hz), 7.13–7.43 (10H, m).

Reference Example 42
4,4-Diphenylbutyl Methanesulfonate

Using 4,4-diphenyl-1-butanol, the procedure of Reference Example 40 was otherwise repeated to synthesize the title compound. Yield 68%.
m.p. 85–88° C. (ethyl acetate-hexane)
¹H-NMR (CDCl₃) δ: 1.62–1.81 (2H, m), 2.10–2.23 (2H, m), 2.95 (3H, s), 3.90 (1H, t, J=8.0 Hz), 4.22 (2H, t, J=6.4 Hz), 7.13–7.34 (10H, m).

Reference Example 43
3,3-Diphenylpropyl Iodide

To a solution of sodium iodide (2.80 g, 18.9 mmol) in acetone (20 mL) was added a solution of 3,3-diphenylpropyl methanesulfonate (5.00 g, 17.2 mmol) in acetone (10 mL) at 0° C. and the mixture was refluxed for 3 hours. After cooling, the solvent was distilled off under reduced pressure and the residue was diluted with water (30 mL) and extracted with 2 portions of ethyl acetate. The pooled extract was washed with saturated aqueous sodium chloride solution, dried over MgSO₄, and filtered. The filtrate was concentrated under reduced pressure and the residue was crystallized from methanol to provide 4.70 g of the title compound. Yield 85%.
m.p. 51–55° C.
¹H-NMR (CDCl₃) δ: 2.54 (2H, q, J=7.2 Hz), 3.09 (2H, t, J=7.0 Hz), 4.11 (1H, t, J=7.6 Hz), 7.15–7.40 (10H, m).

Reference Example 44
2,2-Diphenylethyl Iodide

Using 2,2-diphenylethyl methanesulfonate, the procedure of Reference Example 43 was otherwise repeated to synthesize the title compound. Yield 58%.
m.p. 76–78° C. (methanol)
¹H-NMR (CDCl₃) δ: 3.74 (2H, d, J=8.2 Hz), 4.34 (1H, t, J=8.2 Hz), 7.18–7.37 (10H, m).

Reference Example 45
4,4-Diphenylbutyl Iodide

Using 4,4-diphenylbutyl methanesulfonate, the procedure of Reference Example 43 was otherwise repeated to synthesize the title compound. Yield 67%. Oil.
¹H-NMR (CDCl₃) δ: 1.70–1.86 (2H, m), 2.08–2.25 (2H, m), 3.18 (2H, t, J=6.8 Hz), 3.91 (1H, t, J=7.6 Hz), 7.11–7.36 (10H, m).

Reference Example 46
N-(3,3-diphenylpropyl)thiourea

A solution of 3,3-diphenylpropylamine (4.00 g, 18.9 mmol) and ammonium thiocyanate (1.60 g, 20.8 mmol) in bromobenzene (30 mL) was refluxed for 1 hour. After cooling, the solid precipitate was recovered, rinsed with diethyl ether, water, and ethanol, and dried to provide 3.00 g (yield 59%) of the title compound. Amorphous solid.
¹H-NMR (DMSO-d₆) δ: 2.16–2.35 (2H, m), 3.10–3.40 (2H, br), 3.98 (1H, t, J=7.4 Hz), 6.89 (1H, br s), 7.05–7.43 (10H, m), 7.63 (1H, br s), 1H not confirmed.

Reference Example 47

N-(2,2-diphenylethyl)thiourea

Using 2,2-diphenylethylamine, the procedure of Reference Example 46 was otherwise repeated to synthesize the title compound. Yield 59%.

m.p. 205–207° C.

$^1$H-NMR (DMSO-d$_6$) δ: 3.96–4.11 (2H, m), 3.98 (1H, t, J=7.6 Hz), 6.96 (1H, br s), 7.11–7.50 (11H, m), 1H not confirmed.

Reference Example 48

N-(diphenylmethyl)thiourea

Using diphenylmethylamine, the procedure of Reference Example 46 was otherwise repeated to synthesize the title compound. Yield 59%. Amorphous solid.

$^1$H-NMR (DMSO-d$_6$) δ: 6.50–6.72 (1H, m), 7.00–7.52 (12H, m), 8.54 (1H, d, J=8.8 Hz).

Reference Example 49

(2-Naphthyl)phenylmethyl Bromide

To a solution of benzoylnaphthalene (5.00 g, 21.5 mmol) in methanol (30 mL) was added sodium borohydride (400 mg, 10.8 mmol) with ice-cooling and the mixture was stirred at room temperature for 30 minutes. This reaction mixture was diluted with water and extracted with ethyl acetate. The organic layer was washed with water, dried over MgSO$_4$, and filtered and the filtrate was concentrated under reduced pressure to provide 4.80 g of (2-naphthyl)phenylmethanol. To a solution of this compound (4.80 g, 20.5 mmol) in diisopropyl ether (30 mL) was added phosphorus tribromide (3.70 g, 13.7 mmol) with ice-cooling and the mixture was stirred at room temperature for 1 hour. This reaction mixture was diluted with water and extracted with diisopropyl ether. The organic layer was washed with water and saturated aqueous sodium hydrogen carbonate solution, dried over MgSO$_4$, and filtered. The filtrate was concentrated under reduced pressure and the solid residue was recrystallized from diisopropyl ether-hexane to provide 4.10 g of the title compound. Yield 64%.

m.p. 89–90° C.

$^1$H-NMR (CDCl$_3$) δ: 6.45 (1H, s), 7.22–7.61 (8H, m), 7.71–7.86 (4H, m).

Reference Example 50

4-Phenylbenzyl Bromide

To a solution of 4-phenylbenzyl alcohol (1.00 g, 5.43 mmol) in a mixture of diisopropyl ether (10 mL) and chloroform (20 mL) was added phosphorus tribromide (0.98 g, 3.62 mmol) with ice-cooling and the mixture was stirred at room temperature for 1 hour. This reaction mixture was diluted with water and extracted with diisopropyl ether. The organic layer was washed with water and saturated aqueous sodium hydrogen carbonate solution, dried over MgSO$_4$, and filtered. The filtrate was concentrated under reduced pressure and the residue was recrystallized from ethanol-hexane to provide 1.00 g of the title compound. Yield 75%.

m.p. 86–88° C.

$^1$H-NMR (CDCl$_3$) δ: 4.55 (2H, s), 7.32–7.67 (9H, m).

Reference Example 51

(4-Methylphenyl)(phenyl)methyl Bromide

Using (4-methylphenyl)(phenyl)methanol, the procedure of Reference Example 50 was otherwise repeated to synthesize the title compound. Yield 99%. Oil.

$^1$H-NMR (CDCl$_3$) δ: 2.33 (3H, s), 6.28 (1H, s), 7.14 (2H, d, J=8.0 Hz), 7.25–7.49 (7H, m).

Reference Example 52

(4-Chlorophenyl)(phenyl)methyl Bromide

Using (4-chlorophenyl)(phenyl)methanol, the procedure of Reference Example 50 was otherwise repeated to synthesize the title compound. Quantitative. Oil.

$^1$H-NMR (CDCl$_3$) δ: 6.24 (1H, s), 7.25–7.45 (9H, m).

Reference Example 53

Bis(4-chlorophenyl)methyl Bromide

Using bis(4-chlorophenyl)methanol, the procedure of Reference Example 50 was otherwise repeated to synthesize the title compound. Yield 96%. Oil.

$^1$H-NMR (CDCl$_3$) δ: 6.20 (1H, s), 7.26–7.39 (8H, m).

Reference Example 54

1,2-Diphenylethyl Bromide

Using benzyl phenyl ketone, the procedure of Reference Example 49 was otherwise repeated to synthesize the title compound. Yield 57%. Oil.

$^1$H-NMR (CDCl$_3$) δ: 3.39–3.62 (2H, s), 5.13 (1H, t, J=7.6 Hz), 7.06–7.55 (10H, m).

Reference Example 55

(4-Methoxyphenyl)(phenyl)methyl Bromide

Using 4-methoxyphenyl phenyl ketone, the procedure of Reference Example 49 was otherwise repeated to synthesize the title compound. Yield 98%. Oil.

$^1$H-NMR (CDCl$_3$) δ: 3.80 (3H, s), 6.31 (1H, s), 6.84–6.90 (2H, m), 7.24–7.40 (5H, m), 7.45–7.50 (2H, m).

Reference Example 56

Bis(4-fluorophenyl)methyl Bromide

Using bis(4-fluorophenyl) ketone, the procedure of Reference Example 49 was otherwise repeated to synthesize the title compound. Yield 59%. Oil.

$^1$H-NMR (CDCl$_3$) δ: 6.26 (1H, s), 6.98–7.09 (4H, m), 7.37–7.44 (4H, m).

Reference Example 57

(4-Nitrophenyl)(phenyl)methyl Bromide

Using 4-nitrophenyl phenyl ketone, the procedure of Reference Example 49 was otherwise repeated to synthesize the title compound. Quantitative. Oil.

$^1$H-NMR (CDCl$_3$) δ: 6.25 (1H, s), 7.27–7.38 (5H, m), 7.58 (2H, d, J=8.4 Hz), 8.19 (2H, d, J=8.4 Hz).

Reference Example 58

(4-Fluorophenyl)(phenyl)methyl Bromide

Using 4-fluorophenyl phenyl ketone, the procedure of Reference Example 49 was otherwise repeated to synthesize the title compound. Yield 84%. Oil.

$^1$H-NMR (CDCl$_3$) δ: 6.27 (1H, s), 6.97–7.05 (2H, m), 7.01–7.46 (7H, m).

Reference Example 59

(Phenyl)(4-trifluoromethylphenyl)methyl Bromide

Using phenyl 4-trifluoromethylphenyl ketone, the procedure of Reference Example 49 was otherwise repeated to synthesize the title compound. Yield 64%. Oil.

$^1$H-NMR (CDCl$_3$) δ: 6.28 (1H, s), 7.30–7.46 (5H, m), 7.59 (4H, s).

Reference Example 60

(4-Cyanophenyl)(phenyl)methyl Bromide

4-Cyanophenyl phenyl ketone, the procedure of Reference Example 49 was otherwise repeated to synthesize the title compound. Yield 90%. Oil.

$^1$H-NMR (CDCl$_3$) δ: 6.24 (1H, s), 7.30–7.44 (5H, m), 7.53–7.66 (4H, m).

Reference Example 61
(3-Chlorophenyl)(phenyl)methyl Bromide

Using 3-chlorophenyl phenyl ketone, the procedure of Reference Example 49 was otherwise repeated to synthesize the title compound. Yield 62%. Oil.

$^1$H-NMR (CDCl$_3$) δ: 6.03 (1H, s), 7.24–7.45 (9H, m).

Reference Example 62
(2-Chlorophenyl)(phenyl)methyl Bromide

Using 2-chlorophenyl phenyl ketone, the procedure of Reference Example 49 was otherwise repeated to synthesize the title compound. Yield 71%. Oil.

$^1$H-NMR (CDCl$_3$) δ: 6.71 (1H, s,), 7.19–7.70 (9H, m).

Reference Example 63
(3-Methylphenyl)(phenyl)methyl Bromide

Using 3-methylphenyl phenyl ketone, the procedure of Reference Example 49 was otherwise repeated to synthesize the title compound. Yield 94%. Oil.

$^1$H-NMR (CDCl$_3$) δ: 2.34 (3H, s), 6.25 (1H, s), 7.08 (1H, d, J=6.2 Hz), 7.17–7.37 (6H, m), 7.44–7.48 (2H, m).

Reference Example 64
(2-Methylphenyl)(phenyl)methyl Bromide

Using 2-methylphenyl phenyl ketone, the procedure of Reference Example 49 was otherwise repeated to synthesize the title compound. Quantitative. Oil.

$^1$H-NMR (CDCl$_3$) δ: 2.36 (3H, s), 6.49 (1H, s), 7.14–7.56 (9H, m).

Reference Example 65
(Phenyl)(3-trifluoromethylphenyl)methyl Bromide

Using phenyl 3-trifluoromethylphenyl ketone, the procedure of Reference Example 49 was otherwise repeated to synthesize the title compound. Quantitative. Oil.

$^1$H-NMR (CDCl$_3$) δ: 6.49 (1H, s), 7.20–7.49 (9H, m).

Reference Example 66
(2-Fluorophenyl)(phenyl)methyl Bromide

Using 2-fluorophenyl phenyl ketone, the procedure of Reference Example 49 was otherwise repeated to synthesize the title compound. Yield 98%. Oil.

$^1$H-NMR (CDCl$_3$) δ: 6.65 (1H, s), 7.10–7.66 (9H, m).

Reference Example 67
3,4-Dihydro-7-hydroxy-1(2H)-naphthalenone

Using 3,4-dihydro-7-methoxy-1(2H)-naphthalenone, the procedure of Reference Example 37 was otherwise repeated to synthesize the title compound. Yield 89%.

m.p. 170–173° C. (ethyl acetate)

$^1$H-NMR (CDCl$_3$) δ: 1.89–2.11 (2H, m), 2.44–2.63 (2H, m), 2.77–2.86 (2H, m), 6.96 (1H, dd, J=8.0, 3.0 Hz), 7.14 (1H, d, J=8.0 Hz), 7.26 (1H, d, J=3.0 Hz), 9.53 (1H, s).

Reference Example 68
Ethyl[(5,6,7,8-tetrahydro-5-oxo-3-naphthalenyl)oxy]acetate To a solution of 3,4-dihydro-7-hydroxy-1(2H)-naphthalenone (15.3 g, 94.3 mmol) in N,N-dimethylformamide (150 mL) were serially added ethyl bromoacetate (16.5 g, 99.0 mmol) and potassium carbonate (13.7 g, 99.0 mmol) and the mixture was stirred at 60° C. for 6 hours. This reaction mixture was diluted with water and extracted with ethyl acetate. The organic layer was washed with water and saturated aqueous sodium chloride solution, dried over anhydrous magnesium sulfate (MgSO$_4$), filtered, and concentrated under reduced pressure. The residue was crystallized from hexane-ethyl acetate to provide 19.5 g of the title compound. Yield 83%.

m.p. 84–86° C.

$^1$H-NMR (CDCl$_3$) δ: 1.30 (3H, t, J=7.2 Hz), 2.01–2.17 (2H, m), 2.54–2.67 (2H, m), 2.85–2.94 (2H, m), 4.26 (2H, q, J=7.2 Hz), 4.65 (2H, s), 7.08–7.22 (2H, m), 7.45 (1H, d, J=2.6 Hz).

Reference Example 69
Ethyl[(6-bromo-5,6,7,8-tetrahydro-5-oxo-3-naphthalenyl)oxy]acetate Using ethyl[(5,6,7,8-tetrahydro-5-oxo-3-naphthalenyl)oxy]acetate, the procedure of Reference Example 11 was otherwise repeated to synthesize the title compound. Yield 85%.

m.p. 91–93° C. (hexane-ethanol)

$^1$H-NMR (CDCl$_3$) δ: 1.31 (3H, t, J=7.2 Hz), 2.35–2.62 (2H, m), 2.86 (1H, dt, J=17.2, 4.4 Hz), 3.15–3.33 (1H, m), 4.28 (2H, q, J=7.2 Hz), 4.67 (2H, s), 4.72 (1H, t, J=4.4 Hz), 7.15–7.28 (2H, m), 7.49 (1H, d, J=2.2 Hz).

Reference Example 70
Ethyl[(2-mercapto-4,5-dihydronaphtho[1,2-d]thiazol-8-yl)oxy]acetate Using ethyl[(6-bromo-5,6,7,8-tetrahydro-5-oxo-3-naphthalenyl)oxy]acetate, the procedure of Reference Example 21 was otherwise repeated to synthesize the title compound. Yield 72%. Amorphous solid.

$^1$H-NMR (DMSO-d$_6$) δ: 1.24 (3H, t, J=7.0 Hz), 2.66–3.00 (4H, m), 4.19 (2H, q, J=7.0 Hz), 4.76 (2H, s), 6.80 (1H, dd, J=8.0, 2.6 Hz), 7.17 (1H, d, J=8.4 Hz), 7.40 (1H, d, J=2.6 Hz), 13.5 (1H, br s).

Reference Example 71
Phenylthioacetamide

A solution of phenylacetonitrile (10.0 g, 85.4 mmol) and diethyl dithiophosphate (17.5 g, 93.9 mmol) in 4N-HCl/ethyl acetate (400 mL) was stirred at room temperature for 16 hours. This reaction mixture was washed with water and saturated aqueous sodium hydrogen carbonate solution, dried over MgSO$_4$, filtered, and concentrated under reduced pressure. The residue was crystallized from ethanol to provide 7.1 g of the title compound. Yield 55%.

m.p. 98–100° C.

$^1$H-NMR (CDCl$_3$) δ: 4.08 (2H, s), 6.50–7.10 (1H, br), 7.22–7.45 (5H, m), 7.90–8.40 (1H, br).

Reference Example 72
Diphenylthioacetamide

Using diphenylacetonitrile, the procedure of Reference Example 71 was otherwise repeated to synthesize the title compound. Yield 67%.

m.p. 152–155° C. (ethanol)

$^1$H-NMR (CDCl$_3$) δ: 5.62 (1H, s), 6.60–7.10 (1H, br), 7.15–7.43 (10H, m), 7.83–8.30 (1H, br).

Reference Example 73
Diphenylthiopropionamide

A solution of 3,3-diphenylpropionic acid (15.0 g, 66.3 mmol) in thionyl chloride (15 mL) was refluxed for 1 hour. After cooling, the reaction mixture was concentrated under reduced pressure. The residue was added to 25% aqueous ammonia (30 mL) gradually at 0° C. and the mixture was stirred at room temperature for 30 minutes. This reaction mixture was extracted with 2 portions of ethyl acetate and the pooled organic layer was washed with saturated aqueous sodium chloride solution, dried over MgSO$_4$, filtered, and concentrated under reduced pressure to provide 13.0 g of diphenylpropionamide. To a solution of this compound (5.00 g, 22.2 mmol) in tetrahydrofuran (80 mL) was added phosphorus pentasulfide (6.30 g, 28.3 mmol), and the mixture was refluxed for 2 hours. After cooling, the reaction mixture was diluted with water and extracted with 2 portions of ethyl acetate. The pooled organic layer was washed with saturated aqueous sodium chloride solution, dried over $MgSO_4$, filtered, and concentrated under reduced pressure. The residue was crystallized from ethanol to provide 1.5 g of the title compound. Yield 24%.

m.p. 150–152° C.

$^1$H-NMR (CDCl$_3$) δ: 3.38 (2H, d, J=7.8 Hz), 4.67 (1H, t, J=7.8 Hz), 6.40–6.7 (1H, br), 7.18–7.47 (11H, m).

Reference Example 74
Bis(3-fluorophenyl)methylbromide

To a solution of 1-bromo-3-fluorobenzene (10.0 g, 57.1 mmol) in tetrahydrofuran (100 mL) was added n-BuLi (1.6M, 35.7 mL, 62.8 mmol) at −78° C. and the mixture was stirred at that temperature for 20 minutes. To the mixture was added 3-fluorobenzaldehyde (7.80 g, 62.8 mmol) and the resulting mixture was stirred at room temperature for 30 minutes. To this mixture was added water and the product was extracted with ethyl acetate. The extract was washed with water, dried over $MgSO_4$, and filtered. The filtrate was concentrated under reduced pressure to provide 10.1 g of bis(3-fluorophenyl)methanol. To a solution of this compound (6.60 g, 30.0 mmol) in diisopropylether (50 mL) was added phosphorus tribromide (5.41 g, 20.0 mmol) with ice-cooling and the mixture was stirred at that temperature for 1 hour. This reaction mixture was diluted with water and extracted with diisopropylether. The organic layer was washed with water and saturated with aqueous sodium hydrogen carbonate solution, dried over $MgSO_4$, and filtered. The filtrate was concentrated under reduced pressure to provide 5.61 g of the title compound. Yield 53%. Oil.

$^1$H-NMR (CDCl$_3$) δ: 6.26 (1H, s), 6.98–7.09 (4H, m) 7.37–7.44 (4H, m).

Reference Example 75
Bis(2-fluorophenyl)methylbromide

Using 1-bromo-2-fluorobenzene and 2-fluorobenzaldehyde, the procedure of Reference Example 74 was otherwise repeated to synthesize the title compound. Yield 65%. Oil.

$^1$H-NMR (CDCl$_3$) δ: 6.77 (1H, s), 6.96–7.36 (6H, m), 7.50–7.60 (2H, m).

Reference Example 76
Methyl[2,3-bis(ethoxycarbonylmethoxy)]benzoate

To a solution of 2,3-dihydroxybenzoic acid (33.0 g, 214 mmol) in methanol (200 mL) was added sulfuric acid (5.0 mL) and the mixture was refluxed for 14 hours. The solvent was then distilled off under reduced pressure. To that residue was added water, and the mixture was extracted with ethyl acetate. The organic layer was washed with water, dried over $MgSO_4$, and filtered. The filtrate was concentrated under reduced pressure to provide 35.0 g of methyl 2,3-dihydroxybenzoate. A mixture of this compound (35.0 g, 208 mmol), ethyl bromoacetate (70.0 g, 420 mmol), and potassium carbonate (58.0 g, 420 mmol) in acetone (400 mL) was stirred for 14 hours, and filtered. The filtrate was concentrated under reduced pressure to provide 58.0 g of the title compound. Yield 80%. Oil.

$^1$H-NMR (CDCl$_3$) δ: 1.18–1.45 (6H, m), 3.90 (3H, s), 4.14–4.38 (4H, m), 4.69 (2H, s), 4.78 (2H, s), 6.97–7.14 (2H, m), 7.40 (1H, dd, J=7.6, 1.8 Hz).

Reference Example 77
[2,3-Bis(carboxymethoxy)]benzoic Acid

To a solution of methyl[2,3-bis(ethoxycarbonylmethoxy)] benzoate (58.0 g, 170 mmol) in methanol (100 mL) at 60° C. was added 3N-aqueous sodium hydroxide solution over 30 minutes, and the reaction mixture was refluxed for 2 hours. The solvent was then distilled off under reduced pressure. To that residue was added 4N-hydrochloric acid. The crystal was collected with filtration, and dried to provide 31.3 g of the title compound. Yield 68%.

m. p. 195–197° C.

$^1$H-NMR (DMSO-d$_6$) δ: 4.67 (2H, s), 4.75 (2H, s), 7.00–7.27 (3H, m), 3H not confirmed.

Reference Example 78
Ethyl[(3-oxo-2,3-dihydrobenzofuran-7-yl)oxy]acetate

A mixture of [2,3-bis(carboxymethoxy)]benzoic acid (10.0 g, 37.0 mmol), sodium acetate (4.55 g, 55.5 mmol), and acetic acid (7.0 mL) in acetic anhydride (50 mL) was refluxed for 4 hours. The solvent was then distilled off under reduced pressure. To that residue was added water, and the mixture was extracted with ethyl acetate twice. The organic layer was washed with water, dried over $MgSO_4$, and filtered. The filtrate was concentrated under reduced pressure to provide 6.10 g of [(3-acetoxybenzofuran-7-yl)oxy] acetate. To a solution of this compound (5.80 g, 23.2 mmol) in ethanol (20 mL) was added sulfuric acid (1.0 mL) and refluxed for 30 minutes. The solvent was then distilled off under reduced pressure. To that residue was added water, and the mixture was extracted with ethyl acetate. The organic layer was washed with water, dried over $MgSO_4$, and filtered. The filtrate was concentrated under reduced pressure, and the residue was purified by silica gel column chromatography (ethyl acetate-hexane 1:8) to provide 3.0 g of the title compound. Yield 36%.

m. p. 89–90° C. (ethyl acetate-hexane)

$^1$H-NMR (CDCl$_3$) δ: 1.30 (3H, t, J=6.8 Hz), 4.28 (2H, q, J=6.8 Hz), 4.69 (2H, s), 4.79 (2H, s), 6.98–7.13 (2H, m), 7.32 (1H, dd, J=7.4, 1.2 Hz).

Reference Example 79
(3-Fluorophenyl)(phenyl)methylbromide

Using 3-fluorophenyl phenyl ketone, the procedure of Reference Example 49 was otherwise repeated to synthesize the title compound. Yield 73%. Oil.

$^1$H-NMR(CDCl$_3$) δ: 6.23 (1H, s), 6.90–7.02 (1H, m), 7.10–7.49 (8H, m).

Example 1
[[2-(2,2-Diphenylethyl)thio-4,5-dihydronaphtho[1,2-d] thiazol-6-yl]oxy]acetic Acid To a solution of ethyl[(2-mercapto-4,5-dihydronaphtho[1,2-d]thiazol-6-yl)oxy]acetate (1.80 g, 5.60 mmol) in N,N-dimethylformamide (15 mL) was added 2,2-diphenylethyl methanesulfonate (1.80 g, 6.20 mmol) followed by addition of potassium carbonate (857 mg, 6.20 mmol) and the mixture was stirred at 60° C. for 2 hours. This reaction mixture was diluted with water and extracted with ethyl acetate. The organic layer was washed with water and saturated aqueous sodium chloride solution, dried over $MgSO_4$, and filtered. The filtrate was concentrated under reduced pressure to provide 2.70 g of ethyl[[2-(2,2-diphenylethyl)thio-4,5-dihydronaphtho[1,2-d]thiazol-6-yl] oxy]acetate. To a solution of this compound (0.70 g, 1.44 mmol) in a mixture of tetrahydrofuran (8 mL) and methanol (2 ml) was added 1N-aqueous sodium hydroxide solution (1.5 mL) dropwise and the mixture was stirred at room temperature for 5 minutes. The solvent was then distilled off under reduced pressure. To the residue was added 1N-hydrochloric acid, and the mixture was extracted with ethyl acetate. The organic layer was washed with water and saturated aqueous sodium chloride solution, dried over MgSO$_4$, and filtered. The filtrate was concentrated under reduced pressure and the residue was recrystallized from ethyl acetate-hexane to provide 0.43 g of the title compound. Yield 61%.

m.p. 223–2250° C.

$^1$H-NMR (DMSO-d$_6$) δ: 2.90–3.15 (4H, m), 3.84 (2H, d, J=8.0 Hz), 4.48 (1H, t, J=8.0 Hz), 4.71 (2H, s), 6.83 (1H, d, J=8.0 Hz), 7.13–7.49 (12H, m), 1H not confirmed.

Example 2

[(2-Benzylthio-8H-indeno[1,2-d]thiazol-7-yl)oxy]acetic Acid

Using ethyl[(2-mercapto-8H-indeno[1,2-d]thiazol-7-yl)oxy]acetate and benzyl bromide, the procedure of Example 1 was otherwise repeated to synthesize the title compound. Yield 21%.

m.p. 166–169° C. (diethyl ether-ethanol)

$^1$H-NMR (CDCl$_3$) δ: 3.78 (2H, s), 4.43 (2H, s), 4.79 (2H, s), 6.70 (1H, d, J=7.8 Hz), 7.24–7.50 (7H, m), 7.8–8.2 (1H, br).

Example 3

[(2-Benzylthio-4,5-dihydronaphtho[1,2-d]thiazol-6-yl)oxy]acetic Acid

Using ethyl[(2-mercapto-4,5-dihydronaphtho[1,2-d]thiazol-6-yl)oxy]acetate and benzyl bromide, the procedure of Example 1 was otherwise repeated to synthesize the title compound. Yield 44%.

m.p. 180–182° C. (ethanol)

$^1$H-NMR (CDCl$_3$) δ: 2.86–3.02 (2H, m), 3.04–3.20 (2H, m), 4.45 (2H, s), 4.73 (2H, s), 6.73 (1H, d, J=8.4 Hz), 6.95 (1H, br s), 7.19–7.42 (6H, m), 7.66 (1H, d, J=7.4 Hz).

Example 4

[(2-(3-Phenyl-2-propenyl)thio-8H-indeno[1,2-d]thiazol-7-yl)oxy]acetic Acid

Using ethyl[(2-mercapto-8H-indeno[1,2-d]thiazol-7-yl)oxy]acetate and 3-bromo-1-phenyl-1-propene, the procedure of Example 1 was otherwise repeated to synthesize the title compound. Yield 50%.

m.p. 172–174° C. (ethanol)

$^1$H-NMR (DMSO-d$_6$) δ: 3.83 (2H, s), 4.11 (2H, d, J=7.6 Hz), 4.79 (2H, s), 6.32–6.51 (1H, m), 6.69 (1H, d, J=15.8 Hz), 6.84 (1H, dd, J=7.0, 2.2 Hz), 7.18–7.45 (7H, m), 1H not confirmed.

Example 5

[(2-(3-Phenyl-2-propenyl)thio-4,5-dihydronaphtho[1,2-d]thiazol-6-yl)oxy]acetic Acid Using ethyl[(2-mercapto-4,5-dihydronaphtho[1,2-d]thiazol-6-yl)oxy]acetate and 3-bromo-1-phenyl-1-propene, the procedure of Example 1 was otherwise repeated to synthesize the title compound. Yield 56%.

m.p. 171–172° C. (ethanol)

$^1$H-NMR (CDCl$_3$) δ: 2.90–3.20 (4H, m), 4.03 (2H, d, J=6.8 Hz), 4.40–5.10 (3H, m), 6.25–6.44 (1H, m), 6.62 (1H, d, J=15.4 Hz), 6.73 (1H, d, J=8.0 Hz), 7.18–7.43 (6H, m), 7.67 (1H, d, J=7.8 Hz).

Example 6

[(2-(3,3-Diphenylpropyl)thio-8H-indeno[1,2-d]thiazol-7-yl)oxy]acetic Acid

Using ethyl[(2-mercapto-8H-indeno[1,2-d]thiazol-7-yl)oxy]acetate and 3,3-diphenylpropyl iodide, the procedure of Example 1 was otherwise repeated to synthesize the title compound. Yield 34%.

m.p. 100–103° C. (ethanol)

$^1$H-NMR (CDCl$_3$) δ: 2.44–3.03 (2H, m), 3.10–3.22 (2H, m), 3.81 (2H, s), 4.17 (1H, t, J=8.0 Hz), 4.60–5.40 (1H, br), 4.78 (2H, s), 6.71 (1H, d, J=8.0 Hz), 7.10–7.52 (12H, m).

Example 7

[(2-(3,3-Diphenylpropyl)thio-4,5-dihydronaphtho[1,2-d]thiazol-6-yl)oxy]acetic Acid Using ethyl[(2-mercapto-4,5-dihydronaphtho[1,2-d]thiazol-6-yl)oxy]acetate and 3,3-diphenylpropyl iodide, the procedure of Example 1 was otherwise repeated to synthesize the title compound. Yield 34%.

m.p. 128–130° C. (ethanol)

$^1$H-NMR (CDCl$_3$) δ: 2.45–2.63 (2H, m), 2.88–3.02 (2H, m), 3.07–3.21 (4H, m), 4.16 (1H, t, J=7.8 Hz), 4.72 (2H, s), 5.00–5.75 (1H, br), 6.72 (1H, d, J=8.0 Hz), 7.12–7.40 (11H, m), 7.59 (1H, d, J=7.8 Hz).

Example 8

[[2-(2,2-Diphenylethyl)thio-8H-indeno[1,2-d]thiazol-7-yl)oxy]acetic Acid

Using ethyl[(2-mercapto-8H-indeno[1,2-d]thiazol-7-yl)oxy]acetate and 2,2-diphenylethyl methanesulfonate, the procedure of Example 1 was otherwise repeated to synthesize the title compound. Yield 37%.

m.p. 207–210° C. (methanol)

$^1$H-NMR (DMSO-d$_6$) δ: 3.84 (2H, s), 4.03 (2H, d, J=8.0 Hz), 4.46 (1H, t, J=8.0 Hz), 4.81 (2H, s), 6.84 (1H, d, J=7.4 Hz), 7.16–7.45 (12H, m), 1H not confirmed.

Example 9

[[2-(4,4-Diphenylbutyl)thio-4,5-dihydronaphtho[1,2-d]thiazol-6-yl]oxy]acetic Acid Using ethyl[(2-mercapto-4,5-dihydronaphtho[1,2-d]thiazol-6-yl)oxy]acetate and 4,4-diphenylbutyl iodide, the procedure of Example 1 was otherwise repeated to synthesize the title compound. Yield 43%.

m.p. 136–138° C. (ethyl acetate-hexane)

$^1$H-NMR (CDCl$_3$) δ: 1.70–1.88 (2H, m), 2.11–2.21 (2H, m), 2.90–3.02 (2H, m), 3.07–3.29 (4H, m), 3.88–4.50 (2H, m), 4.74 (2H, s), 6.73 (1H, d, J=7.4 Hz), 7.10–7.32 (11H, m), 7.60 (1H, t, J=7.0 Hz).

Example 10

[[2-(3,3-Diphenylpropyl)thio-4,5-dihydronaphtho[1,2-d]thiazol-7-yl]oxy]acetic Acid Using ethyl[(2-mercapto-4,5-dihydronaphtho[1,2-d]thiazol-7-yl)oxy]acetate and 3,3-diphenylpropyl iodide, the procedure of Example 1 was otherwise repeated to synthesize the title compound. Yield 54%.

m.p. 138–140° C. (ethyl acetate-hexane)

$^1$H-NMR (CDCl$_3$) δ: 2.45–2.62 (2H, m), 2.86–3.22 (6H, m), 4.16 (1H, t, J=7.8 Hz), 4.70 (2H, s), 5.60–6.50 (1H, br), 6.75–6.86 (2H, m), 7.16–7.38 (10H, m), 7.75–7.85 (1H, m).

Example 11

[[2-(3,3-Diphenylpropyl)thio-4H-[1]benzopyrano[4,3-d]thiazol-6-yl]oxy]acetic Acid Using ethyl[(2-mercapto-4H-[1]benzopyrano[4,3-d]thiazol-6-yl)oxy]acetate and 3,3-diphenylpropyl iodide, the procedure of Example 1 was otherwise repeated to synthesize the title compound. Yield 45%.

m.p. 112–114° C. (ethyl acetate-diisopropyl ether)

$^1$H-NMR (CDCl$_3$) δ: 2.50–2.61 (2H, m), 3.18 (2H, t, J=7.8 Hz), 3.30–4.40 (1H, br), 4.15 (1H, t, J=7.8 Hz), 4.72 (2H, s), 5.47 (2H, s), 6.86 (1H, d, J=8.0 Hz), 6.98 (1H, t, J=8.0 Hz), 7.15–7.30 (10H, m), 7.49 (1H, d, J=8.0 Hz).

Example 12
[[2-(2,2-Diphenylethyl)thio-4H-[1]benzopyrano[4,3-d]thiazol-6-yl]oxy]acetic Acid Using ethyl[(2-mercapto-4H-[1]benzopyrano[4,3-d]thiazol-6-yl)oxy]acetate and 2,2-diphenylethyl iodide, the procedure of Example 1 was otherwise repeated to synthesize the title compound. Yield 41%.

m.p. 182–184° C. (methanol-ethyl acetate)

$^1$H-NMR (CDCl$_3$) δ: 4.00 (2H, d, J=8.0 Hz), 4.46 (1H, t, J=8.0 Hz), 4.68 (2H, s), 5.44 (2H, s), 6.84–6.99 (2H, m), 7.12–7.40 (11H, m), 12.00–13.00 (1H, br).

Example 13
[(2-Diphenylmethylthio-4H-[1]benzopyrano[4,3-d]thiazol-6-yl)oxy]acetic Acid Using ethyl[(2-mercapto-4H-[1]benzopyrano[4,3-d]thiazol-6-yl)oxy]acetate and bromodiphenylmethane, the procedure of Example 1 was otherwise repeated to synthesize the title compound. Yield 17%.

m.p. 129–131° C. (ethyl acetate-hexane)

$^1$H-NMR (CDCl$_3$) δ: 1.60–2.80 (1H, br), 4.68 (2H, s), 5.39 (2H, s), 6.07 (1H, s), 6.84 (1H, d, J=7.8 Hz), 6.96 (1H, t, J=7.8 Hz), 7.26–7.49 (11H, m).

Example 14
[[2-(4-Phenylbenzylthio)-4,5-dihydronaphtho[1,2-d]thiazol-6-yl]oxy]acetic Acid Using ethyl[(2-mercapto-4,5-dihydronaphtho[1,2-d]thiazol-6-yl)oxy)acetate and 4-phenylbenzyl bromide, the procedure of Example 1 was otherwise repeated to synthesize the title compound. Yield 68%.

m.p. 198–200° C. (ethyl acetate-hexane)

$^1$H-NMR (CDCl$_3$) δ: 2.90–3.04 (2H, m), 3.11–3.22 (2H, m), 3.40–4.30 (1H, br), 4.50 (2H, s), 4.74 (2H, s), 6.74 (1H, d, J=8.2 Hz), 7.21–7.62 (10H, m), 7.69 (1H, d, J=7.6 Hz).

Example 15
[[2-(2-Naphthyl)phenylmethylthio-4,5-dihydronaphtho[(1,2-d]thiazol-6-yl]oxy]acetic Acid Using ethyl[(2-mercapto-4,5-dihydronaphtho[1,2-d]thiazol-6-yl)oxy]acetate and (2-naphthyl)phenylmethyl bromide, the procedure of Example 1 was otherwise repeated to synthesize the title compound. Yield 44%.

m.p. 118–121° C. (ethyl acetate-hexane)

$^1$H-NMR (CDCl$_3$) δ: 2.70–2.89 (2H, m), 2.99–3.08 (2H, m), 4.4–4.9 (3H, m), 6.22 (1H, s), 6.69 (1H, d, J=8.0 Hz), 7.24–7.62 (10H, m), 7.76–7.83 (3H, m), 7.91 (1H, s).

Example 16
[[(2-Diphenylmethylthio-4,5-dihydronaphtho[1,2-d]thiazol-7-yl)oxy]acetic Acid Using ethyl[(2-mercapto-4,5-dihydronaphtho[1,2-d]thiazol-7-yl)oxy]acetate and diphenylmethane bromide, the procedure of Example 1 was otherwise repeated to synthesize the title compound. Yield 50%.

m.p. 193–195° C. (ethyl acetate)

$^1$H-NMR (CDCl$_3$) δ: 2.75–2.98 (4H, m), 4.70 (2H, s), 6.01 (1H, s), 6.00–6.60 (1H, br), 6.74–6.82 (2H, m), 7.20–7.55 (10H, m), 7.80 (1H, d, J=8.8 Hz).

Example 17
[[2-(2-Naphthyl)phenylmethylthio-4H-[1]benzopyrano[4,3-d]thiazol-6-yl]oxy]acetic Acid Using ethyl[(2-mercapto-4H-[1]benzopyrano(4,3-d]thiazol-6-yl)oxy]acetate and (2-naphthyl)phenylmethyl bromide, the procedure of Example 1 was otherwise repeated to synthesize the title compound. Yield 45%. Amorphous solid.

$^1$H-NMR (CDCl$_3$) δ: 2.40–3.80 (1H, br), 4.69 (2H, s), 5.36 (2H, s), 6.24 (1H, s), 6.84 (1H, d, J=7.8 Hz), 6.96 (1H, d, J=7.8 Hz), 7.20–7.63 (9H$_1$ m), 7.80–7.84 (3H, m), 7.93 (1H, s).

Example 18
[[2-(4,4-Diphenylbutyl)thio-8H-indeno[1,2-d]thiazol-7-yl]oxy]acetic Acid Using ethyl[(2-mercapto-8H-indeno[1,2-d]thiazol-7-yl)oxy]acetate and 4,4-diphenylbutyl iodide, the procedure of Example 1 was otherwise repeated to synthesize the title compound. Yield 44%.

m.p. 110–112° C. (ethyl acetate-hexane)

$^1$H-NMR (CDCl$_3$) δ: 1.60–1.85 (2H, m), 2.10–2.31 (2H, m), 3.15–3.30 (2H, m), 3.72–3.96 (3H, m), 4.78 (2H, s), 6.69 (1H, d, J=8.0 Hz), 7.07–7.37 (11H, m), 7.43 (1H, d, J=7.6 Hz), 8.10–8.56 (1H, m).

Example 19
4-[[2-(2,2-Diphenylethyl)thio-8H-indeno[1,2-d]thiazol-7-yl]oxy]butyric Acid Using ethyl 4-[(2-mercapto-8H-indeno[1,2-d]thiazol-7-yl)oxy]butyrate and 2,2-diphenylethyl methanesulfonate, the procedure of Example 1 was otherwise repeated to synthesize the title compound. Yield 35%.

m.p. 137–138° C. (ethyl acetate-hexane)

$^1$H-NMR (CDCl$_3$) δ: 1.58–2.01 (1H, br), 2.12–2.25 (2H, m), 2.63 (2H, t, J=7.2 Hz), 3.73 (2H, s), 3.95 (2H, d, J=8.0 Hz), 4.15 (2H, d, J=6.0 Hz), 4.47 (1H, t, J=8.0 Hz), 6.79 (1H, d, J=6.6 Hz), 7.18–7.43 (12H, m).

Example 20
4-[[2-(3,3-Diphenylpropyl)thio-8H-indeno[1,2-d]thiazol-7-yl]oxy]butyric Acid Using 4-[(2-mercapto-8H-indeno(1,2-d]thiazol-7-yl]oxy]butyrate and 3,3-diphenylpropyl iodide, the procedure of Example 1 was otherwise repeated to synthesize the title compound. Yield 27%.

m.p. 86–88° C. (ethyl acetate-hexane)

$^1$H-NMR (CDCl$_3$) δ: 2.12–2.25 (2H, m), 2.47–2.71 (4H, m), 3.08–3.22 (2H, m), 3.72 (2H, s), 4.09–4.25 (3H, m), 6.78 (1H, dd, J=7.8 1.0 Hz), 7.12–7.43 (13H, m).

Example 21
[(2-Diphenylmethylthio-4,5-dihydronaphtho[1,2-d]thiazol-6-yl)oxy]acetic Acid To a solution of ethyl[(2-mercapto-4,5-dihydronaphtho[1,2-d]thiazol-6-yl)oxy]acetate (1.10 g, 3.42 mmol) in N,N-dimethylformamide (20 mL) were added diphenylmethane bromide (0.93 g, 3.76 mmol) and potassium carbonate (0.52 g, 3.76 mmol), and the mixture was stirred at 60° C. for 3 hours. This reaction mixture was diluted with ethyl acetate and water and, after phase separation, the aqueous layer was extracted with ethyl acetate. The pooled organic solution was washed with water, dried over MgSO$_4$, and filtered. The filtrate was concentrated under reduced pressure and the residue was dissolved in acetic acid (20 mL). To this solution was added concentrated sulfuric acid (10 ml), and the mixture was refluxed for 1 hour. After cooling, the reaction mixture was diluted with water and extracted with 2 portions of ethyl acetate. The pooled extract was washed with water, dried over MgSO$_4$, and filtered. The filtrate was concentrated under reduced pressure and the residue was crystallized from hexane-ethyl acetate to provide 0.58 g of the title compound. Yield 37%.

m.p. 176–179° C.

$^1$H-NMR (DMSO-d$_6$) δ: 2.80–3.08 (4H, m), 4.70 (2H, s), 6.18 (1H, s), 6.82 (1H, d, J=8.4 Hz), 7.15–7.63 (12H, m), 1H not confirmed.

Example 22
3-[[2-(2,2-Diphenylethyl)thio-4,5-dihydronaphtho[1,2-d]thiazol-6-yl]oxy]propionic Acid Using ethyl 3-[(2-mercapto-4,5-dihydronaphtho[1,2-d]thiazol-6-yl)oxy]propionate and 2,2-diphenylethyl iodide, the procedure of Example 21 was otherwise repeated to synthesize the title compound. Yield 29%.

m.p. 123–125° C. (ethyl acetate-hexane)

$^1$H-NMR (CDCl$_3$) δ: 2.78–3.12 (6H, m), 3.93 (2H, d, J=8.0 Hz), 4.29 (1H, t, J=6.2 Hz), 4.50 (1H, t, J=8.0 Hz), 4.80–6.60 (1H, br), 6.82 (1H, d, J=8.0 Hz), 7.13–7.38 (12H, m), 7.60 (1H, d, J=7.2 Hz).

Example 23
3-[[2-(3,3-Diphenylpropyl)thio-8H-indeno[1,2-d]thiazol-7-yl)oxy]propionic Acid Using ethyl 3-[(2-mercapto-8H-indeno[1,2-d]thiazol-7-yl)oxy]propionate and 3,3-diphenylpropyl iodide, the procedure of Example 21 was otherwise repeated to synthesize the title compound. Yield 49%.

m.p. 113–114° C. (ethyl acetate-diethyl ether)

$^1$H-NMR (CDCl$_3$) δ: 2.42–2.61 (2H, m), 2.82–2.98 (2H, m), 3.09–3.21 (2H, m), 3.70 (2H, s), 4.17 (1H, t, J=8.0 Hz), 4.33–4.43 (2H, m), 6.81 (1H, d, J=7.6 Hz), 7.15–7.44 (13H, m).

Example 24
[[2-(3,3-Diphenylpropyl)thio-8H-indeno[1,2-d]thiazol-6-yl]oxy]acetic Acid Using ethyl[(2-mercapto-8H-indeno[1,2-d]thiazol-6-yl)oxy]acetate and 3,3-diphenylpropyl iodide, the procedure of Example 21 was otherwise repeated to synthesize-the title compound. Yield 42%.

m.p. 135–137° C. (ethyl acetate-diethyl ether)

$^1$H-NMR (CDCl$_3$) δ: 2.45–2.58 (2H, m), 3.07–3.19 (2H, m), 3.74 (2H, s), 3.80–4.43 (2H, m), 4.72 (2H, s), 6.87–6.95 (1H, m), 7.08–7.33 (11H, m), 7.64 (1H, d, J=8.4 Hz).

Example 25
[[2-(3,3-Diphenylpropyl)thio-4,6-dimethyl-8H-indeno[1,2-d]thiazol-7-yl]oxy]acetic Acid Using ethyl[(2-mercapto-4,6-dimethyl-8H-indeno[(1,2-d]thiazol-7-yl)oxy]acetate and 3,3-diphenylpropyl iodide, the procedure of Example 21 was otherwise repeated to synthesize the title compound. Yield 55%.

m.p. 156–158° C. (ethyl acetate-hexane)

$^1$H-NMR (CDCl$_3$) δ: 2.33 (3H, s), 2.50–2.68 (5H, m), 3.11–3.20 (2H, m), 3.3–4.0 (3H, m), 4.18 (1H, t, J=8.0 Hz), 4.62 (2H, s), 6.99 (1H, s), 7.13–7.42 (10H, m).

Example 26
[[2-(3,3-Diphenylpropyl)thio-4,5-dimethyl-8H-indeno[1,2-d]thiazol-7-yl]oxy]acetic Acid Using ethyl[(2-mercapto-4,5-dimethyl-8H-indeno[1,2-d]thiazol-7-yl)oxy]acetate and 3,3-diphenylpropyl iodide, the procedure of Example 21 was otherwise repeated to synthesize the title compound. Yield 53%.

m.p. 142–144° C. (ethyl acetate-hexane)

$^1$H-NMR (CDCl$_3$) δ: 2.33 (3H, s), 2.50–2.72 (5H, m), 3.10–3.21 (2H, m), 3.73 (2H, m), 4.18 (1H, t, J=8.0 Hz), 4.76 (2H, s), 6.53 (1H, s), 6.7–7.7 (11H, m).

Example 27
[(2-Diphenylmethylthio-8H-indeno[1,2-d]thiazol-7-yl)oxy]acetic Acid Using ethyl[(2-mercapto-8H-indeno[1,2-d]thiazol-7-yl)oxy]acetate and diphenylmethane bromide, the procedure of Example 21 was otherwise repeated to synthesize the title compound. Yield 61%.

m.p. 224–225° C. (chloroform-diethyl ether)

$^1$H-NMR (DMSO-d$_6$) δ: 3.76 (2H, s), 4.78 (2H, s), 6.17 (1H, s), 6.78–6.85 (1H, m), 7.10–7.42 (8H, m), 7.50 (4H, d, J=7.0 Hz), 1H not confirmed.

Example 28
3-[(2-Diphenylmethylthio-4,5-dihydronaphtho[1,2-d]thiazol-6-yl)oxy]propionic Acid Using ethyl 3-[(2-mercapto-4,5-dihydronaphtho[1,2-d]thiazol-6-yl)oxy]propionate and diphenylmethane bromide, the procedure of Example 21 was otherwise repeated to synthesize the title compound. Yield 39%.

m.p. 156–158° C. (ethyl acetate-hexane)

$^1$H-NMR (CDCl$_3$) δ: 2.75–3.00 (6H, m), 4.27 (2H, t, J=6.2 Hz), 6.05 (1H, t, J=8.0 Hz), 6.80 (1H, d, J=8.4 Hz), 7.16–7.57 (13H, m).

Example 29
[[2-(2,2-Diphenylethyl)sulfonyl-4,5-dihydronaphtho[1,2-d]thiazol-6-yl]oxy]acetic Acid To a solution of ethyl[(2-mercapto-4,5-dihydronaphtho[1,2-d]thiazol-6-yl)oxy]acetate (1.80 g, 5.60 mmol) in N,N-dimethylformamide (15 mL) was added 2,2-diphenylethyl methanesulfonate (1.80 g, 6.20 mmol) followed by addition of potassium carbonate (857 mg, 6.20 mmol), and the mixture was stirred at 60° C. for 2 hours. This reaction mixture was diluted with water and extracted with ethyl acetate. The organic layer was washed with water and saturated aqueous sodium chloride solution, dried over MgSO$_4$, and filtered. The filtrate was concentrated under reduced pressure to provide 2.70 g of ethyl[[2-(2,2-diphenylethyl)thio-4,5-dihydronaphtho[1,2-d]thiazol-6-yl]oxy]acetate. To a solution of this compound (2.00 g, 3.99 mmol) in ethanol (8 mL)-water (2 mL) was added sodium periodate (4.30 g, 19.9 mmol) and the mixture was refluxed for 14 hours. This reaction mixture was diluted with ethyl acetate and water and, after phase separation, the aqueous layer was extracted with ethyl acetate. The pooled organic solution was washed with water, dried over MgSO$_4$, and filtered and the filtrate was concentrated under reduced pressure. To a solution of the above concentration residue in tetrahydrofuran (16 mL)-methanol (4 mL) was added 1N-aqueous sodium hydroxide solution (2 mL) dropwise, and the mixture was stirred at room temperature for 10 minutes. The solvent was then distilled off under reduced pressure. To the residue was added 1N-hydrochloric acid, and the mixture was extracted with ethyl acetate. The organic layer was washed with water and saturated aqueous sodium chloride solution, dried over MgSO$_4$, and filtered and the filtrate was concentrated under reduced pressure. The residue was recrystallized from ethyl acetate-hexane to provide 0.72 g of the title compound. Yield 41%.

m.p. 168–170° C.

$^1$H-NMR (CDCl$_3$) δ: 2.88–3.02 (2H, m), 3.05–3.20 (2H, m), 3.20–3.80 (1H, br), 4.30 (2H, d, J=7.4 Hz), 4.65–4.80 (3H, m), 6.80 (1H, d, J=8.6 Hz), 7.00–7.32 (11H, m), 7.64 (1H, d, J=7.2 Hz).

Example 30
[[2-(3-Phenyl-2-propenyl)sulfonyl-8H-indeno[1,2-d]thiazol-7-yl]oxy]acetic Acid Using ethyl[(2-mercapto-8H-indeno[1,2-d]thiazol-7-yl)oxy]acetate and 3-bromo-1-phenyl-1-propene, the procedure of Example 29 was otherwise repeated to synthesize the title compound. Yield 8%.

m.p. 212–214° C. (ethyl acetate-hexane)

$^1$H-NMR (CDCl$_3$) δ: 3.30–3.65 (1H, br), 3.95 (2H, s), 4.34 (2H, d, J=7.4 Hz), 4.81 (2H, s), 6.10–6.24 (1H, m), 6.56

(1H, d, J=16.2 Hz), 6.79 (1H, d, J=8.0 Hz), 7.23–7.31 (5H, m), 7.41 (1H, t, J=8.0 Hz), 7.58 (1H, d, J=7.6 Hz).

Example 31
[[2-(3-Phenyl-2-propenyl)sulfonyl-4,5-dihydronaphtho[1,2-d]thiazol-6-yl]oxy]acetic Acid Using ethyl[(2-mercapto-4,5-dihydronaphtho[1,2-d]thiazol-6-yl)oxy]acetate and 3-bromo-1-phenyl-1-propene, the procedure of Example 29 was otherwise repeated to synthesize the title compound. Yield 43%.

m.p. 210–214° C. (ethanol)

$^1$H-NMR (DMSO-d$_6$) δ: 2.95–3.50 (5H, m), 4.53 (2H, d, J=7.6 Hz), 4.74 (2H, s), 6.10–6.33 (1H, m), 6.69 (1H, d, J=16.0 Hz), 6.92 (1H d, J=8.0 Hz), 7.15–7.60 (7H, m).

Example 32
[[2-(3,3-Diphenylpropyl)sulfonyl-4,5-dihydronaphtho[1,2-d]thiazol-6-yl]oxy]acetic Acid Using ethyl[(2-mercapto-4,5-dihydronaphtho[1,2-d]thiazol-6-yl)oxy]acetate and 3,3-diphenylpropyl iodide, the procedure of Example 29 was otherwise repeated to synthesize the title compound. Yield 22%.

m.p. 175–176° C. (ethanol)

$^1$H-NMR (CDCl$_3$) δ: 2.52–3.30 (7H, m), 3.35–3.50 (2H, m), 4.03 (1H, t, J=8.0 Hz), 4.74 (2H, s), 6.79 (1H, d, J=8.4 Hz), 7.10–7.34 (11H, m), 7.65 (1H, d, J=7.4 Hz).

Example 33
[[2-(4,4-Diphenylbutyl)sulfonyl-4,5-dihydronaphtho[1,2-d]thiazol-6-yl]oxy]acetic Acid Using ethyl[(2-mercapto-4,5-dihydronaphtho[1,2-d]thiazol-6-yl)oxy]acetate and 4,4-diphenylbutyl iodide, the procedure of Example 29 was otherwise repeated to synthesize the title compound. Yield 35%.

m.p. 180–181° C. (ethyl acetate-hexane)

$^1$H-NMR (CDCl$_3$) δ: 1.73–1.92 (2H, m), 2.10–2.25 (2H, m), 3.04–3.25 (4H, m), 3.38–3.52 (2H, m), 3.87 (1H, t, J=8.0 Hz), 3.90–4.06 (1H, br), 4.76 (2H, s), 6.79 (1H, d, J=8.0 Hz), 7.06–7.34 (11H, m), 7.64 (1H, d, J=7.4 Hz).

Example 34
[[2-(3,3-Diphenylpropyl)sulfonyl-4,5-dihydronaphtho[1,2-d]thiazol-7-yl]oxy]acetic Acid Using ethyl[(2-mercapto-4,5-dihydronaphtho[1,2-d]thiazol-7-yl)oxy]acetate and 3,3-diphenylpropyl iodide, the procedure of Example 29 was otherwise repeated to synthesize the title compound. Yield 27%.

m.p. 175–177° C. (ethyl acetate-hexane)

$^1$H-NMR (CDCl$_3$) δ: 2.50–2.71 (2H, m), 3.00–3.21 (4H, m), 3.33–3.50 (2H, m), 4.02 (1H, t, J=7.8 Hz), 4.74 (2H, s), 5.20–6.50 (1H, br), 6.80–6.92 (2H, m), 7.12–7.34 (10H, m), 7.82–7.91 (1H, m).

Example 35
[[2-(3,3-Diphenylpropyl)sulfonyl-4H-[1]benzopyrano[4,3-d]thiazol-6-yl)oxy]acetic Acid Using ethyl[(2-mercapto-4H-[1]benzopyrano[4,3-d]thiazol-6-yl)oxy]acetate and 3,3-diphenylpropyl iodide, the procedure of Example 29 was otherwise repeated to synthesize the title compound. Yield 37%. Amorphous solid.

$^1$H-NMR (CDCl$_3$) δ: 2.53–2.65 (2H, m), 3.39–3.47 (2H, m), 4.03 (1H, t, J=8.0 Hz), 4.74 (2H, s), 5.56 (2H, s), 5.30–6.00 (1H, br), 6.88–6.92 (1H, m), 7.02 (1H, t, J=8.2 Hz), 7.15–7.31 (10H, m), 7.51–7.56 (1H, m).

Example 36
[[(2-(3,3-Diphenylpropyl)sulfonyl-8H-indeno[1,2-d]thiazol-7-yl]oxy]acetic Acid To a solution of ethyl[(2-mercapto-4,5-dihydronaphtho[1,2-d]thiazol-6-yl)oxy]acetate (4.00 g, 12.4 mmol) in N,N-dimethylformamide (30 mL) was added 3,3-diphenylpropyl methanesulfonate (3.96 g, 13.6 mmol) followed by addition of potassium carbonate (1.90 g, 13.6 mmol), and the mixture was stirred at 60° C. for 2 hours. This reaction mixture was diluted with water and extracted with ethyl acetate. The organic layer was washed with water and saturated aqueous sodium chloride solution, dried over MgSO$_4$, and filtered. The filtrate was concentrated under reduced pressure to provide 3.81 g of ethyl[(2-(3,3-diphenylpropyl)thio-8H-indeno[1,2-d]thiazol-7-yl)oxy]acetate. To a solution of this compound (1.10 g, 2.19 mmol) in ethanol (30 mL)-water (3 mL) was added sodium periodate (4.68 g, 21.9 mmol) and the mixture was refluxed for 14 hours. This reaction mixture was diluted with ethyl acetate and water and, after phase separation, the aqueous layer was extracted with ethyl acetate. The organic layers were pooled, washed with water, dried over MgSO$_4$, and filtered. The filtrate was concentrated under reduced pressure and the residue was dissolved in acetic acid (10 mL). To this solution was added concentrated sulfuric acid (5 mL) and the mixture was refluxed for 1 hour. After cooling, the reaction mixture was diluted with water and extracted with 2 portions of ethyl acetate, and the combined extract was washed with water, dried over MgSO$_4$, and filtered. The filtrate was concentrated under reduced pressure and the residue was crystallized from hexane-ethyl acetate to provide 350 mg of the title compound. Yield 17%.

m.p. 131–133° C.

$^1$H-NMR (CDCl$_3$) δ: 2.52–2.66 (2H, m), 3.37–3.46 (2H, m), 3.60–4.20 (4H, m), 4.83 (2H, s), 6.80 (1H, d, J=8.0 Hz), 7.10–7.32 (10H, m), 7.36–7.46 (1H, m), 7.50 (1H, t, J=7.2 Hz).

Example 37
[[2-(4,4-Diphenylbutyl)sulfonyl-8H-indeno[1,2-d]thiazol-7-yl]oxy]acetic Acid Using ethyl[(2-mercapto-8H-indeno[1,2-d]thiazol-7-yl)oxy]acetate and 4,4-diphenylbutyl iodide, the procedure of Example 36 was otherwise repeated to synthesize the title compound. Yield 37%.

m.p. 97–101° C. (ethyl acetate-hexane)

$^1$H-NMR (CDCl$_3$) δ: 1.70–1.90 (2H$_1$, m), 2.08–2.27 (2H, m), 3.37–3.56 (2H, m), 3.85 (1H, t, J=8.0 Hz), 3.93 (2H, s), 4.82 (2H, s), 6.75–7.31 (12H, m), 7.39 (1H, t, J=8.0 Hz), 7.53 (1H, d, J=7.4 Hz).

Example 38
3-[[2-(3,3-Diphenylpropyl)sulfonyl-8H-indeno[1,2-d]thiazol-7-yl]oxy]propionic Acid Using ethyl 3-[(2-mercapto-8H-indeno(1,2-d]thiazol-7-yl)oxy]propionate and 3,3-diphenylpropyl iodide, the procedure of Example 36 was otherwise repeated to synthesize the title compound. Yield 10%.

m.p. 215–218° C. (ethyl acetate)

$^1$H-NMR (DMSO-d$_6$) δ: 2.40–2.58 (2H, m), 2.70–2.81 (2H, m), 3.30–3.50 (2H, m), 3.95 (2H, s), 4.00–4.18 (1H, m), 4.30–4.42 (2H, m), 7.02–7.50 (14H, m.

Example 39
[[2-(3,3-Diphenylpropyl)sulfonyl-8H-indeno[1,2-d]thiazol-6-yl]oxy]acetic Acid Using ethyl[(2-mercapto-8H-indeno[1,2-d]thiazol-6-yl)oxy]acetate and 3,3-diphenylpropyl iodide, the procedure of Example 36 was otherwise repeated to synthesize the title compound. Yield 10%.

m.p. 172–174° C. (ethyl acetate)

$^1$H-NMR (CDCl$_3$) δ: 2.45–2.70 (2H, m), 3.30–3.48 (2H, m), 3.6–4.4 (4H, m), 4.76 (2H, s), 6.94–7.32 (12H, m), 7.76 (1H, d, J=8.4 Hz).

Example 40

[[2-(3,3-Diphenylpropyl)oxy-4,5-dihydronaphtho[1,2-d]thiazol-6-yl]oxy]acetic Acid A mixture of ethyl[(2-hydroxy-4,5-dihydronaphtho[1,2-d]thiazol-6-yl)oxy]acetate (1.40 g, 4.58 mmol), sodium hydride (60% dispersion in liquid paraffin, 200 mg, 5.00 mmol), 3,3-diphenylpropyl iodide (1.60 g, 5.04 mmol), and N,N-dimethylformamide (30 ml) was stirred at 70° C. for 2 hours. This reaction mixture was poured into water (50 mL) and extracted with 2 portions of ethyl acetate. The pooled organic solution was washed with water, dried over MgSO$_4$, and filtered and the filtrate was concentrated under reduced pressure. The residue was purified by silica gel column chromatography (hexane-ethyl acetate=8:1) to provide 810 mg of ethyl[[2-(3,3-diphenylpropyl)oxy-4,5-dihydronaphtho[1,2-d]thiazol-6-yl]oxy]acetate. To a solution of this compound (700 mg, 1.40 mmol) in a mixture of tetrahydrofuran (8 mL) and methanol (2 mL) was added 1N-aqueous sodium hydroxide solution (1.4 mL) dropwise and the mixture was stirred at room temperature for 5 minutes. To this reaction mixture was added 1N-hydrochloric acid, and the mixture was extracted with ethyl acetate. The organic layer was washed with water and saturated aqueous sodium chloride solution, dried over MgSO$_4$, and filtered. The filtrate was concentrated under reduced pressure and the residue was recrystallized from ethyl acetate-hexane to provide 500 mg of the title compound. Yield 24%.

m.p. 165–166° C.

$^1$H-NMR (CDCl$_3$) δ: 2.5–2.64 (2H, m), 2.79–2.90 (2H, m), 3.04–3.16 (4H, m), 4.15–4.26 (1H, m), 4.38 (1H, t, J=6.6 Hz), 4.70 (2H, s), 5.20–6.40 (1H, br), 6.67 (1H, d, J=7.8 Hz), 7.12–7.36 (11H, m), 7.42 (1H, d, J=7.6 Hz).

Example 41

[[2-(3,3-Diphenylpropyl)amino-4,5-dihydronaphtho[1,2-d]thiazol-6-yl]oxy]acetic Acid To a mixture of ethyl[(6-bromo-5,6,7,8-tetrahydro-5-oxo-1-naphthalenyl)oxy]acetate (1.20 g, 3.67 mmol), N-(3,3-diphenylpropyl)thiourea (1.10 g, 4.04 mmol), and acetonitrile (30 mL) was added triethylamine (0.56 mL, 4.04 mmol), and the mixture was refluxed for 2 hours. After cooling, the reaction mixture was diluted with water and extracted with ethyl acetate. The organic layer was washed with 1N-hydrochloric acid, saturated aqueous sodium chloride solution, and water, dried over MgSO$_4$, and filtered. The filtrate was concentrated under reduced pressure and the residue was purified by silica gel column chromatography (hexane-ethyl acetate=5:1) to provide 700 mg of ethyl[[2-(3,3-diphenylpropyl)amino-4,5-dihydronaphtho[1,2-d]thiazol-6-yl]oxy]acetate. To a solution of this compound in acetic acid (10 mL) was added concentrated hydrochloric acid (5 mL) and the mixture was refluxed for 1 hour. After cooling, the reaction mixture was diluted with water and extracted with 2 portions of ethyl acetate. The pooled organic layer was washed with water, dried over MgSO$_4$, and filtered and the filtrate was concentrated under reduced pressure. The residue was crystallized from hexane-ethyl acetate to provide 500 mg of the title compound. Yield 17%.

m.p. 240–243° C.

$^1$H-NMR (DMSO-d$_6$) δ: 2.26–2.50 (2H, m), 2.66–2.85 (2H, m), 2.90–3.08 (2H, m), 3.10–3.30 (2H, m), 4.05–4.17 (1H, m), 4.67 (2H, s), 6.72 (1H, d, J=8.0 Hz), 7.08–7.44 (13H, m), 7.55–7.67 (1H, m).

Example 42

[(2-Diphenylmethylamino-4,5-dihydronaphtho[1,2-d]thiazol-6-yl]oxy]acetic Acid

To a mixture of ethyl[(6-bromo-5,6,7,8-tetrahydro-5-oxo-1-naphthalenyl)oxy]acetate (1.10 g, 3.36 mmol), N-(diphenylmethyl)thiourea (900 mg, 3.70 mmol), and ethanol (15 mL) was added triethylamine (0.51 mL, 3.70 mmol), and the mixture was refluxed for 6 hours. After cooling, the reaction mixture was diluted with water and extracted with ethyl acetate. The organic layer was washed with 1N-hydrochloric acid, saturated aqueous sodium chloride solution, and water, dried over MgSO$_4$, and filtered. The filtrate was concentrated under reduced pressure. To a solution of this concentration residue (0.79 g, 1.70 mmol) in tetrahydrofuran (16 mL)-methanol (4 mL) was added 1N-aqueous sodium hydroxide solution (2.0 mL) dropwise and the mixture was stirred at room temperature for 10 minutes. The solvent was then distilled off under reduced pressure and the residue was recrystallized from acetic acid-water to provide 0.49 g of the title compound. Yield 33%.

m.p. 250–252° C.

$^1$H-NMR (DMSO-d$_6$) δ: 2.62–2.82 (2H, m), 2.85–3.01 (2H, m), 4.66 (2H, s), 6.10 (1H, d, J=8.4 Hz), 6.72 (1H, d, J=8.0 Hz), 7.11–7.45 (13H, m), 8.48 (1H, d, J=8.4 Hz).

Example 43

[[2-(2,2-Diphenylethyl)amino-4,5-dihydronaphtho[1,2-d]thiazol-6-yl]oxy]acetic Acid Hydrochloride To a mixture of ethyl[(6-bromo-5,6,7,8-tetrahydro-5-oxo-1-naphthalenyl)oxy]acetate (1.20 g, 3.67 mmol), N-(2,2-diphenylethyl)thiourea (1.00 g, 4.03 mmol), and ethanol (20 mL) was added triethylamine (0.56 mL, 4.04 mmol), and the mixture was refluxed for 4 hours. After cooling, the reaction mixture was diluted with water and extracted with ethyl acetate. The organic layer was washed with 1N-hydrochloric acid, saturated aqueous sodium chloride solution, and water, dried over MgSO$_4$, and filtered. The filtrate was concentrated under reduced pressure and the residue was purified by silica gel column chromatography (hexane-ethyl acetate=5:1) to provide 1.10 g of ethyl[[2-(3,3-diphenylpropyl)amino-4,5-dihydronaphtho[1,2-d]thiazol-6-yl]oxy]acetate. To a solution of this compound in acetic acid (20 mL) was added concentrated hydrochloric acid (10 mL), and the mixture was refluxed for 1 hour. After cooling, the reaction mixture was treated with water for crystallization to provide 1.00 g of the title compound. Yield 61%.

m.p. 136–140° C. (acetic acid-water)

$^1$H-NMR (DMSO-d$_6$) δ: 2.70–2.81 (2H, m), 2.96–3.10 (2H, m), 4.10–4.28 (2H, m), 4.40–4.50 (1H, m), 4.72 (2H, s), 5.0–5.8 (2H, br), 6.88 (1H, d, J=8.2 Hz), 7.15–7.52 (12H, m), 9.0–9.7 (1H, br).

Example 44

[[2-(2,2-Diphenylethyl)amino-8H-indeno[1,2-d]thiazol-7-yl]oxy]acetic Acid Hydrochloride Using ethyl[(2-bromo-2,3-dihydro-1-oxo-1H-inden-4-yl)oxy]acetate and N-(2,2-diphenylethyl)thiourea, the procedure of Example 43 was otherwise repeated to synthesize the title compound. Yield 21%.

m.p. 206–210° C. (decomp.) (acetic acid-water)

$^1$H-NMR (DMSO-d$_6$) δ: 2.75–3.00 (6H, m), 4.27 (2H, t, J=6.2 Hz), 6.05 (1H, t, J=8.0 Hz), 6.80 (1H, d, J=8.4 Hz), 7.16–7.57 (13H, m).

Example 45

[[2-(3,3-Diphenylpropyl)amino-8H-indeno[1,2-d]thiazol-7-yl]oxy]acetic Acid Hydrochloride Using ethyl[(2-bromo-2,3-dihydro-1-oxo-1H-inden-4-yl)oxy]acetate and N-(3,3-diphenylpropyl)thiourea, the procedure of Example 43 was otherwise repeated to synthesize the title compound. Yield 53%.

m.p. 242–245° C. (decomp.) (ethyl acetate)

$^1$H-NMR (DMSO-d$_6$) δ: 2.33–2.58 (2H, m), 3.28–3.42 (2H, m), 3.69 (2H, s), 4.20 (1H, t, J=8.0 Hz), 4.79 (2H, s), 5.00–5.80 (2H, br), 6.82 (1H, d, J=8.0 Hz), 7.10–7.43 (12H, m), 9.50–10.0 (1H, br).

Example 46
[(2-(1,2-Diphenylethyl)thio-4,5-dihydronaphtho[1,2-d]thiazol-6-yl)oxy]acetic Acid Using ethyl[(2-mercapto-4,5-dihydronaphtho[1,2-d]thiazol-6-yl)oxy]acetate and 1-bromo-1,2-diphenylethane, the procedure of Example 1 was otherwise repeated to synthesize the title compound. Yield 41%.

m.p. 201–204° C. (ethyl acetate)

$^1$H-NMR (DMSO-d$_6$) δ: 2.75–3.11 (4H, m), 3.24–3.52 (2H, m), 4.71 (2H, s), 5.04 (1H, dd, J=6.8, 8.6 Hz), 6.84 (1H, d, J=8.4 Hz), 7.07–7.51 (12H, m), 1H not confirmed.

Example 47
[(2-Phenylamino-4,5-dihydronaphtho[1,2-d]thiazol-6-yl)oxy]acetic Acid Hydrochloride Using ethyl[(6-bromo-5,6,7,8-tetrahydro-5-oxo-1-naphthalenyl)oxy]acetate and 1-phenyl-2-thiourea, the procedure of Example 43 was otherwise repeated to synthesize the title compound. Yield 47%.

m.p. 289–292° C. (decomp.) (acetic acid-water)

$^1$H-NMR (DMSO-d$_6$) δ: 2.81–3.13 (4H, m), 4.71 (2H, s), 6.00–8.00 (1H, br), 6.80 (1H, d, J=7.8 Hz), 6.96 (1H, t, J=8.4 Hz), 7.17–7.43 (4H, m), 7.72 (2H, d, J=7.8 Hz), 10.28 (1H, br s).

Example 48
Ethyl[(2-diphenylmethylthio-4,5-dihydronaphtho[1,2-d]thiazol-6-yl)oxy]acetate To a solution of ethyl[(2-mercapto-4,5-dihydronaphtho[1,2-d]thiazol-6-yl)oxy]acetate (4.00 g, 12.4 mmol) in N,N-dimethylformamide (30 mL) were serially added bromodiphenylmethane (3.38 g, 13.7 mmol) and potassium carbonate (1.90 g, 13.7 mmol), and the mixture was stirred at 60° C. for 2 hours. This reaction mixture was diluted with water and extracted with ethyl acetate. The organic layer was washed with water and saturated aqueous sodium chloride solution, dried over MgSO$_4$, filtered, and concentrated under reduced pressure. The residue was recrystallized from ethyl acetate to provide 4.50 g of the title compound Yield 74%.

m.p. 124–126° C.

$^1$H-NMR (CDCl$_3$) δ: 1.30 (3H, t, J=7.0 Hz), 2.81–2.93 (2H, m), 3.03–3.14 (2H, m), 4.27 (2H, q, J=7.0 Hz), 4.64 (2H, s), 6.06 (1H, s), 6.67 (1H, d, J=7.6 Hz), 7.15–7.51 (11H, m), 7.58 (1H, d, J=7.4 Hz).

Example 49
Ethyl[(2-(2,2-diphenylethyl)thio-4,5-dihydronaphtho[1,2-d]thiazol-6-yl)oxy]acetate Using ethyl[(2-mercapto-4,5-dihydronaphtho[1,2-d]thiazol-6-yl)oxy]acetate and 2,2-diphenylethyl iodide, the procedure of Example 48 was otherwise repeated to synthesize the title compound. Yield 68%.

m.p. 92–93° C. (ethanol)

$^1$H-NMR (CDCl$_3$) δ: 1.31 (3H, t, J=7.0 Hz), 2.91–3.00 (2H, m), 3.10–3.21 (2H, m), 3.94 (2H, d, J=7.8 Hz), 4.29 (2H, q, J=7.0 Hz), 4.51 (1H, t, J=7.8 Hz), 4.67 (2H, s), 6.70 (1H, d, J=8.2 Hz), 7.18–7.41 (11H, m), 7.64 (1H, d, J=6.8 Hz).

Example 50
Ethyl[(2-diphenylmethylsulfonyl-4,5-dihydronaphtho[1,2-d]thiazol-6-yl)oxy]acetate To a solution of ethyl[(2-diphenylmethylthio-4,5-dihydronaphtho[1,2-d]thiazol-6-yl)oxy]acetate (1.50 g, 3.08 mmol) in chloroform (30 mL) was added m-chloroperbenzoic acid (55%, 1.70 g, 6.77 mmol) at 0° C. and the mixture was stirred at room temperature for 2 hours. This reaction mixture was washed with saturated aqueous sodium hydrogen carbonate solution and water, dried over MgSO$_4$, filtered, and concentrated under reduced pressure. The residue was crystallized from ethyl acetate-hexane to provide 1.25 g of the title compound. Yield 78%.

m.p. 184–187° C.

$^1$H-NMR (CDCl$_3$) δ: 1.31 (3H, t, J=7.0 Hz), 2.91–3.18 (4H, m), 4.28 (2H, q, J=7.0 Hz), 4.67 (2H, s), 5.94 (1H, s), 6.76 (1H, d, J=8.0 Hz), 7.25–7.41 (7H, m), 7.52–7.74 (5H, m).

Example 51
[(2-Diphenylmethylsulfonyl-4,5-dihydronaphtho[1,2-d]thiazol-6-yl)oxy]acetic Acid To a solution of ethyl[(2-mercapto-4,5-dihydronaphtho[1,2-d]thiazol-6-yl)oxy]acetate (4.00 g, 12.4 mmol) in N,N-dimethylformamide (30 mL) were serially added bromodiphenylmethane (3.38 g, 13.7 mmol) and potassium carbonate (1.90 g, 13.7 mmol) and the mixture was stirred at 60° C. for 2 hours. This reaction mixture was diluted with water and extracted with ethyl acetate. The organic layer pas washed with water and saturated aqueous sodium chloride solution, dried over MgSO$_4$, filtered, and concentrated under reduced pressure to provide ethyl[(2-diphenylmethylthio-4,5-dihydronaphtho[1,2-d]thiazol-6-yl)oxy]acetate (2.70 g). This compound (1.40 g, 2.87 mmol) was dissolved in dichloromethane (30 mL) followed by addition of m-chloroperbenzoic acid (55%, 2.00 g, 6.32 mmol) at 0° C., and the mixture was stirred at room temperature for 2 hours. This reaction mixture was washed with saturated sodium hydrogen carbonate solution and water, dried over MgSO$_4$, filtered, and concentrated under reduced pressure to provide ethyl[(2-diphenylmethylsulfonyl-4,5-dihydronaphtho[1,2-d]thiazol-6-yl)oxy]acetate (1.10 g). To a solution of this compound (1.10 g, 2.12 mmol) in tetrahydrofuran (10 mL)-methanol (5 mL) was added 1N-aqueous sodium hydroxide (3.0 mL) dropwise and the mixture was stirred at room temperature for 15 minutes. To this reaction mixture was added 1N-hydrochloric acid followed by extraction with ethyl acetate. The organic layer was washed with water and saturated aqueous sodium chloride solution, dried over MgSO$_4$, filtered, and concentrated under reduced pressure. The residue was crystallized from ethyl acetate to provide 550 mg of the title compound. Yield 39%.

m.p. 219–221° C.

$^1$H-NMR (DMSO-d$_6$) δ: 2.90–3.18 (4H, m), 4.74 (2H, s), 6.33 (1H, s), 6.92 (1H, d, J=8.4 Hz), 7.21–7.75 (12H, m), 1H not confirmed.

Example 52
[(2-Benzyl-4,5-dihydronaphtho[1,2-d]thiazol-6-yl)oxy]acetic Acid

A solution of ethyl[(6-bromo-5,6,7,8-tetrahydro-5-oxo-1-naphthalenyl)oxy]acetate (2.16 g, 6.61 mmol) and phenylthioacetamide (1.00 g, 6.61 mmol) in a mixture of ethanol (25 mL) and N,N-dimethylformamide (5 mL) was stirred at 60° C. for 14 hours and, then, refluxed for 2 hours. After cooling, the reaction mixture was diluted with water and extracted with ethyl acetate. The organic layer was washed with water and saturated aqueous sodium chloride solution, dried over MgSO$_4$, filtered, and concentrated under reduced pressure. The residue was subjected to silica gel column chromatography (hexane-ethyl acetate=1:5) to provide ethyl[(2-benzyl-4,5-dihydronaphtho[1,2-d]thiazol-6-yl)oxy]acetate (540 mg). To a solution of this compound (0.54 g, 1.42 mmol) in a mixture of tetrahydrofuran (16 mL) and methanol (4 mL) was added 1N-hydrochloric acid followed by extraction with ethyl acetate. The organic layer was washed with water and saturated aqueous sodium chloride solution, dried over MgSO$_4$, filtered, and concentrated under reduced pressure. The residue was recrystallized from ethyl acetate-hexane to provide 320 mg of the title compound. Yield 14%.

m.p. 146–149° C.

$^1$H-NMR (CDCl$_3$) δ: 2.84–2.96 (2H, m), 3.05–3.17 (2H, m), 4.36 (2H, s), 4.71 (2H, s), 6.71 (1H, d, J=7.6 Hz), 6.90–7.42 (7H, m), 7.61 (1H, d, J=7.4 Hz).

Example 53

[(2-Diphenylmethyl-4,5-dihydronaphtho[1,2-d]thiazol-6-yl)oxy]acetic Acid

Using ethyl[(6-bromo-5,6,7,8-tetrahydro-5-oxo-1-naphthalenyl)oxy]acetate and diphenylthioacetamide, the procedure of Example 52 was otherwise repeated to synthesize the title compound. Yield 31%. Amorphous solid.

$^1$H-NMR (CDCl$_3$) δ: 2.87–3.18 (4H, m), 4.66 (2H, s), 5.93 (1H, s), 6.68 (1H, d, J=7.4 Hz), 7.10–7.45 (12H, m), 7.59 (1H, d, J=7.2 Hz).

Example 54

[(2-Phenyl-4,5-dihydronaphtho[1,2-d]thiazol-6-yl)oxy]acetic Acid

Using ethyl[(6-bromo-5,6,7,8-tetrahydro-5-oxo-1-naphthalenyl)oxy]acetate and thiobenzamide, the procedure of Example 52 was otherwise repeated to synthesize the title compound. Yield 27%. Amorphous solid.

$^1$H-NMR (DMSO-d$_6$) δ: 3.09 (4H, s), 4.73 (2H, s), 6.85 (1H, d, J=8.2 Hz), 7.26 (1H, t, J=8.2 Hz), 7.46–7.62 (4H, m), 7.92–8.00 (2H, m), 1H not confirmed.

Example 55

[(2-(2,2-Diphenylethyl)-4,5-dihydronaphtho[1,2-d]thiazol-6-yl)oxy]acetic Acid

Using ethyl[(6-bromo-5,6,7,8-tetrahydro-5-oxo-1-naphthalenyl)oxy]acetate and 3,3-diphenylthiopropionamide, the procedure of Example 52 was otherwise repeated to synthesize the title compound. Yield 19%. Amorphous solid.

$^1$H-NMR (DMSO-d$_6$) δ: 2.78–3.11 (4H, m), 3.80 (2H, d, J=7.8 Hz), 4.56 (1H, t, J=7.8 Hz), 4.69 (2H, s), 6.79 (1H, d, J=7.6 Hz), 6.98–7.56 (12H, m), 12.6–13.5 (1H, br).

Example 56

[(2-(2,4-Dinitrophenyl)thio-4,5-dihydronaphtho[1,2-d]thiazol-6-yl)oxy]acetic Acid To a solution of ethyl[(2-mercapto-4,5-dihydronaphtho[1,2-d]thiazol-6-yl)oxy]acetate (1.30 g, 4.04 mmol) in N,N-dimethylformamide (20 mL) was added sodium hydride (60% dispersion in liquid paraffin, 178 mg, 4.45 mmol) at 0° C., and the mixture was stirred at room temperature for 10 minutes. To this mixture was added 1-chloro-2,4-dinitrobenzene (900 mg, 4.45 mmol) and the mixture was stirred at room temperature for 30 minutes. This reaction mixture was poured into water (30 mL) and extracted with 2 portions of ethyl acetate. The pooled organic layer was washed with water, dried over MgSO$_4$, filtered, and concentrated under reduced pressure to provide ethyl[(2-(2,4-dinitrophenyl)thio,-4,5-dihydronaphtho[1,2-d]thiazol-6-yl)oxy]acetate (1.17 g). To a solution of this compound (1.17 g, 2.40 mmol) in a mixture of tetrahydrofuran (16 mL) and methanol (4 mL) was added 1N-aqueous sodium hydroxide (3.0 mL) dropwise and the mixture was stirred at room temperature for 20 minutes. After the solvent was distilled off under reduced pressure, 1N-hydrochloric acid was added to the residue and the mixture was extracted with ethyl acetate. The organic layer was washed with water and saturated aqueous sodium chloride solution, dried over MgSO$_{41}$, filtered, and concentrated under reduced pressure. The residue was recrystallized from ethyl acetate to provide 0.91 g of the title compound. Yield 49%.

m.p. 223–226° C.

$^1$H-NMR (DMSO-d$_6$) δ: 3.02–3.30 (4H, m), 4.75 (2H, s), 6.91 (1H, d, J=8.4 Hz), 7.26 (1H, t, J=8.2 Hz), 7.39(1H, d, J=9.0 Hz), 7.51 (1H, d, J=7.6 Hz), 8.43 (1H, dd, J=9.0, 2.4 Hz), 8.96 (1H, d, J=2.4 Hz), 1H not confirmed.

Example 57

[(2-Diphenylmethylthio-4,5-dihydronaphtho[1,2-d]thiazol-8-yl)oxy]acetic Acid

Using ethyl[(2-mercapto-4,5-dihydronaphtho[1,2-d]thiazol-8-yl)oxy]acetate and bromodiphenylmethane, the procedure of Example 1 was otherwise repeated to synthesize the title compound. Yield 90%.

m.p. 141–143° C. (ethyl acetate-hexane)

$^1$H-NMR (CDCl$_3$) δ: 2.72–3.03 (4H, m), 4.40–4.89 (3H, m), 6.02 (1H, s), 6.80 (1H, dd, J=8.2, 2.6 Hz), 7.09 (1H, d, J=8.6 Hz), 7.19–7.57 (11H, m).

Example 58

[(2-(2,2-Diphenylethyl)thio-4,5-dihydronaphtho[1,2-d]thiazol-8-yl)oxy]acetic Acid Using ethyl[(2-mercapto-4,5-dihydronaphtho[1,2-d]thiazol-8-yl)oxy]acetate and 2,2-diphenylethyl iodide, the procedure of Example 21 was otherwise repeated to synthesize the title compound. Yield 69%.

m.p. 165–167° C. (ethyl acetate)

$^1$H-NMR (DMSO-d$_6$) δ: 2.95 (4H, s), 3.99 (2H, d, J=7.6 Hz), 4.50 (1H, t, J=8.0 Hz), 4.68 (2H, s), 6.78 (1H, dd, J=8.2, 2.8 Hz), 7.15–7.45 (12H, m), 1H not confirmed.

Example 59

[(2-Diphenylmethylsulfonyl-4,5-dihydronaphtho[1,2-d]thiazol-8-yl)oxy]acetic Acid Using ethyl[(2-mercapto-4,5-dihydronaphtho[1,2-d]thiazol-8-yl)oxy]acetate and bromodiphenylmethane, the procedure of Example 51 was otherwise repeated to synthesize the title compound. Yield 35%.

m.p. 169–170° C. (ethyl acetate)

$^1$H-NMR (CDCl$_3$) δ: 2.81–3.08 (4H, m), 4.80 (2H, s.), 5.98 (1H, s), 6.00–6.45 (1H, br), 6.88 (1H, dd, J=8.4, 2.6 Hz), 7.15 (1H, d, J=8.4 Hz), 7.20–7.72 (11H, m).

Example 60

[(2-(2,2-Diphenylethyl)sulfonyl-4,5-dihydronaphtho[1,2-d]thiazol-8-yl)oxy]acetic Acid Using ethyl[(2-mercapto-4,5-dihydronaphtho[1,2-d]thiazol-8-yl)oxy]acetate and 2,2-diphenylethyl iodide, the procedure of Example 51 was otherwise repeated to synthesize the title compound. Yield 39%.

m.p. 183–185° C. (ethyl acetate)

$^1$H-NMR (CDCl$_3$) δ: 2.82–3.10 (4H, s), 4.31 (2H, d, J=7.4 Hz), 4.72 (1H, t, J=7.4 Hz), 4.77 (2H, s), 6.87 (1H, dd, J=8.4, 2.4 Hz), 6.99–7.21 (11H, m), 7.47 (1H, d, J=2.4 Hz), 7.30–8.40 (1H, br).

Example 61
Ethyl[(2-(2,2-diphenylethylsulfinyl)-4,5-dihydronaphtho[1,2-d]thiazol-6-yl)oxy]acetate To a solution of ethyl[(2-mercapto-4,5-dihydronaphtho[1,2-d]thiazol-6-yl)oxy]acetate (1.05 g, 3.27 mmol) in N,N-dimethylformamide (15 mL) were serially added 2,2-diphenylethyl iodide (1.11 g, 3.60 mmol) and potassium carbonate (500 mg, 3.60 mmol) and the mixture was stirred at 60° C. for 2 hours. This reaction mixture was diluted with water and extracted with ethyl acetate. The organic layer was washed with water and saturated aqueous sodium chloride solution, dried over $MgSO_4$, filtered, and concentrated under reduced pressure to provide ethyl[[2-(2,2-diphenylethyl)thio-4,5-dihydronaphtho[1,2-d]thiazol-6-yl]oxy]acetate (1.11 g). To a solution of this compound (1.00 g, 1.99 mmol) in ethanol (45 mL)-water (5 mL) was added sodium periodate (0.51 g, 2.39 mmol) and the mixture was refluxed for 3 hours. To this reaction mixture were added-ethyl acetate and water, and the resulting two layers were separated. The aqueous layer was extracted with ethyl acetate and the pooled organic layer was washed with water, dried over $MgSO_4$, filtered, and concentrated under reduced pressure. The residue was purified by silica gel column chromatography (hexane-ethyl acetate=1:8) and recrystallized from ethyl acetate to provide 0.64 g of the title compound. Yield 42%.

m.p. 127–129° C.

$^1$H-NMR (CDCl$_3$) δ: 1.31 (3H, t, J=7.0 Hz), 2.97–3.24 (4H, m), 3.72–3.98 (2H, m), 4.28 (2H, q, J=7.0 Hz), 4.67 (2H, s), 4.77 (1H, dd, J=9.6, 6.6 Hz), 6.73 (1H, d, J=8.4 Hz), 7.08–7.42 (11H, m), 7.59 (1H, d, J=7.6 Hz).

Example 62
[($^2$-(2,2-Diphenylethylsulfinyl)-4,5-dihydronaphtho[1,2-d]thiazol-6-yl)oxy]acetic Acid To a solution of ethyl[(2-(2,2-diphenylethylsulfinyl)-4,5-dihydronaphtho[1,2-d]thiazol-6-yl)oxy]acetate (0.50 g, 0.965 mmol) in a mixture of tetrahydrofuran (16 mL) and methanol (4 mL) was added 1N-aqueous sodium hydroxide (2 mL) dropwise, and the mixture was stirred at room temperature for 20 minutes. After the solvent was distilled off under reduced pressure, 1N-hydrochloric acid was added to the residue and the mixture was extracted with ethyl acetate. The organic layer was washed with water and saturated aqueous sodium chloride solution, dried over $MgSO_4$, filtered, and concentrated under reduced pressure to provide 0.36 g of the title compound as amorphous solid. Yield 76%.

$^1$H-NMR (CDCl$_3$) δ: 2.95–3.23 (4H, m), 3.78–4.00 (2H, m), 4.1–4.9 (4H, m), 6.76 (1H, d, J=8.6 Hz), 7.10–7.42 (11H, m), 7.60 (1H, d, J=7.4 Hz).

Example 63
[(2-(2-Naphthyl)(phenyl)methylthio-4H-[1]benzopyrano[4,3-d]thiazol-6-yl)oxy]acetic Acid To a suspension of ethyl[(2-mercapto-4-[1]benzopyrano[4,3-d]thiazol-6-yl)oxy]acetate (1.00 g, 3.09 mmol) in acetonitrile (10 mL) were serially added a solution of (2-naphthyl)phenylmethyl bromide (1.13 g, 4.02 mmol) in N,N-dimethylformamide (5 mL) and a solution of triethylamine (344 mg, 3.40 mmol) in acetonitrile (5 mL) dropwise, and the mixture was stirred at room temperature for 1 hour. After the solvent was distilled off, the residue was diluted with water and extracted with ethyl acetate. The organic layer was washed with water, dried over MgSO4, filtered, and concentrated under reduced pressure. The residue was purified by silica gel column chromatography (hexane-ethyl acetate=4:1) and the resulting solid was recrystallized from hexane-ethyl acetate to provide ethyl[(2-(2-naphthylphenyl)(phenyl)methylthio-4H-[1]benzopyrano[4,3-d]thiazol-6-yl)oxy]acetate (779 mg). To a solution of this compound (400 mg, 0.74 mmol) in a mixture of tetrahydrofuran (9 mL) and methanol (3 mL) was added 1N-aqueous sodium hydroxide (1 mL) dropwise and the mixture was stirred at room temperature for 1 hour. This reaction mixture was adjusted to pH 5 with 0.1N-hydrochloric acid and extracted with ethyl acetate. The organic layer was washed with water and saturated aqueous sodium chloride solution, dried over $MgSO_4$, filtered, and concentrated under reduced pressure to provide 363 mg of the title compound. Yield 96%. Amorphous solid.

$^1$H-NMR (CDCl$_3$) δ: 2.40–3.80 (1H, br), 4.69 (2H, s), 5.36 (2H, s), 6.24 (1H, s), 6.84 (1H, d, J=7.8 Hz), 6.96 (1H, t, J=7.8 Hz), 7.20–7.63 (9H, m), 7.80–7.84 (3H, m), 7.93 (1H, s).

Example 64
[(2-(4-Methylphenyl)(phenyl)methylthio-4H-[1]benzopyrano[4,3-d]thiazol-6-yl)oxy]acetic Acid Using ethyl[(2-mercapto-4H-[1]benzopyrano[4,3-d]thiazol-6-yl)oxy]acetate and (4-methylphenyl)(phenyl)methyl bromide, the procedure of Example 63 was otherwise repeated to synthesize the title compound. Yield 4%. Amorphous solid.

$^1$H-NMR (CDCl$_3$) δ: 2.32 (3H, s), 2.60–3.80 (1H, br), 4.70 (2H, s), 5.39 (2H, s), 6.03 (1H, s), 6.81– 6.86 (1H, m), 6.96 (1H, t, J=8.2 Hz), 7.12–7.53 (10H, m).

Example 65
[(2-(4-Chlorophenyl)(phenyl)methylthio-4H-[1]benzopyrano[4,3-d]thiazol-6-yl)oxy]acetic Acid Using ethyl[(2-mercapto-4H-[1]benzopyrano[4,3-d]thiazol-6-yl)oxy]acetate and (4-chlorophenyl)(phenyl)methyl bromide, the procedure of Example 63 was otherwise repeated to synthesize the title compound. Yield 49%. Amorphous solid.

$^1$H-NMR (CDCl$_3$) δ: 4.75 (2H, s), 5.40 (2H, s), 6.06 (1H, s), 6.77–6.82 (1H, m), 6.94 (1H, t, J=7:6 Hz), 7.27–7.47 (10$_H$, m), 1H not confirmed.

Example 66
[(2-(4-Methylphenyl)(phenyl)methylthio-4,5-dihydronaphtho[1,2-d]thiazol-6-yl)oxy]acetic Acid Using ethyl[(2-mercapto-4,5-dihydronaphtho[1,2-d]thiazol-6-yl)oxy]acetate and (4-methylphenyl)(phenyl)methyl bromide, the procedure of Example 63 was otherwise repeated to synthesize the title compound. Yield 98%. Amorphous solid.

$^1$H-NMR (CDCl$_3$) δ: 2.31 (3H, s), 2.82–2.91 (2H, m), 3.03–3.11 (2H, m), 4.71 (2H, s), 4.60–5.00 (1H, br), 6.01 (1H, s), 6.70 (1H, d, J=8.8 Hz), 7.11–7.61 (11H, m).

Example 67
[(2-(4-Chlorophenyl)(phenyl)methylthio-4,5-dihydronaphtho[1,2-d]thiazol-6-yl)oxy]acetic Acid Using ethyl[(2-mercapto-4,5-dihydronaphtho[1,2-d]thiazol-6-yl)oxy]acetate and (4-chlorophenyl)(phenyl)methyl bromide, the procedure of Example 63-was otherwise repeated to synthesize the title compound. Yield 78%. Amorphous solid.

$^1$H-NMR (CDCl$_3$) δ: 2.84–2.93 (2H, m), 3.06–3.14 (2H, m), 4.71 (2H, s), 6.04 (1H, s), 6.68 (1H, d, J=8.4 Hz), 7.17–7.57 (11H, m), 1H not confirmed.

Example 68

[(2-(4-Fluorophenyl)(phenyl)methylthio-4,5-dihydronaphtho[1,2-d]thiazol-6-yl)oxy]acetic Acid Using ethyl[(2-mercapto-4,5-dihydronaphtho[1,2-d]thiazol-6-yl)oxy]acetate and (4-fluorophenyl)(phenyl)methyl bromide, the procedure of Example 63 was otherwise repeated to synthesize the title compound. Yield 79%. Amorphous solid.

$^1$H-NMR (CDCl$_3$) δ: 2.84–2.93 (2H, m), 3.04–3.12 (2H, m), 3.80–4.80 (1H, br), 4.72 (2H, s), 6.05 (1H, s), 6.72 (1H, d, J=8.4 Hz), 6.96–7.04 (2H, m), 7.19–7.49 (8H, m), 7.58 (1H, d, J=6.8 Hz).

Example 69

[(2-Bis(4-fluorophenyl)methylthio-4,5-dihydronaphtho[1,2-d]thiazol-6-yl)oxy]acetic Acid Using ethyl[(2-mercapto-4,5-dihydronaphtho[1,2-d]thiazol-6-yl)oxy]acetate and bis(4-fluorophenyl)methyl bromide, the procedure of Example 63 was otherwise repeated to synthesize the title compound. Yield 77%. Amorphous solid.

$^1$H-NMR (CDCl$_3$) δ: 2.95–3.20 (4H, m), 4.76 (2H, s), 5.94 (1H, s), 6.80 (1H, d, J=7.6 Hz), 7.00–7.09 (4H, m), 7.32 (1H, t, J=7.8 Hz), 7.55–7.62 (4H, m), 7.69–7.73 (1H, m), 1H not confirmed.

Example 70

[(2-Bis(4-chlorophenyl)methylthio-4,5-dihydronaphtho[1,2-d]thiazol-6-yl)oxy]acetic Acid Using ethyl[(2-mercapto-4,5-dihydronaphtho-[1,2-d]thiazol-6-yl)oxy]acetate and bis(4-chlorophenyl)methyl bromide, the procedure of Example 63 was otherwise repeated to synthesize the title compound. Yield 77%. Amorphous solid.

$^1$H-NMR (CDCl$_3$) δ: 2.86–2.94 (2H, m), 3.07–3.14 (2H, m), 4.75 (2H, s), 6.04 (1H, s), 6.69 (1H, d, J=8.2 Hz), 7.18–7.41 (9H, m), 7.54 (1H, d, J=7.4 Hz), 1H not confirmed.

Example 71

[(2-(4-Methoxyphenyl)(phenyl)methylthio-4,5-dihydronaphtho[1,2-d]thiazol-6-yl)oxy]acetic Acid Using ethyl[(2-mercapto-4,5-dihydronaphtho[1,2-d]thiazol-6-yl)oxy]acetate and (4-methoxyphenyl)(phenyl)methyl bromide, the procedure of Example 63 was otherwise repeated to synthesize the title compound. Yield 87%. Amorphous solid.

$^1$H-NMR (CDCl$_3$) δ: 2.82–2.91 (2H, m), 3.02–3.10 (2H, m), 3.78 (3H, s), 4.20–4.80 (1H, br), 4.71 (2H, s), 6.00 (1H, s), 6.70 (1H, d, J=8.4 Hz), 6.82–6.88 (2H, m), 7.18–7.61 (9H, m).

Example 72

[(2-Phenyl)(4-trifluoromethylphenyl)methylthio-4,5-dihydronaphtho[1,2-d]thiazol-6-yl)oxy]acetic Acid Using ethyl[(2-mercapto-4,5-dihydronaphtho[1,2-d]thiazol-6-yl)oxy]acetate and (phenyl)(4-trifluoromethylphenyl)methyl bromide, the procedure-of Example 63 was otherwise repeated to synthesize the title compound. Yield 71%. Amorphous solid.

$^1$H-NMR (CDCl$_3$) δ: 2.85–2.93 (2H, m), 3.07–3.14 (2H, m), 4.00–5.00 (1H, br), 4.67 (2H, s), 6.14 (1H, s), 6.48 (1H, d, J=8.4 Hz), 7.18–7.65 (11H, m).

Example 73

[(2-(4-Cyanophenyl)(phenyl)methylthio-4,5-dihydronaphtho[1,2-d]thiazol-6-yl)oxy]acetic Acid Using ethyl[(2-mercapto-4,5-dihydronaphtho[1,2-d]thiazol-6-yl)oxy]acetate and (4-cyanophenyl)(phenyl)methyl bromide, the procedure of Example 63 was otherwise repeated to synthesize the title compound. Yield 68%. Amorphous solid.

$^1$H-NMR (CDCl$_3$) δ: 2.60–3.40 (1H, br), 2.87–2.94 (2H, m), 3.05–3.13 (2H, m), 4.72 (2H, s), 6.14 (1H, s), 6.72 (1H, d, J=8.0 Hz), 7.19–7.43 (7H, m), 7.53 (1H, d, J=7.2 Hz), 7.61 (3H, s).

Example 74

[(2-(3-Chlorophenyl)(phenyl)methylthio-4,5-dihydronaphtho[1,2-d]thiazol-6-yl)oxy]acetic Acid Using ethyl[(2-mercapto-4,5-dihydronaphtho[1,2-d]thiazol-6-yl)oxy]acetate and (3-chlorophenyl)(phenyl)methyl bromide, the procedure of Example 63 was otherwise repeated to synthesize the title compound. Yield 64%. Amorphous solid.

$^1$H-NMR (CDCl$_3$) δ: 2.85–2.93 (2H, m), 3.04–3.13 (2H, m), 4.20–5.00 (1H, br), 4.72 (2H, s), 6.03 (1H, s), 6.71 (1H, d, J=7.6 Hz), 7.19–7.60 (11H, m).

Example 75

[(2-(2-Chlorophenyl)(phenyl)methylthio-4,5-dihydronaphtho[1,2-d]thiazol-6-yl)oxy]acetic Acid Using ethyl[(2-mercapto-4,5-dihydronaphtho[1,2-d]thiazol-6-yl)oxy]acetate and (2-chlorophenyl)(phenyl)methyl bromide, the procedure of Example 63 was otherwise repeated to synthesize the title compound. Yield 63%. Amorphous solid.

$^1$H-NMR (CDCl$_3$) δ: 2.82–2.91 (2H, m), 3.02–3.10 (2H, m), 4.20–4.80 (1H, br), 4.71 (2H, s), 6.00 (1H, s), 6.70 (1H, d, J=8.4 Hz), 6.82–6.88 (2H, m), 7.18–7.61 (9H, m).

Example 76

[(2-(3-Methylphenyl)(phenyl)methylthio-4,5-dihydronaphtho[1,2-d]thiazol-6-yl)oxy]acetic Acid Using ethyl[(2-mercapto-4,5-dihydronaphtho[1,2-d]thiazol-6-yl)oxy]acetate and (3-methylphenyl)(phenyl)methyl bromide, the procedure of Example 63 was otherwise repeated to synthesize the title compound. Yield 72%. Amorphous solid.

$^1$H-NMR (CDCl$_3$) δ: 2.32 (3H, s), 2.84–2.92 (2H, m), 3.05–3.13 (2H, m), 4.20–5.00 (1H, br), 4.66 (2H, s), 6.01 (1H, s), 6.68 (1H, d, J=7.2 Hz), 7.06 (1H, d, J=7.2 Hz), 7.17, 7.36 (7H, m), 7.46–7.51 (2H, m), 7.58 (1H, d, J=7.8 Hz).

Example 77

[(2-(2-Methylphenyl)(phenyl)methylthio-4,5-dihydronaphtho[1,2-d]thiazol-6-yl)oxy]acetic Acid Using ethyl[(2-mercapto-4,5-dihydronaphtho[1,2-d]thiazol-6-yl)oxy]acetate and (2-methylphenyl)(phenyl)methyl bromide, the procedure of Example 63 was otherwise repeated to synthesize the title compound. Yield 61%. Amorphous solid.

$^1$H-NMR (CDCl$_3$) δ: 2.43 (3H, s), 2.84–2.92 (2H, m), 3.06–3.14 (2H, m), 4.00–4.80 (1H, br), 4.74 (2H, s), 6.29 (1H, s), 6.67 (1H, d, J=8.2 Hz), 7.18–7.65 (11H, m).

Example 78

Ethyl[(2-(4-nitrophenyl)(phenyl)methylthio-4,5-dihydronaphtho[1,2-d]thiazol-6-yl)oxy]acetate Using ethyl[(2-mercapto-4,5-dihydronaphtho[1,2-d]thiazol-6-yl)oxy]acetate and (4-nitrophenyl)(phenyl)methyl bromide, the procedure of Example 48 was otherwise repeated to synthesize the title compound. Yield 61%.

m.p. 128–129° C. (tetrahydrofuran-diethyl ether)

$^1$H-NMR (CDCl$_3$) δ: 1.30 (3H, t, J=7.2 Hz), 2.85–2.94 (2H, m), 3.07–3.14 (2H, m), 4.27 (2H, q, J=7.2 Hz), 4.65 (2H, s), 6.20 (1H, s), 6.69 (1H, d, J=8.0 Hz), 7.18–7.52 (7H, m), 7.66–7.72 (2H, m), 8.15–8.20 (2H, m).

Example 79
[(2-(Phenyl)(3-trifluoromethylphenyl)methylthio-4,5-dihydronaphtho[1,2-d]thiazol-6-yl)oxy]acetic Acid Using ethyl[(2-mercapto-4,5-dihydronaphtho[1,2-d]thiazol-6-yl)oxy]acetate and (phenyl)(3-trifluoromethylphenyl)methyl bromide, the procedure of Example 63 was otherwise repeated to synthesize the title compound. Yield 59%. Amorphous solid.

$^1$H-NMR (CDCl$_3$) δ: 2.83–2.92 (2H, m), 3.07–3.17 (2H, m), 3.80–4.90 (1H, br), 4.62 (2H, s), 6.01 (1H, s), 6.74 (1H, d, J=8.0 Hz), 7.05–7.59 (11H, m).

Example 80
[(2-(2-Fluorophenyl)(phenyl)methylthio-4,5-dihydronaphtho[1,2-d]thiazol-6-yl)oxy]acetic Acid Using ethyl[(2-mercapto-4,5-dihydronaphtho[1,2-d]thiazol-6-yl)oxy]acetate and (2-fluorophenyl)(phenyl)methyl bromide, the procedure of Example 63 was otherwise repeated to synthesize the title compound. Yield 62%. Amorphous solid.

$^1$H-NMR (CDCl$_3$) δ: 2.84–2.92 (2H, m), 3.06–3.14 (2H, m), 4.62 (2H, s), 6.37 (1H, s), 6.72 (1H, d, J=8.4 Hz), 6.99–7.56 (10H, m), 7.69 (1H, t, J=7.5 Hz), 6.80–7.80 (1H, br).

Example 81
[(2-(4-Methylphenyl)(phenyl)methylsulfonyl-4,5-dihydronaphtho[1,2-d]thiazol-6-yl)oxy]acetic Acid Using ethyl[(2-mercapto-4,5-dihydronaphtho[1,2-d]thiazol-6-yl)oxy]acetate and (4-methylphenyl)(phenyl)methyl bromide, the procedure of Example 51 was otherwise repeated to synthesize the title compound. Yield 30%. Amorphous solid.

$^1$H-NMR (CDCl$_3$) δ: 2.31 (3H, s), 2.94–3.03 (2H, m), 3.09–3.17 (2H, m), 3.20–4.20 (1H, br), 4.75 (2H, s), 5.92 (1H, s), 6.79 (1H, d, J=7.4 Hz), 7.15 (2H, d, J=8.0 Hz), 7.29–7.35 (4H, m), 7.51 (2H, d, J=8.0 Hz), 7.58–7.63 (2H, m), 7.73 (1H, d, J=7.4 Hz).

Example 82
[(2-(Diphenylmethylsulfonyl)-4H-[1]benzopyrano[4,3-d]thiazol-6-yl)oxy]acetic Acid Using ethyl[(2-mercapto-4H-[1]benzopyrano[4,3-d]thiazol-6-yl)oxy]acetate and bromodiphenylmethane, the procedure of Example 51 was otherwise repeated to synthesize the title compound. Yield 55%.

m.p. 168° C. (decomp.) $^1$H-NMR (CDCl$_3$) δ: 2.00–2.90 (1H, br), 4.73 (2H, s), 5.45 (2H, s), 5.94 (1H, s), 6.91–6.95 (1H, m), 7.06 (1H, t, J=7.6 Hz), 7.28–7.38 (6H, m), 7.60–7.66 (5H, m).

Example 83
[(2-(4-Chlorophenyl)(phenyl)methylsulfonyl-4,5-dihydronaphtho[1,2-d]thiazol-6-yl)oxy]acetic Acid Using ethyl[(2-mercapto-4,5-dihydronaphtho[1,2-d]thiazol-6-yl)oxy]acetate and (4-chlorophenyl)(phenyl)methyl bromide, the procedure of Example 51 was otherwise repeated to synthesize the title compound. Yield 55%.

m.p. 180–181° C. (ethyl acetate-hexane)

$^1$H-NMR (CDCl$_3$) δ: 3.01–3.13 (4H, m), 3.20–4.40 (1H, br), 4.76 (2H, s), 5.93 (1H, s), 6.79 (1H, d, J=8.0 Hz), 7.29–7.35 (6H, m), 7.55–7.73 (5H, m).

Example 84
[(2-(4-Fluorophenyl)(phenyl)methylsulfonyl-4,5-dihydronaphtho[1,2-d]thiazol-6-yl)oxy]acetic Acid Using-ethyl[(2-mercapto-4,5-dihydronaphtho[1,2-d]thiazol-6-yl)oxy]acetate and (4-fluorophenyl)(phenyl)methyl bromide, the procedure of Example 51 was otherwise repeated to synthesize the title compound. Yield 38%.

m.p. 210–211° C. (tetrahydrofuran-diethyl ether)

$^1$H-NMR (CDCl$_3$+DMSO-d$_6$) δ: 2.95–3.04 (2H, m), 3.11–3.20 (2H, m), 4.66 (2H, s), 5.94 (1H, s), 6.81 (1H, d, J=8.2 Hz), 7.04–7.08 (2H, m), 7.26–7.36 (4H, m), 7.57–7.69 (5H, m), 1H not confirmed.

Example 85
[(2-Bis(4-fluorophenyl)methylsulfonyl-4,5-dihydronaphtho[1,2-d]thiazol-6-yl)oxy]acetic Acid Using ethyl[(2-mercapto-4,5-dihydronaphtho[1,2-d]thiazol-6-yl)oxy]acetate and bis(4-fluorophenyl)methyl bromide, the procedure of Example 51 was otherwise repeated to synthesize the title compound. Yield 38%.

m.p. 186–188° C. (ethyl acetate-hexane)

$^1$H-NMR (CDCl$_3$+DMSO-d$_6$) δ: 3.06 (4H, s) 3.20–4.40 (1H, br), 4.72 (2H, s), 6.42 (1H, s), 6.90 (1H, d, J=8.4 Hz), 7.14–7.33 (5H, m), 7.49 (1H, d, J=7.6 Hz), 7.66–7.73 (4H, m).

Example 86
[(2-Bis(4-chlorophenyl)methylsulfonyl-4,5-dihydronaphtho[1,2-d]thiazol-6-yl)oxy]acetic Acid Using ethyl[(2-mercapto-4,5-dihydronaphtho[1,2-d]thiazol-6-yl)oxy]acetate and bis(4-chlorophenyl)methyl bromide, the procedure of Example 51 was otherwise repeated to synthesize the title compound. Yield 55%.

m.p. 197–199° C. (ethyl acetate-hexane)

$^1$H-NMR (CDCl$_3$) δ: 3.03–3.14 (4H, m), 3.40–4.20 (1H, br), 4.76 (2H, s), 5.91 (1H, s), 6.80 (1H, d, J=7.6 Hz), 7.27–7.34 (5H, m), 7.50–7.54 (4H, m), 7.68 (1H, d, J=7.6 Hz).

Example 87
[(2-(Phenyl)(4-trifluoromethylphenyl)methylsulfonyl-4,5-dihydronaphtho[1,2-d]thiazol-6-yl)oxy]acetic Acid Using ethyl[(2-mercapto-4,5-dihydronaphtho[1,2-d]thiazol-6-yl)oxy]acetate and (phenyl)(4-trifluoromethylphenyl)methyl bromide, the procedure of Example 51 was otherwise repeated to synthesize the title compound. Yield 55%.

m.p. 188–190° C. (tetrahydrofuran-diethyl ether)

$^1$H-NMR (CDCl$_3$) δ: 2.86–2.94 (2H, m), 3.01–3.10 (2H, m), 4.60 (2H, s), 5.91 (1H, s), 6.67 (1H, d, J=8.4 Hz), 7.16–7.26 (4H, m), 7.45–7.59 (5H, m), 7.69 (2H, d, J=8.0 Hz), 1H not confirmed.

Example 88
[(2-(4-Cyanophenyl)(phenyl)methylsulfonyl-4,5-dihydronaphtho[1,2-d]thiazol-6-yl)oxy]acetic Acid Using ethyl[(2-mercapto-4,5-dihydronaphtho[1,2-d]thiazol-6-yl)oxy]acetate and (4-cyanophenyl)(phenyl)methyl bromide, the procedure of Example 51 was otherwise repeated to synthesize the title compound. Yield 40%.

m.p. 200–201° C. (ethyl acetate-diethyl ether)

$^1$H-NMR (CDCl$_3$) δ: 2.82–2.89 (2H, m), 3.03–3.10 (2H, m), 4.09 (2H, s), 6.11 (1H, s), 6.70 (1H, d, J=8.2 Hz), 7.16–7.69 (11H, m), 9.20–9.40 (1H, br).

Example 89
[(2-(3-Chlorophenyl)(phenyl)methylsulfonyl-4,5-dihydronaphtho[1,2-d]thiazol-6-yl)oxy]acetic Acid Using ethyl[(2-mercapto-4,5-dihydronaphtho[1,2-d]thiazol-6-yl)oxy]acetate and (3-chlorophenyl)(phenyl)methyl bromide, the procedure of Example 51 was otherwise repeated to synthesize the title compound. Yield 45%.

m.p. 173–174° C. (ethyl acetate-hexane)
$^1$H-NMR (DMSO-$d_6$) δ: 2.97–3.13 (4H, m), 3.00–3.80 (1H, br), 4.74 (2H, s), 6.48 (1H, s), 6.93 (1H, d, J=7.4 Hz), 7.27–7.49 (7H, m), 7.64–7.73 (4H, m).

Example 90
[(2-(2-Chlorophenyl)(phenyl)methylsulfonyl-4,5-dihydronaphtho[1,2-d]thiazol-6-yl)oxy]acetic Acid Using ethyl[(2-mercapto-4,5-dihydronaphtho[1,2-d]thiazol-6-yl)oxy]acetate and (2-chlorophenyl)(phenyl)methyl bromide, the procedure of Example 51 was otherwise repeated to synthesize the title compound. Yield 70%.
m.p. 197–198° C. (ethyl acetate-hexane)
$^1$H-NMR (DMSO-$d_6$) δ: 2.95–3.05 (4H, m), 4.75 (2H, s), 6.55 (1H, s), 6.93 (1H, d, J=8.0 Hz), 7.30 (1H, t, J=8.0 Hz), 7.39–7.57 (9H, m), 8.24 (1H, d, J=8.0 Hz), 1H not confirmed.

Example 91
[(2-(3-Methylphenyl)(phenyl)methylsulfonyl-4,5-dihydronaphtho[1,2-d]thiazol-6-yl)oxy]acetic Acid Using ethyl[(2-mercapto-4,5-dihydronaphtho[1,2-d]thiazol-6-yl)oxy]acetate and (3-methylphenyl)(phenyl)methyl bromide, the procedure of Example 51 was otherwise repeated to synthesize the title compound. Yield 63%.
m.p. 185–186° C. (tetrahydrofuran-diethyl ether)
$^1$H-NMR (CDCl$_3$) δ: 2.31 (3H, s), 2.94–3.02 (2H, m), 3.09–3.17 (2H, m), 4.00–5.20 (1H, br), 4.75 (2H, s), 5.91 (1H, s), 6.79 (1H, d, J=8.0 Hz), 7.10–7.44 (8H, m), 7.57–7.62 (2H, m), 7.34 (1H, d, J=8.0 Hz).

Example 92
[(2-(2-Methylphenyl)(phenyl)methylsulfonyl-4,5-dihydronaphtho[1,2-d]thiazol-6-yl)oxy]acetic Acid Using ethyl[(2-mercapto-4,5-dihydronaphtho[1,2-d]thiazol-6-yl)oxy]acetate and (2-methylphenyl)(phenyl)methyl bromide, the procedure of Example 51 was otherwise repeated to synthesize the title compound. Yield 49%.
m.p. 192–193° C. (tetrahydrofuran-diethyl ether)
$^1$H-NMR (CDCl$_3$+DMSO-$d_6$) δ: 2.32 (3H, s), 2.94–3.19 (4H, m), 4.20–5.00 (1H, br), 4.65 (2H, s), 6.28 (1H, s), 6.80 (1H, d, J=8.6 Hz), 7.06–7.36 (7H, m), 7.54–7.58 (2H, m), 7.67 (1H, d, J=7.2 Hz), 8.17 (1H, d, J=7.2 Hz).

Example 93
Ethyl[(2-(4-nitrophenyl)(phenyl)methylsulfonyl-4,5-dihydronaphtho[1,2-d]thiazol-6-yl)oxy]acetate Using ethyl[(2-mercapto-4,5-dihydronaphtho[1,2-d]thiazol-6-yl)oxy]acetate and (4-nitrophenyl)(phenyl)methyl bromide, the procedure of Example 50 was otherwise repeated to synthesize the title compound. Yield 49%.
m.p. 146–148° C. (diethyl ether-hexane)
$^1$H-NMR (CDCl$_3$) δ: 1.22 (3H, t, J=7.4 Hz), 2.85–3.10 (4H, m), 4.19 (2H, q, J=7.2 Hz), 4.59 (2H, s), 5.97 (1H, s), 6.67 (1H, d, J=8.4 Hz), 7.17–7.28 (4H, m), 7.44–7.48 (2H, m), 7.57 (1H, d, J=7.8 Hz), 7.76 (2H, d, J=9.0 Hz), 8.11 (2H, d, J=9.0 Hz).

Example 94
[(2-(Phenyl)(3-trifluoromethylphenyl)methylsulfonyl-4,5-dihydronaphtho[1,2-d]thiazol-6-yl)oxy]acetic Acid Using ethyl[(2-mercapto-4,5-dihydronaphtho[1,2-d]thiazol-6-yl)oxy]acetate and (phenyl)(3-trifluoromethylphenyl)methyl bromide, the procedure of Example 51 was otherwise repeated to synthesize the title compound. Yield 71%.
m.p. 180–182° C. (tetrahydrofuran-diethyl ether)
$^1$H-NMR (DMSO-$d_6$) δ: 2.87–3.13 (4H, m), 3.00–3.60 (1H, br), 4.76 (2H, s), 6.35 (1H, s), 6.83 (1H, d, J=7.4 Hz), 7.14–7.45 (7H, m), 7.60–7.71 (4H, m).

Example 95
[(2-(2-Fluorophenyl)(phenyl)methylsulfonyl-4,5-dihydronaphtho[1,2-d]thiazol-6-yl)oxy]acetic Acid Using ethyl[(2-mercapto-4,5-dihydronaphtho[1,2-d]thiazol-6-yl)oxy]acetate and (2-fluorophenyl)(phenyl)methyl bromide, the procedure of Example 51 was otherwise repeated to synthesize the title compound. Yield 71%.
m.p. 192–193° C. (tetrahydrofuran-diethyl ether)
$^1$H-NMR (DMSO-$d_6$) δ: 3.06 (4H, s), 2.80–3.80 (1H, br), 4.72 (2H, s), 6.36 (1H, s), 6.91 (1H, d, J=7.4 Hz), 7.12–7.50 (8H, m), 7.60–7.65 (2H, m), 8.03–8.11 (1H, m).

Example 96
[(2-Bis(3-fluorophenyl)methylthio-4,5-dihydronapto[1,2-d]thiazol-6-yl)oxy]acetic Acid Using ethyl[(2-mercapto-4,5-dihydronapto[1,2-d]thiazol-6-yl)oxy]acetate and bis(3-fluorophenyl)methylbromide, the procedure of Example 63 was otherwise repeated to synthesize the title compound. Yield 47%.
m.p. 155–158° C. (ethyl acetate-hexane)
$^1$H-NMR (CDCl$_3$) δ: 2.84–3.14 (4H, m), 4.71 (2H, s), 6.06 (1H, s), 6.71 (1H, d, J=8.0 Hz), 6.90–7.42 (10H, m), 7.56 (11H, d, J=7.8 Hz).

Example 97
[(2-Bis(2-fluorophenyl)methylthio-4,5-dihydronapto[1,2-d]thiazol-6-yl)oxy]acetic Acid Using ethyl[(2-mercapto-4,5-dihydronapto[1,2-d]thiazol-6-yl)oxy]acetate and bis(2-fluorophenyl)methylbromide, the procedure of Example 63 was otherwise repeated to synthesize the title compound. Yield 58%.
m.p. 194–196° C. (ethyl acetate)
$^1$H-NMR (DMSO-$d_6$) δ: 2.84–3.09 (4H, m), 4.70 (2H, s), 6.64 (1H, s), 6.82 (1H, d, J=8.0 Hz), 7.10–7.47 (8H, m), 7.58–7.72 (2H, m), 1H not confirmed.

Example 98
[(2-Bis(3-fluorophenyl)methylsulfonyl-4,5-dihydronapto[1,2-d]thiazol-6-yl)oxy]acetic Acid Using ethyl[(2-mercapto-4,5-dihydronapto[1,2-d]thiazol-6-yl)oxy]acetate and bis(3-fluorophenyl)methylbromide, the procedure of Example 51 was otherwise repeated to synthesize the title compound. Yield 28%.
m.p. 213–214° C. (ethyl acetate)
$^1$H-NMR (DMSO-$d_6$) δ: 2.82–3.08 (4H, m), 4.70 (2H, s), 6.64 (1H, s), 6.82 (1H, d, J=8.0 Hz), 7.15–7.47 (8H, m), 7.58–7.76 (2H, m), 1H not confirmed.

Example 99
[(2-Bis(2-fluorophenyl)methylsulfonyl-4,5-dihydronapto[1,2-d]thiazol-5-yl)oxy]acetic Acid Using ethyl[(2-mercapto-4,5-dihydronapto[1,2-d]thiazol-6-yl)oxy]acetate and bis(2-fluorophenyl)methylbromide, the procedure of Example 51 was otherwise repeated to synthesize the title compound. Yield 38%.
m.p. 204–208° C. (ethanol)
$^1$H-NMR (CDCl$_3$) δ: 2.95–3.21 (4H, m), 4.74 (2H, s), 6.74–6.82 (2H, m), 7.00 (2H, t, J=9.2 Hz), 7.04–7.39 (5H, m), 7.66 (1H, d, J=7.6 Hz), 7.98–9.00 (3H, m).

Example 100
Sodium[(2-diphenylmethylthio-4,5-dihydronapto[1,2-d]thiazol-6-yl)oxy]acetate To a solution of [(2-diphenylmethylthio-4,5-dihydronapto[1,2-d]thiazol-6-yl)oxy]acetic acid (1.00 g, 1.09 mmol) in ethanol (50 mL) was added 1N-aqueous sodium hydroxide solution (2.2 mL) dropwise and the mixture was stirred at room temperature for 20 minutes. The solvent was then distilled off under reduced pressure. The residue was recrystallized from ethanol/water to provide 0.48 g of the title compound.

Yield 46%.

m.p. 223–225° C.

$^1$H-NMR (DMSO-d$_6$) δ: 2.79–3.04 (4H, m), 4.18 (2H, s), 6.16 (1H, s), 6.71 (1H, d, J=7.4 Hz), 7.08–7.42 (8H, m), 7.52–7.62 (4H, m).

Example 101
Sodium[(2-diphenylmethylsulfonyl-4,5-dihydronaphto[1,2-d]thiazol-6-yl)oxy]acetate Using [(2-diphenylmethylsulfonyl-4,5-dihydronaphto[1,2-d]thiazol-6-yl)oxy]acetic acid, the procedure of Example 100 was otherwise repeated to synthesize the title compound. Yield 48%.

m.p. 226–228° C. (water)

$^1$H-NMR (DMSO-d$_6$) δ: 2.83–3.11 (4H, m), 4.30 (2H, s), 6.30 (1H, s), 6.83 (1H, d, J=8.4 Hz), 7.11–7.42 (8H, m), 7.58–7.75 (4H, m).

Example 102
Ethyl[(2-phenylamino-benzofuro[3,2-d]thiazol-5-yl)oxy]acetate

To a solution of ethyl[(3-oxo-2,3-dihydrobenzofuran-7-yl)oxy]acetate (1.00 g, 4.23 mmol) in chloroform (30 mL) was added pyridinium hydrobromide perbromide (1.35 g, 4.23 mmol) at 0° C. and the mixture was stirred at room temperature for 30 minutes. The reaction mixture was poured into water. The organic layer was washed with water, dried over MgSO$_4$, and filtered. The filtrate was concentrated under reduced pressure to provide 1.20 g of ethyl[(2-bromo-3-oxo-2,3-dihydrobenzofuran-7-yl)oxy]acetate. A mixture of this compound (1.20 g, 3.80 mmol) and 1-phenyl-2-thiourea (580 mg, 3.80 mmol) in acetic acid (20 mL) was refluxed for 3 hours. The solvent was then distilled off under reduced pressure. To that residue was added water, and the mixture was extracted with ethyl acetate. The organic layer was washed with water, dried over MgSO$_4$, and filtered. The filtrate was concentrated under reduced pressure, and the residue was purified by silica gel column chromatography (ethyl acetate-hexane=1:5) to provide 180 mg of the title compound. Yield 12%.

m.p. 196–198° C. (ethyl acetate-hexane)

$^1$H-NMR (CDCl$_3$) δ: 1.30 (3H, t, J=7.0 Hz), 4.29 (2H, q, J=7.0 Hz), 4.87 (2H, s), 6.79 (1H, d, J=7.8 Hz), 7.04–7.45 (8H, m).

Example 103
[(2-(3-Fluorophenyl)(phenyl)methylthio-4,5-dihydronaphto[1,2-d]thiazol-6-yl)oxy]acetic Acid Using ethyl[(2-mercapto-4,5-dihydronaphto[1,2-d]thiazol-6-yl)oxy]acetate and (3-fluorophenyl)(phenyl)methylbromide, the procedure of Example 63 was otherwise repeated to synthesize the title compound. Yield 38%.

m.p. 159–161° C. (ethyl acetate) 332 $^1$H-NMR (CDCl$_3$) δ: 2.82–3.08 (4H, m), 4.70 (2H, s), 5.40–6.00 (1H, br), 6.71 (1H, d, J=8.0 Hz), 6.92–7.01 (1H, m), 7.18–7.50 (10H, m), 7.57 (1H, d, J=7.6 Hz).

Example 104
[(2-(3-Fluorophenyl)(phenyl)methylsulfonyl-4,5-dihydronaphto[1,2-d]thiazol-6-yl)oxy]acetic Acid Using ethyl[(2-mercapto-4,5-dihydronaphto[1,2-d]thiazol-6-yl)oxy]acetate and (3-fluorophenyl)(phenyl)methylbromide, the procedure of Example 51 was otherwise repeated to synthesize the title compound. Yield 27%.

m.p. 215–217° C. (ethanol)

$^1$H-NMR (DMSO-d$_6$) δ: 2.90–3.10 (4H, m), 4.74 (2H, s), 6.43 (1H, s), 6.92 (1H, d, J=8.2 Hz), 7.10–7.69 (11H, m), 1H not confirmed.

The chemical formulas of the compounds obtained in Examples 1 to 104 are shown in Tables 1 to 7.

TABLE 1

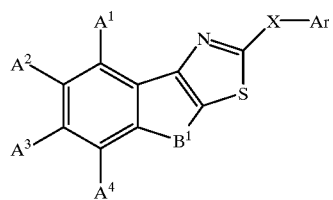

| Ex. No. | A$^1$ | A$^2$ | A$^3$ | A$^4$ | B$^1$ | X | Ar |
|---|---|---|---|---|---|---|---|
| 1 | H | H | H | OCH$_2$COOH | CH$_2$CH$_2$ | S—CH$_2$CH(Ph) | Ph |
| 2 | H | H | H | OCH$_2$COOH | CH$_2$ | S—CH$_2$ | Ph |
| 3 | H | H | H | OCH$_2$COOH | CH$_2$CH$_2$ | S—CH$_2$ | Ph |
| 4 | H | H | H | OCH$_2$COOH | CH$_2$ | S—CH$_2$CH=CH (E) | Ph |
| 5 | H | H | H | OCH$_2$COOH | CH$_2$CH$_2$ | S—CH$_2$CH=CH (E) | Ph |
| 6 | H | H | H | OCH$_2$COOH | CH$_2$ | S—CH$_2$CH$_2$CH(Ph) | Ph |
| 7 | H | H | H | OCH$_2$COOH | CH$_2$CH$_2$ | S—CH$_2$CH$_2$CH(Ph) | Ph |

TABLE 1-continued

| Ex. No. | A¹ | A² | A³ | A⁴ | B¹ | X | Ar |
|---|---|---|---|---|---|---|---|
| 8 | H | H | H | OCH$_2$COOH | CH$_2$ | S—CH$_2$CH(Ph) | Ph |
| 9 | H | H | H | OCH$_2$COOH | CH$_2$CH$_2$ | S—CH$_2$CH$_2$CH$_2$CH(Ph) | Ph |
| 10 | H | H | OCH$_2$COOH | H | CH$_2$CH$_2$ | S—CH$_2$CH$_2$CH(Ph) | Ph |
| 11 | H | H | H | OCH$_2$COOH | OCH$_2$ | S—CH$_2$CH$_2$CH(Ph) | Ph |
| 12 | H | H | H | OCH$_2$COOH | OCH$_2$ | S—CH$_2$CH(Ph) | Ph |
| 13 | H | H | H | OCH$_2$COOH | OCH$_2$ | S—CH(Ph) | Ph |
| 14 | H | H | H | OCH$_2$COOH | CH$_2$CH$_2$ | S—CH$_2$ | 4-biphenylyl |
| 15 | H | H | H | OCH$_2$COOH | CH$_2$CH$_2$ | S—CH(Ph) | 2-naphthyl |
| 16 | H | H | OCH$_2$COOH | H | CH$_2$CH$_2$ | S—CH(Ph) | Ph |

TABLE 2

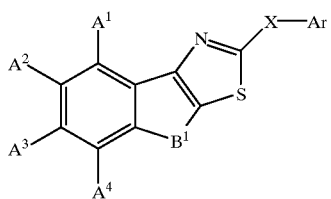

| Ex. No. | A¹ | A² | A³ | A⁴ | B¹ | X | Ar |
|---|---|---|---|---|---|---|---|
| 17 | H | H | H | OCH₂COOH | OCH₂ | S—CH(Ph) | 2-naphthyl |
| 18 | H | H | H | OCH₂COOH | CH₂ | S—CH₂CH₂CH₂CH(Ph) | Ph |
| 19 | H | H | H | OCH₂CH₂CH₂COOH | CH₂ | S—CH₂CH(Ph) | Ph |
| 20 | H | H | H | OCH₂CH₂CH₂COOH | CH₂ | S—CH₂CH₂CH(Ph) | Ph |
| 21 | H | H | H | OCH₂COOH | CH₂CH₂ | S—CH(Ph) | Ph |
| 22 | H | H | H | OCH₂CH₂COOH | CH₂CH₂ | S—CH₂CH(Ph) | Ph |
| 23 | H | H | H | OCH₂CH₂COOH | CH₂ | S—CH₂CH₂CH(Ph) | Ph |
| 24 | H | H | OCH₂COOH | H | CH₂ | S—CH₂CH₂CH(Ph) | Ph |
| 25 | CH₃ | H | CH₃ | OCH₂COOH | CH₂ | S—CH₂CH₂CH(Ph) | Ph |
| 26 | CH₃ | CH₃ | H | OCH₂COOH | CH₂ | S—CH₂CH₂CH(Ph) | Ph |
| 27 | H | H | H | OCH₂COOH | CH₂ | S—CH(Ph) | Ph |
| 28 | H | H | H | OCH₂CH₂COOH | CH₂CH₂ | S—CH(Ph) | Ph |
| 29 | H | H | H | OCH₂COOH | CH₂CH₂ | SO₂—CH₂CH(Ph) | Ph |

TABLE 3

| Ex. No. | A¹ | A² | A³ | A⁴ | B¹ | X | Ar |
|---|---|---|---|---|---|---|---|
| 30 | H | H | H | OCH$_2$COOH | CH$_2$ | SO$_2$—CH$_2$CH=CH (E) | Ph |
| 31 | H | H | H | OCH$_2$COOH | CH$_2$CH$_2$ | SO$_2$—CH$_2$CH=CH (E) | Ph |
| 32 | H | H | H | OCH$_2$COOH | CH$_2$CH$_2$ | SO$_2$—CH$_2$CH$_2$CH(Ph) | Ph |
| 33 | H | H | H | OCH$_2$COOH | CH$_2$CH$_2$ | SO$_2$—CH$_2$CH$_2$CH$_2$CH(Ph) | Ph |
| 34 | H | H | OCH$_2$COOH | H | CH$_2$CH$_2$ | SO$_2$—CH$_2$CH$_2$CH(Ph) | Ph |
| 35 | H | H | H | OCH$_2$COOH | OCH$_2$ | SO$_2$—CH$_2$CH$_2$CH(Ph) | Ph |
| 36 | H | H | H | OCH$_2$COOH | CH$_2$ | SO$_2$—CH$_2$CH$_2$CH(Ph) | Ph |
| 37 | H | H | H | OCH$_2$COOH | CH$_2$ | SO$_2$—CH$_2$CH$_2$CH$_2$CH(Ph) | Ph |
| 38 | H | H | H | OCH$_2$CH$_2$COOH | CH$_2$ | SO$_2$—CH$_2$CH$_2$CH(Ph) | Ph |
| 39 | H | H | OCH$_2$COOH | H | CH$_2$ | SO$_2$—CH$_2$CH$_2$CH(Ph) | Ph |
| 40 | H | H | H | OCH$_2$COOH | CH$_2$CH$_2$ | O—CH$_2$CH$_2$CH(Ph) | Ph |
| 41 | H | H | H | OCH$_2$COOH | CH$_2$CH$_2$ | NH—CH$_2$CH$_2$CH(Ph) | Ph |
| 42 | H | H | H | OCH$_2$COOH | CH$_2$CH$_2$ | NH—CH(Ph) | Ph |
| 43 | H | H | H | OCH$_2$COOH | CH$_2$CH$_2$ | NH—CH$_2$CH(Ph) | Ph |

TABLE 4

[Structure: benzothiazole core with substituents A¹, A², A³, A⁴ on benzene ring, B¹ bridge, and 2-position substituent X—Ar]

| Ex. No. | A¹ | A² | A³ | A⁴ | B¹ | X | Ar |
|---|---|---|---|---|---|---|---|
| 44 | H | H | H | OCH₂COOH | CH₂ | NH—CH₂CH(Ph) | Ph |
| 45 | H | H | H | OCH₂COOH | CH₂ | NH—CH₂CH₂CH(Ph) | Ph |
| 46 | H | H | H | OCH₂COOH | CH₂CH₂ | S—CHCH₂(Ph) | Ph |
| 47 | H | H | H | OCH₂COOH | CH₂CH₂ | NH | Ph |
| 48 | H | H | H | OCH₂COOEt | CH₂CH₂ | S—CH(Ph) | Ph |
| 49 | H | H | H | OCH₂COOEt | CH₂CH₂ | S—CH₂CH(Ph) | Ph |
| 50 | H | H | H | OCH₂COOEt | CH₂CH₂ | SO₂—CH(Ph) | Ph |
| 51 | H | H | H | OCH₂COOH | CH₂CH₂ | SO₂—CH(Ph) | Ph |
| 52 | H | H | H | OCH₂COOH | CH₂CH₂ | CH₂ | Ph |
| 53 | H | H | H | OCH₂COOH | CH₂CH₂ | CH(Ph) | Ph |
| 54 | H | H | H | OCH₂COOH | CH₂CH₂ | — | Ph |
| 55 | H | H | H | OCH₂COOH | CH₂CH₂ | CH₂CH(Ph) | Ph |
| 56 | H | H | H | OCH₂COOH | CH₂CH₂ | S | 2,4-di-NO₂—Ph |
| 57 | H | OCH₂COOH | H | H | CH₂CH₂ | S—CH(Ph) | Ph |
| 58 | H | OCH₂COOH | H | H | CH₂CH₂ | S—CH₂CH(Ph) | Ph |
| 59 | H | OCH₂COOH | H | H | CH₂CH₂ | SO₂—CH(Ph) | Ph |

TABLE 5

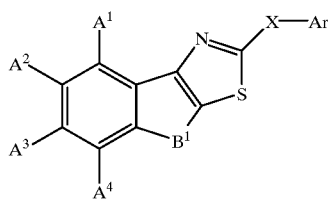

| Ex. No. | A¹ | A² | A³ | A⁴ | B¹ | X | Ar |
|---|---|---|---|---|---|---|---|
| 60 | H | OCH$_2$COOH | H | H | CH$_2$CH$_2$ | SO$_2$—CH$_2$CH(Ph) | Ph |
| 61 | H | H | H | OCH$_2$COOEt | CH$_2$CH$_2$ | SO—CH$_2$CH(Ph) | Ph |
| 62 | H | H | H | OCH$_2$COOH | CH$_2$CH$_2$ | SO—CH$_2$CH(Ph) | Ph |
| 63 | H | H | H | OCH$_2$COOH | OCH$_2$ | S—CH(Ph) | 2-naphthyl |
| 64 | H | H | H | OCH$_2$COOH | OCH$_2$ | S—CH(Ph) | 4-Me—Ph |
| 65 | H | H | H | OCH$_2$COOH | OCH$_2$ | S—CH(Ph) | 4-Cl—Ph |
| 66 | H | H | H | OCH$_2$COOH | CH$_2$CH$_2$ | S—CH(Ph) | 4-Me—Ph |
| 67 | H | H | H | OCH$_2$COOH | CH$_2$CH$_2$ | S—CH(Ph) | 4-Cl—Ph |
| 68 | H | H | H | OCH$_2$COOH | CH$_2$CH$_2$ | S—CH(Ph) | 4-F—Ph |
| 69 | H | H | H | OCH$_2$COOH | CH$_2$CH$_2$ | S—CH(4-F—Ph) | 4-F—Ph |
| 70 | H | H | H | OCH$_2$COOH | CH$_2$CH$_2$ | S—CH(4-Cl—Ph) | 4-Cl—Ph |
| 71 | H | H | H | OCH$_2$COOH | CH$_2$CH$_2$ | S—CH(Ph) | 4-MeO—Ph |
| 72 | H | H | H | OCH$_2$COOH | CH$_2$CH$_2$ | S—CH(Ph) | 4-CF$_3$—Ph |
| 73 | H | H | H | OCH$_2$COOH | CH$_2$CH$_2$ | S—CH(Ph) | 4-CN—Ph |
| 74 | H | H | H | OCH$_2$COOH | CH$_2$CH$_2$ | S—CH(Ph) | 3-Cl—Ph |

TABLE 6

| Ex. No. | A¹ | A² | A³ | A⁴ | B¹ | X | Ar |
|---|---|---|---|---|---|---|---|
| 75 | H | H | H | OCH₂COOH | CH₂CH₂ | S—CH(Ph) | 2-Cl—Ph |
| 76 | H | H | H | OCH₂COOH | CH₂CH₂ | S—CH(Ph) | 3-Me—Ph |
| 77 | H | H | H | OCH₂COOH | CH₂CH₂ | S—CH(Ph) | 2-Me—Ph |
| 78 | H | H | H | OCH₂COOEt | CH₂CH₂ | S—CH(Ph) | 4-NO₂—Ph |
| 79 | H | H | H | OCH₂COOH | CH₂CH₂ | S—CH(Ph) | 3-CF₃—Ph |
| 80 | H | H | H | OCH₂COOH | CH₂CH₂ | S—CH(Ph) | 2-F—Ph |
| 81 | H | H | H | OCH₂COOH | CH₂CH₂ | SO₂—CH(Ph) | 4-Me—Ph |
| 82 | H | H | H | OCH₂COOH | OCH₂ | SO₂—CH(Ph) | Ph |
| 83 | H | H | H | OCH₂COOH | CH₂CH₂ | SO₂—CH(Ph) | 4-Cl—Ph |
| 84 | H | H | H | OCH₂COOH | CH₂CH₂ | SO₂—CH(Ph) | 4-F—Ph |
| 85 | H | H | H | OCH₂COOH | CH₂CH₂ | SO₂—CH(4-F—Ph) | 4-F—Ph |
| 86 | H | H | H | OCH₂COOH | CH₂CH₂ | SO₂—CH(4-Cl—Ph) | 4-Cl—Ph |
| 87 | H | H | H | OCH₂COOH | CH₂CH₂ | SO₂—CH(Ph) | 4-CF₃—Ph |
| 88 | H | H | H | OCH₂COOH | CH₂CH₂ | SO₂—CH(Ph) | 4-CN—Ph |

TABLE 6-continued

| Ex. No. | A¹ | A² | A³ | A⁴ | B¹ | X | Ar |
|---|---|---|---|---|---|---|---|
| 89 | H | H | H | OCH$_2$COOH | CH$_2$CH$_2$ | SO$_2$—CH(Ph) | 3-Cl—Ph |

TABLE 7

| Ex. No. | A¹ | A² | A³ | A⁴ | B¹ | X | Ar |
|---|---|---|---|---|---|---|---|
| 90 | H | H | H | OCH$_2$COOH | CH$_2$CH$_2$ | SO$_2$—CH(Ph) | 2-Cl—Ph |
| 91 | H | H | H | OCH$_2$COOH | CH$_2$CH$_2$ | SO$_2$—CH(Ph) | 3-Me—Ph |
| 92 | H | H | H | OCH$_2$COOH | CH$_2$CH$_2$ | SO$_2$—CH(Ph) | 2-Me—Ph |
| 93 | H | H | H | OCH$_2$COOEt | CH$_2$CH$_2$ | SO$_2$—CH(Ph) | 4-NO$_2$—Ph |
| 94 | H | H | H | OCH$_2$COOH | CH$_2$CH$_2$ | SO$_2$—CH(Ph) | 3-CF$_3$—Ph |
| 95 | H | H | H | OCH$_2$COOH | CH$_2$CH$_2$ | SO$_2$—CH(Ph) | 2-F—Ph |
| 96 | H | H | H | OCH$_2$COOH | CH$_2$CH$_2$ | S—CH(3-F—Ph) | 3-F—Ph |

TABLE 7-continued

| Ex. No. | A¹ | A² | A³ | A⁴ | B¹ | X | | Ar |
|---|---|---|---|---|---|---|---|---|
| 97 | H | H | H | OCH$_2$COOH | CH$_2$CH$_2$ | S—CH<br>\|<br>2-F—Ph | | 2-F—Ph |
| 98 | H | H | H | OCH$_2$COOH | CH$_2$CH$_2$ | SO$_2$—CH<br>\|<br>3-F—Ph | | 3-F—Ph |
| 99 | H | H | H | OCH$_2$COOH | CH$_2$CH$_2$ | SO$_2$—CH<br>\|<br>2-F—Ph | | 2-F—Ph |
| 100 | H | H | H | OCH$_2$COONa | CH$_2$CH$_2$ | S—CH<br>\|<br>Ph | | Ph |
| 101 | H | H | H | OCH$_2$COONa | CH$_2$CH$_2$ | SO$_2$—CH<br>\|<br>Ph | | Ph |
| 102 | H | H | H | OCH$_2$COOEt | O | NH | | Ph |
| 103 | H | H | H | OCH$_2$COOH | CH$_2$CH$_2$ | S—CH<br>\|<br>Ph | | 3-F—Ph |
| 104 | H | H | H | OCH$_2$COOH | CH$_2$CH$_2$ | SO$_2$—CH<br>\|<br>Ph | | 3-F—Ph |

Formulation Example 1

| | | |
|---|---|---|
| (1) | Compound of Example 21 | 3.0g |
| (2) | Lactose | 60.0g |
| (3) | Corn starch | 35.0g |
| (4) | Gelatin | 3.0g |
| (5) | Magnesium stearate | 2.0g |

Using 30 mL of an aqueous solution of gelatin (10 weight %, 3.0 g as gelatin), a mixture of the compound of Example 21 (3.0 g), lactose (60.0 g), and corn starch (35.0 g) was granulated through a 1 mm-mesh sieve, dried at 40° C., and resieved. The resultant granules were mixed with 2.0 g of magnesium stearate and the mixture was compressed. The core tablets thus obtained were sugar-coated with an aqueous suspension of sucrose, titanium dioxide, talc, and gum arabic. The coated tablets were glazed with beeswax to provide 1000 finished tablets.

Experimental Example 1
PGI$_2$ Receptor Binding Assay

MES-NaOH buffer (pH 6.0) (500 μL) containing the membrane fraction (40 μg) of CHO cells caused to express human PGI$_2$ receptors, [$^3$H]Iloprost (20 nM), and a test compound solution (50 μL) was incubated at 37° C. for 1 hour and then filtered through a membrane filter to separate the membrane-bound [$^3$H]Iloprost from the non-membrane-binding [$^3$H]Iloprost. The radioactivity of the membrane-bound [$^3$H]Iloprost was determined with a liquid scintillation counter and the binding inhibition rate in each drug treatment group was determined against the specific binding of [$^3$H]Iloprost to the human PGI$_2$ receptor in the control (solvent) group.

The test compound was added at the final concentrations of $10^{-6}$ to $10^{-11}$ M and the IC$_{50}$ values were calculated from the inhibition rates at the respective concentrations.

The results are shown below.

| Compound of Example | IC$_{50}$, μM |
|---|---|
| 1 | 0.024 |
| 11 | 0.081 |
| 12 | 0.061 |
| 21 | 0.002 |
| 29 | 0.021 |

It is apparent from the above results that. compound (I) has a high affinity for the PGI$_2$ receptor.

Experimental Example 2
Platelet Aggregation Inhibition Assay

The citrated blood from healthy male adult donors was centrifuged at 1000×g for 5 seconds and 20 minutes to harvest platelet-rich plasma (PRP) and platelet-poor plasma (PPP), respectively. Then, PRP was diluted with PPP to a platelet count of 300,000/μL. The degree of platelet aggregation was measured with a platelet aggregation measuring apparatus.

In the assay cuvette, 200 μL of PRP was incubated at 37° C. for 2 minutes. Then, 20 μL of a test drug solution was added and the mixture was further incubated for 2 minutes. Thereafter, aggregation was induced by adding 20 μl of ADP solution. The aggregation in the drug treatment group was compared with the maximum aggregation in the control group to find the inhibition rate. ADP was used in the minimal concentration ($2 \times 10$ to $3 \times 10^{-5}$ M) inducing maximal aggregation in each assay.

The test compound was added at the final concentrations of $10^{-3}$ to $10^{-9}$ M and the $IC_{50}$ value was calculated from the inhibition rates at the respective concentrations.

The results are shown below.

| Compound of Example | $IC_{50}$, μM |
|---|---|
| 1 | 0.54 |
| 21 | 0.21 |

It is clear from the above results that compound (I) has potent aggregation inhibitory activity against human platelets.

INDUSTRIAL APPLICABILITY

The compound (I) of the invention has a high affinity for $PGI_2$ receptors.

The compound (I) of the invention acts as a $PGI_2$ agonist in mammals (e.g. mouse, rat, hamster, rabbit, cat, dog, bovine, sheep, monkey and human) and has platelet aggregation inhibitory, vasodilative, bronchodilative, lipid deposition inhibitory, and leukocyte activation inhibitory activities. Thus, compound (I) is useful for the pharmaceutical composition for the prophylaxis and/or treatment of transient ischemic attack (TIA), diabetic neuropathy, peripheral vascular diseases (e.g. peripheral embolism, vibration syndrome, Raynaud's disease, etc.), systemic lupus erythematosus, post-PTCA reobliteration/restenosis, atherosclerosis, thrombosis (e.g. acute phase of cerebral thrombosis, etc.), diabetic gangrene, hypertension, pulmonary hypertension, ischemic diseases (e.g. cerebral infarction, myocardial infarction, etc.), angina pectoris (e.g. stable angina, unstable angia, etc.), glomerulonephritis, diabetic nephropathy, allergy, bronchial asthma, ulcer, decubitus, coronary restenosis after coronary intervention such as atherectomy and stent implantation, thrombocytopenia during dialysis, and so on.

What is claimed is:

1. a compound of the formula:

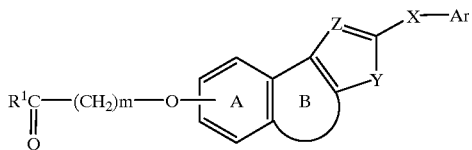

wherein $R^1$ represents hydrogen, a hydroxy which may be substituted or an amino which may be substituted;

m represents an integer of 1 to 3;

Ar represents an aromatic group which may be substituted;

X represents a bond or a divalent straight-chain group which have 1 to 6 atoms and may be substituted, Y represents —S—, wherein Z represents —N═;

ring A represents a benzene ring which may be substituted by a substituent in addition to a group of the formula: —O(CH$_2$)$_m$—COR$^1$ wherein the respective symbols have the same meanings as defined above; and ring B represents a 5- to 7-membered ring which may be substituted, or a salt thereof.

2. A compound according to claim 1 wherein $R^1$ is (i) hydrogen, (ii) a hydroxy which may be substituted by a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group, each of which may be substituted by 1 to 5 substituents selected from the group consisting of halogen, $C_{1-6}$ alkyl which may be halogenated, $C_{2-6}$ alkenyl which may be halogenated, $C_{2-6}$ alkynyl which may be halogenated, $C_{3-6}$ cycloalkyl which may be halogenated, $C_{6-10}$ aryl, $C_{7-11}$ aralkyl, $C_{1-6}$ alkoxy which may be halogenated, $C_{6-10}$ aryloxy, $C_{1-6}$ alkyl-carbonyl, $C_{6-10}$ aryl-carbonyl, $C_{7-11}$ aralkyl-carbonyl, $C_{1-6}$ alkyl-carbonyloxy, $C_{6-10}$ aryl-carbonyloxy, carboxy, $C_{l-6}$ alkoxy-carbonyl, carbamoyl, mono-$C_{1-6}$ alkyl-carbamoyl, di-$C_{1-6}$ alkyl-carbamoyl, amidino, imino, amino, mono-$C_{1-6}$ alkylamino, di-$C_{1-6}$ alkylamino, 3- to 6-membered cyclic amino, $C_{1-3}$ alkylenedioxy, hydroxy, nitro, cyano, mercapto, sulfo, sulfino, phosphono, sulfamoyl, mono-$C_{1-6}$ alkylsulfamoyl, di-$C_{1-6}$ alkylsulfamoyl, $C_{1-6}$ alkylthio which may be halogenated, $C_{6-10}$ arylthio, $C_{1-6}$ alkylsulfinyl, $C_{6-10}$ arylsulfinyl, $C_{1-6}$ alkylsulfonyl and $C_{6-10}$ arylsulfonyl, or (iii) an amino which may be substituted by 1 or 2 substituents selected from the group consisting of $C_{1-6}$ alkyl, $C_{2-6}$ alkenyl, $C_{2-6}$ alkynyl, $C_{3-6}$ cycloalkyl, $C_{6-14}$ aryl and $C_{7-16}$ aralkyl group, each of which may be substituted by 1 to 5 substituents selected from the group consisting of halogen, $C_{1-6}$ alkyl which may be halogenated, $C_{2-6}$ alkenyl which may be halogenated, $C_{2-6}$ alkynyl which may be halogenated, $C_{3-6}$ cycloalkyl which may be halogenated, $C_{6-10}$ aryl, $C_{7-11}$ aralkyl, $C_{1-6}$ alkoxy which may be halogenated, $C_{6-10}$ aryloxy, $C_{1-6}$ alkyl-carbonyl, $C_{6-10}$ aryl-carbonyl, $C_{7-11}$ aralkyl-carbonyl, $C_{1-6}$ alkyl-carbonyloxy, $C_{6-10}$ aryl-carbonyloxy, carboxy, $C_{1-6}$ alkoxy-carbonyl, carbamoyl, mono-$C_{1-6}$ alkyl-carbamoyl, di-$C_{1-6}$ alkyl-carbamoyl, amidino, imino, amino, mono-$C_{1-6}$ alkylamino, di-$C_{1-6}$ alkylamino, 3- to 6-membered cyclic amino, $C_{1-3}$ alkylenedioxy, hydroxy, nitro, cyano, mercapto, sulfo, sulfino, phosphono, sulfamoyl, mono-$C_{1-6}$ alkylsulfamoyl, di-$C_{1-6}$ alkylsulfamoyl, $C_{1-6}$ alkylthio which may be halogenated, $C_{6-10}$ arylthio, $C_{1-6}$ alkylsulfinyl, $C_{6-10}$ arylsulfinyl, $C_{1-6}$ alkylsulfonyl and $C_{6-10}$ arylsulfonyl;

m is an integer of 1 to 3;

Ar is a (i) $C_{6-14}$ aryl or (ii) 5- to 10-membered aromatic heterocyclic group containing 1 to 4 hetero atoms selected from among nitrogen, sulfur and oxygen as a ring member other than carbon, each of which may be substituted by 1 to 5 substituents selected from the group consisting of halogen, $C_{1-3}$ alkylenedioxy, nitro, cyano, $C_{1-6}$ alkyl which may be halogenated, $C_{3-6}$ cycloalkyl, $C_{1-6}$ alkoxy which may be halogenated, $C_{1-6}$ alkylthio which may be halogenated, hydroxy, amino, mono-$C_{1-6}$ alkylamino, di-$C_{1-6}$ alkylamino, $C_{1-6}$ alkyl-carbonyl, carboxy, $C_{1-6}$ alkoxy-carbonyl, carbamoyl, mono-$C_{1-6}$ alkyl-carbamoyl, di-$C_{1-6}$ alkyl-carbamoyl, C_{6-10} aryl-carbamoyl, sulfo, C_{1-6} alkylsulfonyl, C_{6-10} aryl and C_{6-10} aryloxy;

X is (i) a bond or (ii) a divalent group of the formula: —Xa—Xb— wherein Xa is a bond, S, SO, SO$_2$, O or NR$^4$, wherein R$^4$ is hydrogen, C$_{1-6}$ alkyl, C$_{3-6}$ cycloalkyl, C$_{6-14}$ aryl, C$_{7-11}$ aralkyl, formyl, C$_{1-6}$ alkyl-carbonyl or C$_{6-10}$ aryl-carbonyl; and Xb is (a) a bond or (b) C$_{1-5}$ alkylene, C$_{2-5}$ alkenylene, C$_{2-5}$ alkynylene or a group of the formula: —(CH$_2$)$_p$—Xc—(CH$_2$)$_q$—wherein Xc is S, SO, SO$_2$, O or NR$^{4a}$, wherein R$^{4a}$ is hydrogen, C$_{1-6}$ alkyl, C$_{3-6}$ cycloalkyl, C$_{6-14}$ aryl, C$_{7-11}$ aralkyl, formyl, C$_{1-6}$ alkyl-carbonyl or C$_{6-10}$ aryl-carbonyl; p and q are independently an integer of 0 to 4 and p+q is an integer of 0 to 4, each of which group may be substituted by 1 to 5 substituents selected from the group consisting of (1) halogen, (2) nitro, (3) cyano, (4) C$_{1-6}$ alkyl which may be halogenated, (5) C$_{3-6}$ cycloalkyl, (6) C$_{7-11}$ aralkyl, (7) C$_{1-6}$ alkoxy- which may be halogenated, (8) C$_{1-6}$ alkylthio which may be halogenated, (9) hydroxy, (10) amino, (11) mono-C$_{1-6}$ alkylamino, (12) di-C$_{1-6}$ alkylamino, (13) C$_{6-10}$ aryloxy, (14) C$_{1-6}$ alkyl-carbonyl, (15) C$_{6-10}$ aryl-carbonyl, (16) oxo and (17) a (17-i) C$_{6-14}$ aryl or (17-ii) 5- to 10-membered aromatic heterocyclic group containing 1 to 4 hetero atoms selected from among nitrogen, sulfur and oxygen as a ring member other than carbon, each of which may be substituted by 1 to 5 substituents selected from the group consisting of halogen, C$_{1-3}$ alkylenedioxy, nitro, cyano, C$_{1-6}$ alkyl which may be halogenated, C$_{3-6}$ cycloalkyl, C$_{1-6}$ alkoxy which may be halogenated, C$_{1-6}$ alkylthio which may be halogenated, hydroxy, amino, mono-C$_{1-6}$ alkylamino, di-C$_{1-6}$ alkylamino, C$_{1-6}$ alkyl-carbonyl, carboxy, C$_{1-6}$ alkoxy-carbonyl, carbamoyl, mono-C$_{-6}$ alkyl-carbamoyl, di-C$_{1-6}$ alkyl-carbamoyl, C$_{6-10}$ aryl-carbamoyl, sulfo, C$_{1-6}$ alkylsulfonyl, C$_{6-10}$ aryl and C$_{6-10}$ aryloxy;

R$^2$ is (i) hydrogen, (ii) C$_{1-6}$ alkyl, (iii) C$_{2-6}$ alkenyl (iv) C$_{2-6}$ alkynyl, (v) C$_{3-6}$ cycloalkyl, (vi) C$_{6-14}$ aryl, (vii) C$_{7-16}$ aralkyl, (viii) formyl, (ix) C$_{1-6}$ alkyl-carbonyl, (x) C$_{6-10}$ aryl-carbonyl, (xi) C$_{7-11}$ aralkyl-carbonyl, (xii) C$_{1-6}$ alkylsulfonyl, (xiii) C$_{6-10}$ arylsulfonyl which may be substituted by 1 to 3 substituents selected from the group consisting of C$_{1-6}$ alkyl, C$_{1-6}$ alkoxy and nitro or (xiv) C$_{7-11}$ aralkylsulfonyl;

R$^3$ is hydrogen, C$_{1-6}$ alkyl, C$_{2-6}$ alkenyl, C$_{2-6}$ alkynyl, C$_{3-6}$ cycloalkyl, C$_{6-14}$ aryl or C$_{7-16}$ aralkyl;

ring A is a benzene ring which may be substituted by 1 to 3 substituents selected from the group consisting of halogen, C$_{1-3}$ alkylenedioxy, nitro, cyano, C$_{1-6}$ alkyl which may be halogenated, C$_{3-6}$ cycloalkyl, C$_{1-6}$ alkoxy which may be halogenated, C$_{1-6}$ alkylthio which may be halogenated, hydroxy, amino, mono-C$_{1-6}$ alkylamino, di-C$_{1-6}$ alkylamino, C$_{1-6}$ alkyl-carbonyl, carboxy, C$_{1-6}$ alkoxy-carbonyl, carbamoyl, mono-C$_{1-6}$ alkyl-carbamoyl , di-C$_{1-6}$ alkyl-carbamoyl, C$_{6-10}$ aryl-carbamoyl, sulfo, C$_{1-6}$ alkylsulfonyl, C$_{6-10}$ aryl and C$_{6-10}$ aryloxy, in addition to a group of the formula: —O(CH$_2$)$_m$COR$^1$; and ring B is a 5- to 7-membered ring of the formula:

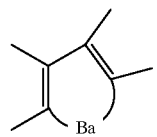

wherein Ba is —CH$_2$—, —(CH$_2$)$_2$—, —(CH$_2$)$_3$—, —CH=CH—, —O—, —O—CH$_2$—, —CH$_2$—O—, —O—CH$_2$—CH$_2$—, —CH$_2$—O—CH$_2$—, —S(O)$_r$—, —S(O)$_r$—CH$_2$— or —S(O)$_r$—(CH$_2$)$_2$— wherein r is an integer of 0 to 2, which ring may be substituted by 1 to 3 substituents selected from the group consisting of C$_{1-6}$ alkyl, C$_{2-6}$ alkenyl, C$_{2-6}$ alkynyl, C$_{3-6}$ cycloalkyl, C$_{6-14}$ aryl and C$_{7-16}$ aralkyl.

3. A compound according to claim 1 wherein the group of the formula: —COR$^1$ is carboxy which may be esterified or amidated.

4. A compound according to claim 1 wherein R$^1$ is hydroxy which may be substituted.

5. A compound according to claim 1 wherein R$^1$ is hydroxy.

6. A compound according to claim 1 wherein m is 1.

7. A compound according to claim 1 wherein Ar is a C$_{6-14}$ aryl which may be substituted by 1 to 3 substituents selected from the group consisting of halogen, C$_{1-3}$ alkylenedioxy, nitro, cyano, C$_{1-6}$ alkyl which may be halogenated, C$_{3-6}$ cycloalkyl, C$_{1-6}$ alkoxy which may be halogenated, C$_{1-6}$ alkylthio which may be halogenated, hydroxy, amino, mono-C$_{1-6}$ alkylamino, di-C$_{1-6}$ alkylamino, C$_{1-6}$ alkyl-carbonyl, carboxy, C$_{1-6}$ alkoxy-carbonyl, carbamoyl, mono-C$_{1-6}$ alkyl-carbamoyl, di-C$_{1-6}$ alkyl-carbamoyl, C$_{6-10}$ aryl-carbamoyl, sulfo, C$_{1-6}$ alkylsulfonyl, C$_{6-10}$ aryl and C$_{6-10}$ aryloxy.

8. A compound according to claim 1 wherein Ar is phenyl which may be halogenated.

9. A compound according to claim 1 wherein X is a divalent group of the formula: —Xa$^1$—Xb$^1$— wherein Xa$^1$ is S, SO or SO$_2$; and Xb$^1$ is C$_{1-5}$ alkylene which may be substituted by a C$_{6-14}$ aryl which may be substituted by 1 to 3 substituents selected from the group consisting of halogen, C$_{1-3}$ alkylenedioxy, nitro, cyano, C$_{1-6}$ alkyl which may be halogenated, C$_{3-6}$ cycloalkyl, C$_{1-6}$ alkoxy which may be halogenated, C$_{1-6}$ alkylthio which may be halogenated, hydroxy, amino, mono-C$_{1-6}$ alkylamino, di-C$_{1-6}$ alkylamino, C$_{1-6}$ alkyl-carbonyl, carboxy, C$_{1-6}$ alkoxy-carbonyl, carbamoyl, mono-C$_{1-6}$ alkyl-carbamoyl, di-C$_{1-6}$ alkyl-carbamoyl, C$_{6-10}$ aryl-carbamoyl, sulfo, C$_{1-6}$ alkylsulfonyl, C$_{6-10}$ aryl and C$_{6-10}$ aryloxy.

10. A compound according to claim 9 wherein Xa$^1$ is S.

11. A compound according to claim 9 wherein Xb$^1$ is C$_{1-3}$ alkylene which may be substituted by a phenyl which may be halogenated.

12. A compound according to claim 1 wherein ring B is a ring of the formula:

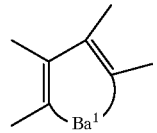

wherein Ba$^1$ is —CH$_2$—, —(CH$_2$)$_2$—, —O—CH$_2$— or —O—.

13. A compound according to claim 1 which is a compound of the formula:

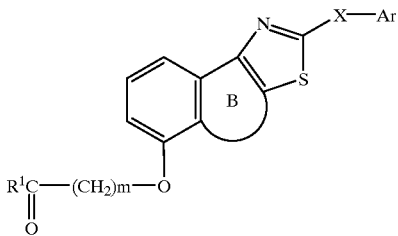

wherein the respective symbols have the same meanings as defined in claim 1.

14. A compound according to claim 13 wherein
$R^1$ is hydroxy;
m is 1;
Ar is phenyl which may be halogenated;
X is a divalent group of the formula: $-Xa^2-Xb^2-$
wherein $Xa^2$ is S, SO or $SO_2$; and $Xb^2$ is $C_{1-3}$ alkylene which may be substituted by a phenyl which may be halogenated; and
ring B is a ring of the formula:

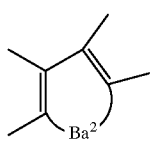

wherein $Ba^2$ is $-CH_2-$, $-(CH_2)_2-$, $-O-CH_2-$ or $-O-$.

15. A compound according to claim 1 wherein
$R^1$ is hydroxy which may be substituted by a $C_{1-6}$ alkyl;
m is an integer of 1 to 3;
Ar is $C_{6-14}$ aryl which may be substituted by 1 to 3 substituents selected from the group consisting of halogen, nitro, cyano, $C_{1-6}$ alkyl which may be halogenated, $C_{1-6}$ alkoxy and $C_{1-10}$ aryl;
X is (i) a bond or (ii) a divalent group of the formula: $-Xa^3-Xb^3-$ wherein $Xa^3$ is a bond, S, SO, $SO_2$, O or NH; and
$Xb^3$ is a $C_{1-5}$ alkylene or $C_{2-5}$ alkenylene group which may be substituted by a phenyl which may be halogenated;
Y is $-S-$;
Z is $-N=$;
ring A is a benzene ring which may be substituted by 1 to 3 $C_{1-6}$ alkyl, in addition to a group of the formula: $-O(CH_2)_mCOR^1$; and
ring B is a ring of the formula:

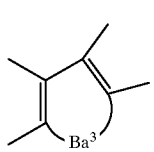

wherein $Ba^3$ is $-CH_2-$, $-(CH_2)_2-$, $-O-CH_2-$ or $-O-$.

16. A compound according to claim 1 which is [(2-diphenylmethylthio-4,5-dihydronaphtho[1,2-d]thiazol-6-yl)oxy]acetic acid,
[(2,2-diphenylethyl)thio-4,5-dihydronaphtho[1,2-d]thiazol-6-yl)oxy]acetic acid,
[(2-diphenylmethyl)sulfonyl-4,5-dihydronaphtho[1,2]thiazol-6-yl)oxy]acetic acid,
[(2-bis-(3-fluorophenyl)methylsulfonyl-4,5-dihydronaphto[1,2-d]thiazol-6-yl)oxy]acetic acid, or
[(2-bis-(2-fluorophenyl)methylsulfonyl-4,5-dihydronaphto[1,2-d]thiazol-6-yl)oxy]acetic acid, or a salt thereof.

17. A compound according to claim 1 which is
[(2-diphenylmethylthio4,5-dihydronaphtho[1,2-d]thiazol-6-yl)oxy]acetic acid,
[(2,2-diphenylethyl)thio4,5-dihydronaphtho[1,2-d]thiazol-6-yl)oxy]acetic acid,
[(2diphenylmethyl)sulfonyl4,5dihydronaphto[1,2-d]thiazol-6-yl)oxy]acetic acid,
[(2-bis-(3-fluorophenyl)methylsulfonyl-4,5-dihydronaphto[1,2-d]thiazol-6-yl)oxy]acetic acid, or
[(2-bis-(2-fluorophenyl)methylsulfonyl-4,5-dihydronaphto[1,2-d]thiazol-6-yl)oxy]acetic acid, or a metal salt thereof.

18. A compound of the formula:

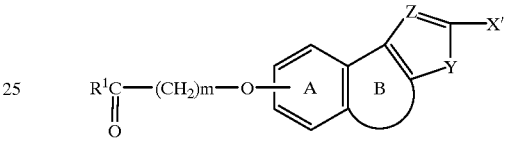

wherein $R^1$ represents hydrogen, a hydroxy which may be substituted or an amino which may be substituted
m represents an integer of 1 to 3;
X' represents SH, OH or $NH_2$;
Y represents $-S-$, wherein $R^2$ represents hydrogen or a subsequent group;
Z represents $-N=$ wherein $R^3$ represents hydrogen or a hydrocarbon group;
ring A represents a benzene ring which may be substituted by a substituent in addition to a group of the formula: $-O(CH_2)m-COR^1$ wherein the respective symbols have the same meanings as defined above; and
ring B represents a 5- to 7-membered ring which may be substituted, or a tautomer thereof, or a salt thereof.

19. A pharmaceutical composition comprising a compound of claim 1 and a pharmaceutically acceptable carrier or excipient.

20. A method for eliciting a prostaglandin $I_2$ receptor agonistic effect in a mammal in need thereof which comprises administering to such mammal an effective amount of a compound of claim 1 with a pharmaceutically acceptable excipient, carrier or diluent.

21. A method for inhibiting platelet aggregation in a mammal in need thereof comprising administering an effective amount of a compound according to claim 1 to said mammal.

22. A method for treating transient ischemic attack, diabetic nephropathy, peripheral vascular disease or ulcer in a mammal comprising administering an effective amount of a composition of claim 1 to a mammal in need of such treatment.

23. A method for inhibiting platelet aggregation in a mammal in need thereof comprising administering an effective amount of a pharmaceutical composition according to claim 19 to said mammal.

24. A method for treating transient ischemic attack, diabetic nephropathy, peripheral vascular disease or ulcer in a mammal comprising administering an effective amount of a pharmaceutical composition of claim 19 to a mammal in need of such treatment.

25. A process for producing a compound of claim 1 which comprises i) reacting a compound of the formula:

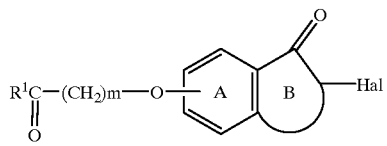

wherein Hal represents halogen;
  wherein $R^1$ represents hydrogen, a hydroxy which may be substituted or an amino which may be substituted;
  m represents an integer of 1 to 3;
  Ar represents an aromatic group which may be substituted;
  X represents a bond or a divalent straight chain group which have 1 to 6 atoms and may be substituted;
  Y represents —S—, wherein $R^2$ represents hydrogen or a substituent group;
  Z represents —N= wherein $R^3$ represents hydrogen or a hydrocarbon group;
  ring A represents a benzene ring which may be substituted by a substituent in addition to a group of the formula; —O(CH$_2$)m—COR$^1$ wherein the respective symbols have the same meanings as defined above; and
  ring B represents a 5- to 7-membered ring which may be substituted, or a salt thereof with a compound of the formula:

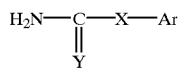

wherein
  Ar represents an aromatic group which may be substituted;
  X represents a bond or a divalent straight-chain group which have 1 to 6 atoms and may be substituted;
  Y represents —S—, or a salt thereof, optionally followed by hydrolysis or oxidation of the resultant compound.

26. A process for producing a compound of claim 1 which comprises reacting a compound of the formula:

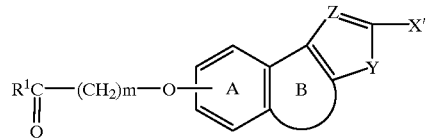

wherein
  X' represents SH, OH or NH$_2$;
  wherein $R^1$ represents hydrogen, a hydroxy which may be substituted or an amino which may be substituted;
  m represents an integer of 1 to 3;

Ar represents an aromatic group which may be substituted;
  X represents a bond or a divalent straight-chain group which have 1 to 6 atoms and may be substituted;
  Y represents —S—, wherein
  Z represents —N= wherein;
  ring A represents a benzene ring which may be substituted by a substituent in addition to a group of the formula: —O(CH$_2$)m—COR$^1$ wherein the respective symbols have the same meanings as defined above; and
  ring B represents a 5- to 7-membered ring which may be substituted, or a tautomer thereof, or a salt thereof with a compound of the formula:

wherein
  L represents a leaving group;
  Ar represents an aromatic group which may be substituted;
  Xb is (a) a bond or (b) $C_{1-5}$ alkylene, $C_{2-5}$alkenylene, $C_{2-5}$alkynylene or a group of the formula: —(CH$_2$)$_p$—Xc—(CH$_2$)$_q$—, wherein Xc is S, SO, SO$_2$, O or NR$^{4a}$, wherein $R^{4a}$ is hydrogen, $C_{1-6}$ alkyl, $C_{3-6}$ cycloalkyl, $C_{6-14}$ aryl, $C_{7-11}$ aralkyl, formyl, $C_{1-6}$ alkyl-carbonyl or $C_{6-10}$ aryl-carbonyl; p and q are independently an integer of 0 to 4 and p+q is an integer of 0 to 4, each of which group may be substituted by 1 to 5 substituents selected from the group consisting of (1) halogen, (2) nitro, (3) cyano, (4) $C_{1-6}$ alkyl which may be halogenated, (5) $C_{3-6}$ cycloalky, (6) $C_{7-11}$ aralkyl, (7) $C_{1-6}$ alkoxy which may be halogenated, (8) $C_{1-6}$ alkylthio which may be halogenated, (9) hydroxy, (10) amino, (11) mono-$C_{1-6}$ alkylamino, (12) di-$C_{1-6}$ alkylamino, (13) $C_{6-10}$ aryloxy, (14) $C_{1-6}$ alkyl-carbonyl, (15) $C_{6-10}$ arylcarbonyl, (16) oxo, and (17) a (17-i) $C_{6-14}$ aryl or (17-ii) 5- to 10-membered aromatic heterocyclic group containing 1 to 4 hetero atoms selected from among nitrogen, sulfur and oxygen as a ring member other than carbon, each of which may be substituted by 1 to 5 substituents selected from the group consisting of halogen, $C_{1-3}$ alkylenedioxy, nitro, cyano, $C_{1-6}$ alkyl which may be halogenated, $C_{3-6}$ cycloalkyl, $C_{1-6}$ alkoxy which may be halogenated, $C_{1-6}$ alkylthio which may be halogenated, hydroxy, amino, mono-$C_{1-6}$ alkylamino, di-$C_{1-6}$ alkylamino, $C_{1-6}$ alkyl-carbonyl, carboxy, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, sulfo, $C_{1-6}$ alkylsulfonyl, $C_{1-6}$ aryl and $C_{6-10}$ aryloxy; in the presence of a base, optionally followed by hydrolysis or oxidation of the resultant compound.

27. A method for manufacturing a pharmaceutical composition for eliciting a prostaglandin $I_2$ receptor agonistic effect, said method comprising combining a compound of claim 1 with a pharmaceutically acceptable carrier, excipient or diluent.

* * * * *